(12) United States Patent
Zheng et al.

(10) Patent No.: US 8,653,007 B2
(45) Date of Patent: Feb. 18, 2014

(54) COMPOSITIONS, METHODS AND RELATED USES FOR CLEAVING MODIFIED DNA

(75) Inventors: Yu Zheng, Topsfield, MA (US); Richard J. Roberts, Wenham, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 13/441,208

(22) Filed: Apr. 6, 2012

(65) Prior Publication Data

US 2012/0202712 A1     Aug. 9, 2012

Related U.S. Application Data

(62) Division of application No. 12/644,666, filed on Dec. 22, 2009.

(60) Provisional application No. 61/140,586, filed on Dec. 23, 2008, provisional application No. 61/267,617, filed on Dec. 8, 2009.

(51) Int. Cl.
*C40B 40/06*     (2006.01)
*C12N 9/00*     (2006.01)
*C12N 9/16*     (2006.01)
*C12N 1/20*     (2006.01)
*C12N 15/00*     (2006.01)
*C07H 21/04*     (2006.01)

(52) U.S. Cl.
USPC .......... 506/16; 435/183; 435/196; 435/252.3; 435/320.1; 536/23.2

(58) Field of Classification Search
None
See application file for complete search history.

(56) References Cited

U.S. PATENT DOCUMENTS 5,643,758 A    7/1997    Guan et al.
7,141,366 B1    11/2006    Sandman et al.

FOREIGN PATENT DOCUMENTS

WO     2006/128140 A2     11/2006

OTHER PUBLICATIONS

Accession A3PUQ5, Apr. 3, 2007.*
Chica et al. Curr Opin Biotechnol. Aug. 2005;16(4):378-84.*
Sen et al. Appl Biochem Biotechnol. Dec. 2007;143(3):212-23.*
Tarasova et al. (BMC Mol Biol. Jan. 15, 2008;9:7.*
Roberts et al. Nucleic Acids Res, 35, D269-270, 2007.
Ehrlich et al, Biochim Biophys Acta, 395, 109-119, 1975.
Vogelsang-Wenke et al, Mol Gen Genet, 211, 407-414, 1988.
Raleigh, Mol Microbiol, 6, 1079-1086, 1992.
Heitman and Model, J Bacteriol, 169, 3243-3250, 1987.
Raleigh and Wilson, PNAS, 83, 9070-9074, 1986.
Mulligan and Dunn, Protein Expr Purif, 62, 98-103, 2008.
Sutherland et al. J Mol Biol, 225, 327-348, 1992.
Waite-Rees et al, J Bacteriol, 173, 5207-5219, 1991.
Lacks and Greenberg, J Biol Chem, 250, 4060-4066, 1975.
Tarasova et al, BMC Mol Biol, 9, 7, 2008.
Aertsen and Michiels, Mol Microbiol, 58, 1381-1391, 2005.
Altschul et al, Nucleic Acids Res, 25, 3389-3402, 1997.
Bujnicki and Rychlewski, Gene, 267, 183-191, 2001.
Marchler-Bauer et al, Nucleic Acids Res, 35, D237-240, 2007.
Pei et al, Nucleic Acids Res, 35, W649-652, 2007.
Bitinaite et al, Nucleic Acids Res, 35, 1992-2002, 2007.
Slotkin et al., Nature Reviews Genetics, 8(4): 272-285 2007.
Li et al., Cell 69: 915-926 1992.
Tahiliani et al., Science 324(5929): 930-935 2009.
Kriaucionis and Heinz Science 324(5929): 929-930 2009.
Morgan et al., Human Molecular Genetics 14(1):R47-58 2005.
Brunner et al., Genome Research (19):1044-1056 2009.
Gargiulo et al., International Journal of Biochemistry and Cell Biology 41: 127-135 2009.
Gronbaek et al., Basic and Clinical Pharmacology and Toxicology 103(5): 389-396 2008.
Yegnasubramanian et al., Nucleic Acid Research 34 e19 2006.
Sen_et_al_Appl._Biochem_Biotechnol._143_212-223_2007.
Accession_A3PUQ5_Mar. 4, 2007.
Chica_et_al._Curr._Opin_Biotechnol_16_378-384_2005.

* cited by examiner

*Primary Examiner* — Christian Fronda
(74) *Attorney, Agent, or Firm* — New England Biolabs, Inc.; Harriet M. Strimpel

(57) ABSTRACT

Compositions, methods and related uses are provided relating to cleaving modified DNA. For example, a set of DNA fragments obtainable by enzymatic cleavage of a large DNA is described where at least 50% are similarly sized and have a centrally positioned modified nucleotide. In addition, an enzyme preparation is provided that includes one or more enzymes that recognize a modified nucleotide in a DNA and cleave the DNA at a site that is at a non-random distance from the modified nucleotide. The one or more enzymes are further characterized by an N-terminal conserved domain with greater than 90% amino acid sequence homology to WXD$(X)_{10}$YXGD. The related uses include creating a methylome, methods of purifying DNA fragments containing a modified nucleotide and diagnostic applications.

10 Claims, 20 Drawing Sheets

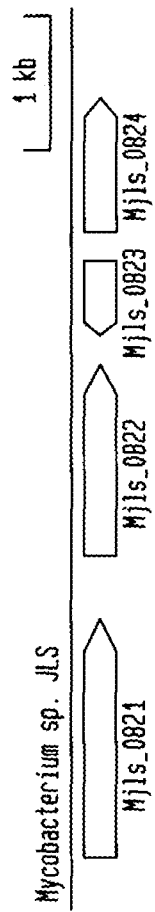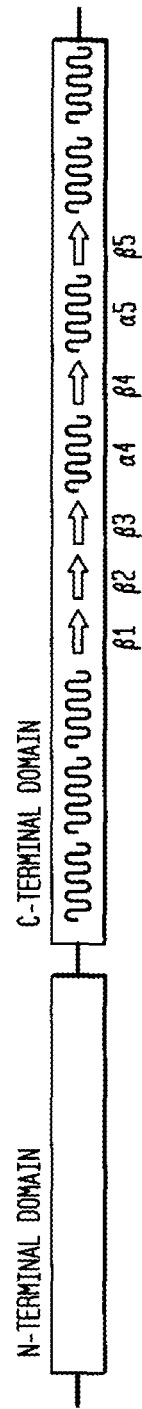

FIG. 1C

```
Conservation:                 59 9 5   9  979987 86           99 9 8             6 69 9
gi_227372459_V_par        66 -EDIDMPDVLEARTGKFAYYGDMKRPGDAVD--SKKGHLLETIFNEKN------RMKIPPVFIFMKNPT    126  (SEQ ID NO: 23)
CAIMIT_00196              67 -EELEMPDLDEEAGVFAYYGDWRKPGNDIRMTEKKGNLLEEVFELLNS----MMLEDMPPFFVFAKTGN    132  (SEQ ID NO: 24)
Franean1_5336            114 -AVADMPDYLDPSTGVFTYYGDWRKPGRDLHBDTQRSGNLLLRDVFEHAHG-SVEERRIVPPFLLFETAPP  181  (SEQ ID NO: 25)
Sgri1_16873               74 -GKVDMRPDYLDVENGTFTYYGDMKRPGERRPGQSLHETPRSGNLLRDAFAASHG-TPADRSKVPPFFLFEKAAA 141  (SEQ ID NO: 26)
AspBHI                    65 -AEPKMPDQLDETTGTFTYYGDMKRPERLHDVPRFGNQLLRQIFDMAH----GQRHLVPPILVFTEAI     130  (SEQ ID NO: 27)
Bcenmc03_0011              1 --------------------------------MLRNLFDEAHQ--FQQSSSFPPILLFGMAGT        29  (SEQ ID NO: 28)
lpg1234                   65 -EDGMPDSIDTSKGQPTYYGDMKHPGHDIHDVPRQGNATLKMLFDSTEN-EKDARRIVPPIFIVKYPT    132  (SEQ ID NO: 29)
Rmet_0004                 23 -EDKDMPDFLDLSTGKFVYFGDMKTPGHELHET-RGGAKVLRYSFERLHA-AVNPRADVAPFLVKKYPL    89   (SEQ ID NO: 30)
RlaI                      67 -KHPDMLDNIDYESGIIQYYGDMKRPERELHDSKRGGNRVLRDVFEMLQD--MRRQKIPPFYFESEE-  131  (SEQ ID NO: 31)
lhv_0031                  77 INYNPMBEDEFNEDVGYINYYGDMKRPDTDPA--TTRGNKYLLDQFKISHDPNPEVRATAVPIIFFETRKQ  144  (SEQ ID NO: 32)
gi_260101829_DSM_20075    27 INYNPMBEDEFNEDVGYINYYGDMKRPDTDPA--TTRGNKYLLDQFKISHDPNSEVRATAVPIIFFETRKQ   94  (SEQ ID NO: 33)
Spea_3849                 79 SIETPMEDFYDVDNGHIRYFGDMKRPGKDPA--TAPGHKALLEAFRLAHSHSAKERALTPPILLFERAVI   146  (SEQ ID NO: 34)
Sbal195_0369              75 SIETPMEDFYDVDMNGHIRYFGDMKRPGKDPA--TAPGHKALLEAFRLAHSHVDERLLTPPILLFERAIY   142  (SEQ ID NO: 35)
PE36_01892                75 SAETPMRQDFYDTDMNGHIRYFGDMKRPGKDPT--QAPGHKALLEAFRLAHSEDDIKERQKTPPIVFFRRVTV  142  (SEQ ID NO: 36)
Xcc3577                   75 SMENPMHDTLAPDEGFARYFGDMRRPDVDPG--TAIGHRTLLRQFFTHSPDQGKRERAAPVILLFRSTKK   142  (SEQ ID NO: 37)
MspJI                     96 HETNPMHDEFDLDHGHVRYFGDPSTVGLDG-ETKGHRILLEAARLHAGTRKERLLAPPLLFLFRAVTV   164  (SEQ ID NO: 38)
Consensus_ss:                           eeeee                                   hhhhhhhhhhhhh  hh    eeeee
```

FIG. 1D

```
Conservation:                  6      99 59                           85    999 9 58   58                       5 5798
gi_227372459_V_par       246 QYYKDEPYKFYFAAKIVGLADN----NFILMFNITRYVRDGGIDAIGEYRLGH----KNNSIKLRCAIRAK  308  (SEQ ID NO: 39)
CATNIT_00196             251 EHYKDNPYGFESCAMDLLMKMDN----HFVDFNLTRPWRDGGRDSLGTYSINSGGKVNAPLKIDCAIRAM  316  (SEQ ID NO: 40)
Franean1_5336            296 EHYRGHEHDYFEFCAVELWRLIAP----ATGRCDVYPSRDGSRDGRDAIGDYILGP----LSDPIALDFALRAK  358  (SEQ ID NO: 41)
Sgrif_16873              257 DYFRGREHDYFELCAVAIWRLAAP----STGAVDVTRPSRDGSRDGRDAVGTYLLGP----AANRIAVDFALRAK  319  (SEQ ID NO: 42)
AspBHI                   243 QRYKENPFGFEACAGALTRLLLP----DVARLDLTRPWRDGSRDGIGRLRLRIGQ----SPAALEVDFALRAK  305  (SEQ ID NO: 43)
Bcenmc03_0011            145 EHYKEDPYAFERCAMELARLPMP----AIQHMELTRPWRDGGRDALGTYRIGH----GAGALDVEFAMRAK  207  (SEQ ID NO: 44)
lpg1234                  248 DYFCEAPIKFEACAAKIFQLDE----NVLIDEITRSAVDGGKDAIGRYVLGI----KEDPVYARFTLRAK  310  (SEQ ID NO: 45)
Rmet_0004                206 QHYKGAPIAFEAFAARVFQMFDE----RVVIDEITRGVDGSRDGRDAIGRYLGS----MADPVYARFSLRAK  268  (SEQ ID NO: 46)
RlaI                     247 DYF-DNPYEFERCAMKIVQLMDS----NIHSLAHTRPFVADGGRDAIGLYRIGR----QCDGVDVEFALRAK  308  (SEQ ID NO: 47)
lhv_0031                 274 SKAHSGDFEFGLAKEITRLLIGD----ACHDGWVTKSSGDGGYDFVLRVDIGT----KGISQVRQVVLGQAK  338  (SEQ ID NO: 48)
gi_260101829_DSM_20075   224 SKAHSGDFEFGLAKEITRLLIGD----ACHDGWVTKSSGDGGYDFVLRVDIGT----KGISQVRQVVLGQAK  288  (SEQ IS NO: 49)
Spea_3849                270 IYTANKKHRFEALAERVIAARVIDREFGIYHKGWVTQSSDGADFVGKVTLGS----GFSKVELIVLGQAK  336  (SEQ ID NO: 50)
Sball95_0369             266 DYTANKKHRFEALAEVIAERVIDRELGIYQKGWVTQSCDSGADFIGKVTLGS----GFSKVELIVLGQAK  332  (SEQ ID NO: 51)
PE36_01892               266 KFYDGRKHFEALAEFITERVIGKELGIYVHKGHIYQSSDGGADPIGKVVLGS----GFSKVELIVLGQAK  332  (SEQ ID NO: 52)
Xcc3577                  261 RPYEPKRHFEALASLACESAVRGTGAEVYRGLTRGTGDGGLDPVGRIDIGE----GLWCTKLJVVLGQAK  327  (SEQ ID NO: 53)
MspJI                    291 KFYDGRKHAFELLASRVAAEVYRESGARYKEGILSRSSGDGGVDPIGRIDMGS----LKASTPVVVLGQAK  357  (SEQ ID NO: 54)
Consensus_ss:                hhh  hhhhhhhhhhhhhh          eeeeeee     eeeeeee                 eeeeeeee
```

FIG. 5

| METHYLASE | EXAMPLE OF SEQUENCING CHROMATOGRAM | MspJI CLEAVAGE SITE | |
|---|---|---|---|
| dcm | SEQ ID NO:2 | me<br>\|<br>CCWGGNNNNNNNNNNNNNN<br>GGWCCNNNNNNNNNNNNNN<br>\|<br>me | C<sup>m</sup>CWGG(9/13) |
| M.AluI | SEQ ID NO:3 | me<br>\|<br>AGCTNNNNNNNNNNNNNN<br>TCGANNNNNNNNNNNNNN<br>\|<br>me | AG<sup>m</sup>CT(11/15) |
| M.HhaI | SEQ ID NO:4 | me<br>\|<br>GCGCNNNNNNNNNNNNNN<br>CGCGNNNNNNNNNNNNNN<br>\|<br>me | G<sup>m</sup>CGC(10/14) |
| M.MspI | SEQ ID NO:5 | me<br>\|<br>CCGGNNNNNNNNNNNNNN<br>GGCCNNNNNNNNNNNNNN<br>\|<br>me | <sup>m</sup>CCGG(9/13) |
| M.HpaII | SEQ ID NO:6 | me<br>\|<br>CCGGNNNNNNNNNNNNNN<br>GGCCNNNNNNNNNNNNNN<br>\|<br>me | C<sup>m</sup>CGG(10/14) |

NOVEL ENZYME

HUMAN DNA

— 32 bp band

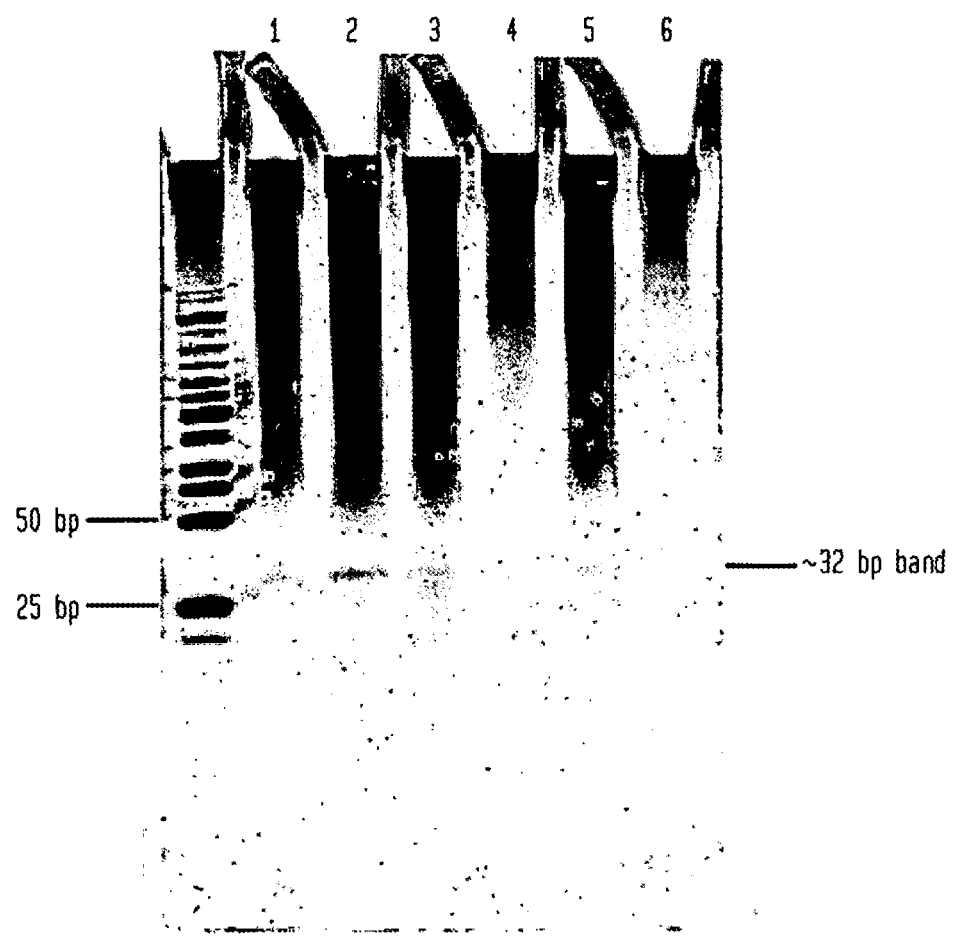

FIG. 7-1

```
Conservation:                                                                    5         6
gi_227372459_V_par          1 MI-----------------------------------SPKDVCE------TEVD    13
CATMIT_00196                1 MV-----------------------------------EVAFEDLQ------NAD    13
Franean1_5336               1 MQSTGVRPCPLASVAVATEVATPGGASDARCLDEPSSGLGSLRAVDDKSQVVPFVDLP------TAA  61
Sgrif_16873                 1 ------------------------MPLADAPV-----PHVTFAELT------TTD    20
AspBHI                      1 --------------------------------------FFTGETLG------QVD    13
Bcenmc03_0011
lpg1234                     1 MK-----------------------------------TYSFDTLA------NAD    13
Rmet_0004
RlaI                        1 MQ-----------------------------------RIAFEKLK------TAD    13
lhv_0031                    1 MV-----------------------------------LHIGVSY---KTGPQAKKEAQ  20
gi_260101829_DSM_20075
Spea_3849                   1 MINI---------------------------------VEIQIGVLRYKKPSC---AVN  23
Sbal195_0369                1 -----------------------------------MEIQIGDVLRYKKPAC---GEN  19
PE36_01892                  1 -----------------------------------MEIKINDILRYKKPAC---HEN  19
Xcc3577                     1 MK-----------------------------------RFRMGELYRYARPAL------PEV  20
MspJI                       1 MNGP-----------------KADIAWAASA------EVANKPRLVFVGDELRYAQGAN----QRD  39
Consensus_ss:                                                                  eee                 hh
```

FIG. 7-2

```
Conservation:                      8       7                  6       5                  76    5
gi_227372459_V_par              14 LVIDEIYEG-----------GAVGNILDDVLTKLMG--VQHAGGFRYRVLNTTD--KAYIVLYSSN------  65
CATMIT_00196                    14 LQIGCVYKG-----------GTAPNLGSDPLSHLFP--CGHAGGFRRVNRDGSRLPAYVLYTSM------  66
Praneanl_5336                   62 LVWDQLYEG-----------GTAGTLADDPLARLLP--VGHQGGFRYAGSPRKGT--VRLSVLYTTG---- 113
Sgrif_16873                     21 LVVDAVYAG-----------GSSGHTGDDPMSKIIKGIGHQGGFRYAGSPALGT--VKLAVLYTSG------  73
AspBHI                          14 LIVDAVYAG-----------YKTERGWMADPLVPLVG--VSRQGGFRYRGT--RER-PTLLVLHSNL------  64
Bcenmc03_0011                                                                                                   
lpgl234                         14 LIIDAVYEG-----------GSSGNASDDPISKIIKGIGMGGFRSAGQ--GIP-KKLIVLYTNN------  64
Rmet_0004                        1 ----------------------------MGGFRVTGR--GEQ-KSNVVLPTTG------  22
RlaI                            14 LFVDAVYES-----------NGATNLNGDVLSKIMS--VGTQGGFRPVNIRHQKGRAAYIVLESTN------  66
lhv_0031                        21 EISDFFYISEDDDSSKNYFIET-------------BLK-DGKKNYFNQAGIFKPAR--MECIIISSNTK-SRG  76
gi_260101829_DSM_20075           1 ----------------YFNQAGIFKPAR--MECIIISSNTK-SRG  26
Spea_3849                       24 MYED----G----------HLMFHFLTK--HSEANNLQLRK-GINPSAKIKTNS--GRL-VRSAILVSSSPNKKG  78
Sbal195_0369                    20 MYED----G----------YLMFHFLTK--SIDANNLQLRK-GINPSAKIKTSL--GQL-VRPAILISSSPNKKG  74
PE36_01892                      20 AYED----G----------HLMFHFLTH--VPTSKKLQLRK-GINPSAALKTSD--KEL-VRPVILISSSPNKKG  74
Xcc3577                         21 LKID----G----------ISNFHYVA--APGSPSLQLER-RINAPSVTRAIDGD------RVAVVLLASNRRKRG  74
MspJI                           40 VELD----G----------PVNYHWLISPGGLGLPKVMLEA-GINAPAEVVGPDRS------RRALIAIRSSPNKAG  95
Consensus_ss:                      hhhhhh                hhhhh             ee       eeeeeeee
```

FIG. 7-3

```
Conservation:                    59 9  5    9   979987 86           99 9   8          6  69  9
gi_227372459_V_par           66 -EDIDWPDVLEAETGKFKYYGDMRPGDKVD--SKKGNLILETIPMKN----------RMKIPPVFIPMKNPT 126
CATMIT_00196                 67 -EELEWPDFLDEETGVFRIYGDMRPGNDIRMTKKAGNLLLEEVFLLMS----MNLEDMPPFFVFKKTGN 132
Praneanl_5336               114 -AVADWPDTLDPSTGVFTYYGDMRKPGROLHDTPQRSGMILLRDVPRHAHG-SVEERRTVPPFLLFETAPP 181
Sgri1_16873                  74 -GEVDWPDYLDVETGTFTYYGDMRRPGQSLHETPRSGHILLRDAPAASHG-TPADRSKVPPFTLFEKAAA 141
AspBHI                       65 -AEPEWPDQLDETTGTFIYYGDMREPGRALLHDTPRPENQLLRQIFWAEL----GQRHLVPPILVTTLAP 130
Bcenmc03_0011                 1 ----------------MLRNLFDEARQ--FQQSSSFPPILLPGNAGT 29
lpg1234                      65 -EDGDWPDSIDFSKQFIYYGDMRKPGHDIHDTPRQGNATLKMLFDSTHN-EKDARRIVPPIPIFVKYPT 132
Rmet_0004                    23 -EDKDWPDTLDLSTGKFVIFGDMRTPGHELHET-RGGHKVIRYSPERLHA-AVNPRADVAPPLVFKAYPL 89
RlaI                         67 -KHPDWLDWIDYESGIIQYYGDWREPGRELHDSRGGHKVLRDVFEMLQD---WRRQEIPPFYFESE- 131
lhv_0031                     77 INYNPWEDEFMEDVGYINYYGDMKRPDFTDPA--TFRGWKYLLDQFKISHDPNPEVRATAVPIIFFETRKQ 144
gi_260101829_DSM_20075       27 INYNPWEDEFMEDVGYINYYGDMKRPDFTDPA--TFRGWKYLLDQFKISHDPNSEVRATAVPIIFFETRKQ 94
Spea_3849                    79 SIETPWEDFIDVDNGHIRYFGDMKEPGKDPA--TAPGWKALLEAFRLAEHSAKERALTPPILFFKRAVI 146
Sball95_0369                 75 SIETPWEDFIDVDNGHIRYFGDMKEPGKDPA--TAPGWKALLEAFRLAESHVDERLLFPPILFFKRAIV 142
PK36_01892                   75 SAETPWQDFIDTDWGHIRYFGDMKEPGKDPF--QAPGWKALLEAFRLAESHDIKERQRTPPIVFFKRYT 142
Xcc3577                      75 ------PLAIGHRTLLRQFFHTSPDQGKRERAAPVLLFRSTKK 142
MspJI                        96 HETNPWHDEFDLDEGHVRYFGDHKPSTVGLPG-ETKGHRLLIRAARLHAGTTREERLLAPPLPLFRAVTV 164
Consensus_ss:                                            eeeee                    hhhhhhhhhhhh       hh    eeeee
```

FIG. 7-4

```
Conservation:              7   8 86          655 5         8 98 5 7676               96
gi_227372459_V_par     127 VAS-NRSVRFLGLAVPEDYTLGKDNSLKAITRTS-NSE-RFTNYEAHFTILNTK----SINRKWLSCLIN 189
CAMMP_00196            133 ----GRDIQFLGLAAPGNSNISPGRDLVALNCSI-NGQ-KPQNTEAYFTILDFRG-KGISRDWTKSLSE 194
Praneanl_5336          182 ----GRRIMFRGLLAPGAATLRSDDDLVAITRNT-RGH-RPQNYRAHFVLDVA----TVTRKWLTDILA 241
Sgrif_16873            142 R---GRSVLFRGLLAPGGPNLTSDDELAAITRAI-DGR-RPQNYRARPFVLEVD----RVPRAMFQHLLN 202
AspBHI_131             142 ----GRRFRFRGLAVPGSPALAATEDLVALMKTI-EGQ-RPQNYKAVFTILDEA----VIPRAMVHAVER 190
Bcenmc03_0011           30 ----TRDVRFLGLAVPGAAGMGADDDLVAVNRTEDGV-RPQNYKAPFTILDLP----VVSRAFIKDVQN  90
lpg1234                133 ASS-SRSVQFKGVAVPGYPGLSATDDLLAVNKTT-NGQ-RPQNYRAIPFIILNIP----MVSRKWINSLFD 195
Rmet_0004               90 AHG-ARSVQFKGLAVPGFPSLSSTEDLVAVNKSS-EGQ-RPQNYRAVFFILMAP----VLSRAFINDLKA 152
RlaI                   132 ----GRMRRFIGLLVPGSDKFTLKELLVAITRMK-NGE-RVQNYKAVFTILDVA----SVSRGMLEDLLS 191
lhv_0031               145 ----GERIFHGYG--------VIKNVKLVTQYTQSGADKAYFSNYLFTPCVFSMKKKQEGFDWSTEARIQ 203
gi_260101829_DSM_20075  95 ----GERIFHGYG--------VIKNVKLVTQYTQSGADKAYFSNYLFTPCVFSMKKKQEGFDWSTEARKQ 153
Spea_3849              147 NGVAKGYTPQFYGLG------IINSVELVTQWDNK-LAR-TFTNYAPDFTVLCIASEHEEPKMDWINSRRK 208
Sbal195_0369           143 NGVAKGYTPQFYGLG------IINSVELVTQWDNK-LAR-TFTNYAPDFTVLCIAGHEKFHDWINRRK 204
PE36_01892             143 NGVPKGYTMFQGLG-------IINSIELVTQHDNN-KQQ-SPTNYAPDFTVLCMAKRDTFNDWINSRH 204
Xcc3577                143 ----GFKEFSGLA--------LLVGARRVTQFSEK-NGG-FFTNYLFDLAVLSLTRDESLAMTHDRRD 199
MspJI                  165 ERA-GRAVVKGHVEPCGAA--TIERLRHVQRDPH-TGR-SPTHLSLDLAVVSGGE-IDGVDFRHIDDRRH 229
Consensus_ss:              eeee e         e       e    eeeeee       e  ee        eeeeeee  hhhhhhhh
```

FIG. 7-5

```
Conservation:          59 8 6 7                                                      5                    5       5 5
gi_227372459_V_par  190 GD-------SLNTRFAPDAMLKYVRQGLTDDII-------LSA-PKNKEYRSKIEQLPSTDKDLRKLDFIY         245
CATMIT_00196        195 DH-------SASIDVAPDVWKKFISQGRDGIRA-------LKA-PKIIHIPSKCDQLQCDDEGKKCVDAIR       250
Pranean1_5336       242 GH-------ATDSEHCPPAWTAWVDGRAYSP--------LIA-PSTTIIRTAEQQPPDPTGVAIIAAIR        295
Sgrif_16873         203 GG-------DPLDGE-CPDANRTWTESRVYRP--------LIA-PSTTVVRSKADQLPGDAVGKAMLQEIR       256
AspBHI              191 G--------ETSGLAPVAWNAWLSAGGIRP----------LMA-PRSLLVRSKAEQLPATPKDQALIEVIR       242
Bcenmc03_0011        91 GH-------AVSSAHAPKAWLDWSGRKYTP----------LKS-VPVSVVRSKRQQVPDTPRLAAYVKTVY      144
lpg1234             196 PF-------GQDNSLN--PFYQWKISGKADV---------LIA-PSTKTIRTQIEQMPRTKLEREILQAVF      247
Rmet_0004           153 GD-------LNSSWAPRAWRQWRESGKYSP----------LAA-APTTNIRSANBAQSPDTALRRELLECIW    205
Rlal                192 GH-------GYQSDFAPKEWKWIDKGVTP-----------LYASDSVLNYRTQXQMPFKDDKRQKLQSIY      246
lhv_0031            204 AAKDKNFLSLANALAPKEWKFWIRTGDLEKVRRKVYGRSTSKKEEQLPTPGSADDKILNQIYEYYRKKDN      273
gi_260101829_DSM_20075 154 AAKDKNFLSLANALAPKEWKFWIRTGDLEKVRRKVYGRSTSKKEEQLPTPGSADDKILNQIYEYYRKKDN     223
Spea_3849           209 KGF-------SLSITWKASPKSWRQFLIEGSNSLNKLR-----RRV-SKLSLEKTVWQKPIPGSESDRILWEIY     269
Sbal195_0369        205 KAF-------SLAITNQTAPKSWRQFLCKGSSNALNKLR----RRV-SKLSLEKAVWQKPIPGSESDKILNQIY     265
PK36_01892          205 PMP-------SIQDTNKAPASWNQWFFKSGANELNTVR-----RRV-SKLQIVKSADQKFTIGSEQDALINKIY    265
Xcc3577             200 PSR-------ACGVAWAMAPKAWQRWVKPGSPEIERIK-----RRV-ARYIHLPEKDQVAPVSSEGGKTLRAIY    260
MspJI               230 AAL-------AAGETLRHAPESWIRWVRQGRLAIPGIR-----RRV-LASAVQSSKEQQPASSGAEAATLQTLY   290

Consensus_ss:                    hhh hhhhhhhhh                                   hhhhh  hhhhhhhhhhh
```

FIG. 7-6

```
Conservation:           6     99 59              85    999 9 58    58             5 5798
gi_227372459_V._par  246 QYYKDEPIKFEYFAAKLVGLNDN----NFLNFHITRTVRDGGIDAIGEYRLGH---KNNSIKLRCALEAK 308
CATMIT_00196         251 EHYKDNPYGFESCANDLLMRNDN----HFVDFNLTRPNRDGGRDSIGYYSINSGKVNAPLKIDCALEAM 316
Franean1_5336        296 EHYRGREDFEKFCAVELNRLIAP----ATGRCDVTPPSRDGGRDAIGDYILGP---LSDPIAIDFALEAK 358
Sgri1F_16873         257 DYFRGREHDFELCAVAITRLNAP----STGAVDYTRPSRDGGRDAVGTYLLGP---AANRIAVDFALEAK 319
AspBHI               243 QRYKHNPPGFEACAGALTRLLLP----DVARLDLTRPNRDGGRDGIGRLRIGQ---SPAAIEVDFALEAK 305
Bcenmc03_0011        145 EHYKDPYAFERCAMELARLFMP----AIQHNELTRPNRDGGRDALGTYRIGH---GAGAIDVEFAMEAK 207
lpg1234              248 DYFCKAPIKFEACAAKIFQLYDE----NVLIDEITRSAVDGGKDAIGRYVLGI---KEDPVYAEFFIRAK 310
Rmet_0004            206 QHYKGAPIAFEAFAARVPQMTDE----RVVIDEITRGVDGGRDAIGENYRLGS---MADPVYARFSIRAK 268
RlaI                 247 DYF-DNPYHFKCAMKIVQLMDS----NIHSLKHTFVRDGGRDAIGLYRIGR---QCDGVDEFALEAK 308
Lhv_0031             274 SKAHSGDFEFGLAKEITRLLIGD----ACHDGNVTKSSGDGGYDFVLRVDIGT---KGISQVRQVVLGQAK 338
gi_260101829_DSM_20075 224 SKAHSGDFEFGLAKEITRLLIGD----ACHDGNVTKSSGDGGYDFVLRVDIGT---KGISQVRQVVLGQAK 288
Spea_3849            270 IYYANKKEHFEALAEVIABRVIDREFGIYHKGNVTQGSSDGGADFVGKVTLGS---GFSKVELIVLGQAK 336
Sbal195_0369         266 DYYANKKEHFEALAEVIABRVIDRELGIYQKGNVTQGSGDGGADFIGKVTLGS---GFSKVELIVLGQAK 332
PE36_01892           266 KFYDGRKHHFEALAEFITERVIGKELGIYHRGNTTQGSSDGGADFIGKVVLGS---GFSKVELIVLGQAK 332
Xcc3577              261 RFYEPKRHRFEALASLACKSMVRGTGAEYHRGLIYRGTGDGGLDPVGRIDIGR---GLMGTKLVVLGQAK 327
MspJI                291 KFYDGRKHAFELLASRVAAEVTRESGARYKEGNLSRSSGDGGVDFIGRIDMGS---LKASTPVVLGQAK 357
Consensus_ss:            hhh hhhhhhhhhhh                       eeeeeee      eeeeeeee                    eeeeeee
```

FIG. 7-7

```
Conservation:        86          6    59577977 7 58557998    577 95  9 797    7                                                                                    ?
gi_227372459_V_par    309 CYQRD--------NSNGVKLLSRLISRLKYRDFGIFVTTSYVSEQAYKELLEDGHPVIIISGGDIIEILTNN    372
CATMIT_00196          317 CYAET--------NGIGIKQMSRLISRIRYRQFGILITTSYVDEQAYQEVVEDGHPILVVTATDIARILRIN    380
Franean1_5336         359 CYTDT--------NSVGVRDYARLISRLRERHPGYFTITTSHFNQQVTTEVRTDRHPIALVSGRDIVNALRAH    422
Sgrif_16873           320 CYGPD--------NSVGVREYSRLISRLRERHFGVLVTTSFLAKQVQDEIQEDGHPIALVCGRDIVEVLAQH    383
AspBHI                306 CYGAN--------NAVGVKEVSRLISRLRERFPGVLVTTSYVDRQAYQEVTDDGHPVILTAQDIVGLLRSA    369
Bcenmc03_0011         208 CYDQN--------VGVGIKPLSRLLISRLRERQFGILVTTSYLDAQAYSELVHDTHPVVYISAKDISMKLRER    271
lpg1234               311 CYQPGLMGQNINSVGVKEVYSRLISRIKHRQFGVLVTTSFIAKQAYGEVREDGHPIVFLSGGDISRILLKK    380
Rmet_0004             269 CYRPPLMGDTPITVSVSDVARLISRIRERQFGVLVTTSVLASQAYKEVREDRHPIVFISGGDMVNILLIDK    338
RlaI                  309 RYSSN--------DGIGVKEVSRLISRLRERQFGILVTTSFVALQAYQEIKEDGHPIVISGMDILRILYDS    372
lhv_0031              339 CYRRD--------QRITGEAVDRVVARLKRGHTAAFYTTSFFSDPAQREILEDDYPIMLISGKQVAQTVRKY    402
gi_260101829_DSM_20075 289 CYRRD--------QRITGEAVDRVVARLKRGWTAAFYTTSFFSDPAQREILEDDYPIMLISGKQVAQTVRKY    352
Spea_3849             337 CEALN--------SPTGGNHIARYVARLKRGHLGYVVTTSYDSDSVQREVIEDKYPILLIHGRRIAEKVAKI    400
Sbal195_0369          333 CESLN--------TPPFGGNHIARTVARLKRGJLGYVVTTSYFSDSVQREVIEDKYPIVLIHGRRIAEKVAKI    396
PE36_01892            333 CESLT--------TPPFGGNHIARTVARLKRGJLGAYVTTSYFSDSVQREVIEDKYPILLINGKRIAEKVSQL    396
Xcc3577               328 CEKID--------APTGGVHLIARTVARLRRGHLGAIYTTSFFSEAVQREVHDDQQIYPVLLNGAGLAAFVTKL    391
MspJI                 358 CIQPT--------SSVSPEQVARVVARLRRGHIGYVVTTGSFSRQAQVELIDDQIYPVLLIAGGTLAAYVRM    421
Consensus_ss:         ee                    eeeeee          hhhhhhhhhh  eeeee     hhhhhhhh   eeeee   hhhhhhhhh
```

FIG. 7-8

| | | | |
|---|---|---|---|
| Conservation: | | | |
| gi_227372459_V._par | 373 RIN------TKESLLNFMDTIDYL--------------- | 390 | (SEQ ID NO: 7) |
| CAtMIT_00196 | 381 SIT------SENIDEYLNSI-DSRRKEWEQDK-------- | 405 | (SEQ ID NO: 8) |
| Fraenanl_5336 | 423 CYA------DVNAVNAELGK-IPNVHVSAKG----APNP- | 450 | (SEQ ID NO: 9) |
| SgriT_16873 | 384 GRF------TADSVRQML---------------FQS---FPQP- | 402 | (SEQ ID NO:10) |
| AspBHI | 370 GVR------TPTQVDAMLDG-ITASV-------------- | 388 | (SEQ ID NO:11) |
| Bcenmc03_0011 | 272 FGS------LESIKLWLQRI-------------------- | 285 | (SEQ ID NO:12) |
| lpg1234 | 381 GIN------STDAVLAWLRS-EFSKS-------------- | 399 | (SEQ ID NO:13) |
| Rmet_0004 | 339 GTN------TRGRVQRLLSS-DFALV-AAASSEPVDKPR | 369 | (SEQ ID NO:14) |
| RlaI | 373 GIK------TKDEIQEHLVK-TFPKDE-------------- | 392 | (SEQ ID NO:15) |
| lhv_0031 | 403 IYE------KNITLREYLD-SLSRDQSPKSPEDILKEE | 433 | (SEQ ID NO:16) |
| gi_260101829_DSM_20075 | 353 IYE------KNITLREYLD-SLSRDQSPKSPEDILKEE | 383 | (SEQ ID NO:17) |
| Spea_3849 | 401 VYESKRFESVNSFLVAMDK-DYPTRLKQRQAEKVLNT- | 436 | (SEQ ID NO:18) |
| Sball95_0369 | 397 VYESKAYSNVTEFLIAMDA-VYPSRLKQRQAEKILNW- | 432 | (SEQ ID NO:19) |
| PE36_01892 | 397 LHESDFYSDIDEFLAYMAE-RYPKRLKQRQPEKILHV- | 432 | (SEQ ID NO:20) |
| Xcc3577 | 392 RLEGG-FASTEQFLRHIDA-DYEAQVSSRPEKVLME- | 426 | (SEQ ID NO:21) |
| MspJI | 422 VQANY-GGDLDALLASTVD-EYGAAVTHRRPEEVISL- | 456 | (SEQ ID NO:22) |
| Consensus_ss: | hhhhhhhh hhh | | |

FIG. 8-1

=== human: 28217009 CG sites ===
frag length: 60    distinct: 26185493    unique: 25538480,    91% of total,    98% of distinct unique
frag length: 50    distinct: 25390748    unique: 24629494,    87% of total,    97% of distinct unique
frag length: 40    distinct: 24023595    unique: 23175261,    82% of total,    96% of distinct unique
frag length: 38    distinct: 23754147    unique: 22891192,    81% of total,    96% of distinct unique
frag length: 36    distinct: 23470437    unique: 22589181,    80% of total,    96% of distinct unique
frag length: 34    distinct: 23135519    unique: 22237296,    79% of total,    96% of distinct unique
frag length: 32    distinct: 22729132    unique: 21819726,    77% of total,    96% of distinct unique
frag length: 30    distinct: 22324226    unique: 21403356,    76% of total,    96% of distinct unique
frag length: 28    distinct: 21906872    unique: 20975707,    74% of total,    96% of distinct unique
frag length: 26    distinct: 21454942    unique: 20518776,    73% of total,    96% of distinct unique
frag length: 24    distinct: 20967530    unique: 20031532,    71% of total,    96% of distinct unique === mouse 20954953 CG sites ===
frag length: 60    distinct: 19122616    unique: 18854613,    90% of total,    99% of distinct unique
frag length: 50    distinct: 18901437    unique: 18616493,    89% of total,    98% of distinct unique
frag length: 40    distinct: 18582440    unique: 18272284,    87% of total,    98% of distinct unique
frag length: 38    distinct: 18502525    unique: 18187467,    87% of total,    98% of distinct unique
frag length: 36    distinct: 18417202    unique: 18097163,    86% of total,    98% of distinct unique
frag length: 34    distinct: 18327241    unique: 18001732,    86% of total,    98% of distinct unique
frag length: 32    distinct: 18230156    unique: 17898012,    85% of total,    98% of distinct unique
frag length: 30    distinct: 18127303    unique: 17796867,    85% of total,    98% of distinct unique
frag length: 28    distinct: 18012369    unique: 17662034,    84% of total,    98% of distinct unique
frag length: 26    distinct: 17884300    unique: 17520927,    84% of total,    98% of distinct unique
frag length: 24    distinct: 17727151    unique: 17346584,    83% of total,    98% of distinct unique

FIG. 8-2

```
===== Arabidopsis 2783857 CG sites =====
# frag length: 60  distinct: 2689980 unique: 2639418, 95% of total, 98% of distinct unique
# frag length: 50  distinct: 2672244 unique: 2615465, 94% of total, 98% of distinct unique
# frag length: 40  distinct: 2646976 unique: 2581568, 93% of total, 98% of distinct unique
# frag length: 38  distinct: 2640676 unique: 2573244, 92% of total, 97% of distinct unique
# frag length: 36  distinct: 2633321 unique: 2563575, 92% of total, 97% of distinct unique
# frag length: 34  distinct: 2625066 unique: 2552776, 92% of total, 97% of distinct unique
# frag length: 32  distinct: 2616350 unique: 2541363, 91% of total, 97% of distinct unique
# frag length: 30  distinct: 2606757 unique: 2528736, 91% of total, 97% of distinct unique
# frag length: 28  distinct: 2595874 unique: 2514364, 90% of total, 97% of distinct unique
# frag length: 26  distinct: 2584180 unique: 2499087, 90% of total, 97% of distinct unique
# frag length: 24  distinct: 2570299 unique: 2480789, 89% of total, 97% of distinct unique
```

COMPOSITIONS, METHODS AND RELATED USES FOR CLEAVING MODIFIED DNA

CROSS REFERENCE

This application is a divisional application of U.S. Ser. No. 12/644,666 filed Dec. 22, 2009, which claims priority from U.S. Provisional Application Ser. No. 61/140,586 filed Dec. 23, 2008 and Ser. No. 61/267,617 filed Dec. 8, 2009, herein incorporated by reference.

GOVERNMENT RIGHTS

This invention was made with Government support under contract 5R44GM095209-03 awarded by the National Institutes of Health. The Government has certain rights in this invention.

BACKGROUND

DNA cleaving enzymes associated with methyltransferases are widely present in the prokaryotic genomes. The DNA cleaving enzymes typically consist of restriction endonucleases, which protect host cells from invading DNA (e.g., bacteriophages) by cleaving DNA at defined sites, and DNA methyltransferases, which protect host DNA from being degraded by methylating a specific base within the restriction endonuclease sites (Roberts, et al. *Nucleic Acids Res* 35: D269-270 (2007)). Hence, these restriction endonucleases are termed methylation-sensitive.

While modified bases in prokaryotes and phage DNA play a role in protecting the genome against cleavage by restriction endonucleases, methylated cytosine (m5C) is involved in gene expression of the mammalian genome. Techniques for identifying methylated DNA are cumbersome and experimentally difficult to implement in a reproducible fashion. Two approaches are commonly used. One involves the use of restriction enzymes like HpaII and MspI which are differently sensitive to cytosine methylation. For example, HpaII endonuclease is blocked by methylation of either of the two cytosines within the CCGG recognition site, but its isoschozimer, MspI, is blocked only when the outer C is methylated. It will cleave DNA when the inner cytosine is modified. The second method involves bisulfite modification of the unmethylated cytosine residues followed by selective amplification and sequencing of the remaining DNA. In this method, methylated cytosines are resistant to the treatment. This method is not easy to optimize and involves a complicated chemical modification step followed by amplification using a complicated set of primers. The method is widely used in the absence of simpler alternative approaches.

SUMMARY

In an embodiment of the invention, a set of double-stranded oligonucleotide fragments are provided that are obtainable by enzymatic cleavage of a large DNA wherein the large DNA contains one or more modified nucleotides and may be derived from mammalian cells, more specifically human cells. At least 50% of the fragments in the set should preferably be of a similar size and preferably contain a centrally positioned modified nucleotide. One or more fragments may be isolated from the set. The large DNA may be at least 100 nucleotides in length; the modified nucleotide is, for example, a modified cytosine such as a methylated cytosine or a hydroxymethylated cytosine and a modified cytosine may be proximate to a guanine to form a CpG or a CNG. However, a modified cytosine may be alternatively located next to another cytosine, an adenine or a thymidine. Oligonucleotide fragments in the set may preferably be less than 60 nucleotides long, for example 28-36 nucleotides; and/or the modified nucleotide, in particular, cytosine may be located within 30 nucleotides from either end of the fragment.

In an embodiment of the invention, an enzyme preparation is provided that is characterized by one or more enzymes that recognize a modified nucleotide in a DNA such that each enzyme is capable of cleaving the DNA at a site that is a non-random distance from the modified nucleotide. More particularly, the non-random distance between the cleavage site and the modified nucleotide may be characteristic for the enzyme so as to generate a set of fragments of the type described above. The one or more enzymes are further characterized by an N-terminal conserved domain with greater than 90% amino acid sequence homology with $WXD(X)_{10}YXGD$ (SEQ ID NO:55), more particularly with greater than 90% amino acid sequence homology with $WXD(X)_6G(X)_3YXGD(X)_{10-15}GN(X)_2LX_{10-20}PX_3F$ (SEQ ID NO:56).

In an embodiment of the invention, the one or more enzymes in the enzyme preparation are further defined by a recognition domain and a cleavage domain within a single open reading frame. The cleavage domain may have an amino acid sequence which has greater than 90% amino acid sequence homology to $FEX_{20-30}DX_{2-4}DX_{19-22}(Q/E)XK$ (SEQ ID NO:57). In addition, at least one of the enzymes may have an amino acid sequence homology of greater than 90% to any of the sequences identified as SEQ ID NOS:7-22. Additionally, one or more of the enzymes may be covalently or non-covalently linked or fused to a protein affinity tag or other tag. Examples of suitable affinity tags include a chitin-binding domain, maltose-binding domain, an antibody and a His tag. In addition, the one or more enzymes may be recognized by an antibody with binding specificity for an amino acid sequence comprising $WXD(X)_{10}YXGD$ (SEQ ID NO:55). Additionally, the preparation may include an activator DNA.

In an embodiment of the invention, an enzyme preparation is provided that includes one or more enzymes that recognize a modified nucleotide in a DNA such that each enzyme is capable of cleaving the double-stranded DNA at a site that is at a non-random distance from the modified nucleotide, more particularly where the distance between the cleavage site and the modified nucleotide is characteristic for the enzyme, thereby generating a set of fragments. The set of fragments may be of similar size if the DNA contains a modified nucleotide on each strand of the duplex at approximately opposing positions or may be of varying size for hemi-modified DNA. The one or more enzymes may be further characterized by an N-terminal conserved domain with greater than 90% amino acid sequence homology to $WXD(X)_{10}YXGD$ (SEQ ID NO:55).

In an embodiment of the invention, an antibody is provided that is capable of recognizing and binding to an N-terminal domain of an enzyme described above.

In an embodiment of the invention, a method is provided which comprises cleaving a large DNA containing one or more modified nucleotides with a composition described above and obtaining a set of oligonucleotide fragments. The method may further include separating the set of oligonucleotide fragments from uncleaved DNA and additionally may include sequencing from the separated set of fragments at least one fragment to determine the location of one or more modified nucleotides contained within at least one fragment. The method may include analyzing some or all of the oligonucleotide fragments for the presence and location of one or more modified nucleotides in the large DNA by sequencing or other means and mapping the sequences onto a genome or methylome map to determine the location of modified nucleotides.

In an embodiment of the invention, a method is provided for identifying an enzyme such as described above that includes searching a sequence database using a sequence selected from the group consisting of SEQ ID NO:7-22 and variants thereof, and identifying additional sequences having an N-terminal region characterized by a consensus sequence of $WXD(X)_{10}YXGD$ (SEQ ID NO:55). The method may include the further step of identifying a C-terminal end comprising a catalytic domain with a consensus sequence of $FEX_{20-30}DX_{2-4}DX_{19-22}(Q/E)XK$ (SEQ ID NO:57), more particularly $FE(X)_2A(X)_{15-18}T/SX4DGGXDX_2G/LX_{15-20}E/QAK$ (SEQ ID NO:58).

In an embodiment of the invention, a method is provided for isolating from a mixture of DNA fragments those DNA fragments containing one or more modified nucleotides, the mixture resulting from enzyme cleavage of a large DNA containing at least one modified nucleotide. The method may include adding to the mixture an immobilized or labeled affinity-binding molecule that is capable of binding selectively those fragments containing a modified nucleotide. Alternatively, those fragments containing a modified nucleotide may be size-separated from those fragments that do not contain a modified nucleotide. An example of an affinity-binding molecule is an enzyme preparation described above, wherein the one or more enzymes in the enzyme preparation have been mutated so as to lack enzyme cleavage activity and wherein the mutated enzyme is immobilized on a solid surface so as to bind the DNA fragments containing one or more modified nucleotides. Other examples of affinity-binding molecules include antibodies, inactivated T4 glucosyltransferase and the methyl-binding domain of a cell protein such as DNMT1. These molecules may in turn be fused to any of a chitin-binding domain, a maltose-binding domain or a biotin molecule for example and hence, bind to a suitable column.

In another embodiment of the invention, a method is provided for identifying a present or future phenotypic property in a cell preparation or tissue sample from a pattern of modified nucleotides. The method includes cleaving into fragments a large DNA from a cell preparation or tissue by means of an enzyme preparation described above; and comparing a location for modified nucleotides in the fragments with a pattern of modified nucleotides in a control DNA so as to determine a present or future phenotypic property.

In another embodiment of the invention, the above method further comprises contacting the cleavage fragments with an affinity-binding molecule capable of binding the modified nucleotide or by means of electrophoresis or other means known in the art capable of effecting size separation. The binding moiety may include an enzyme preparation as described above, wherein the enzyme cleavage activity has been inactivated by conventional means. Thus, fragments with a modified nucleotide may be separated from fragments lacking a modified nucleotide. The above method may additionally include identifying on a methylome or a genome a location for the one or more modified nucleotides in the immobilized cleavage fragments. The location may be determined by sequencing the separated fragments.

In another embodiment of the invention, a method is provided for determining the location of at least one modified nucleotide in a large DNA. The method includes: cleaving a large DNA with an enzyme preparation described above; obtaining a set of oligonucleotide cleavage products containing at least one modified nucleotide; and determining the location of the at least one modified nucleotide in a sequence of the large DNA by for example sequencing the set of oligonucleotide cleavage products. The number of oligonucleotide fragments for sequencing in the set may depend on whether the set is derived from cloned DNA or from repeats in which it may be sufficient to sequence a subset of fragments or on whether the set is expected to contain unique sequences in which it may be desirable to sequence substantially all the fragments in the set.

In an embodiment of the invention, a method is provided for obtaining a purified preparation of fragments containing one or more modified nucleotides that includes contacting a mixture of DNA fragments in which one or more the fragments contain at least one modified nucleotide with an immobilized affinity-binding protein capable of binding covalently or non-covalently to the DNA fragment. An example of an affinity-binding protein is a mutated enzyme in the enzyme preparation described above, wherein the enzyme cleavage activity has been inactivated. The method may further include binding the one or more fragments containing at least one modified nucleotide to the binding protein; and obtaining a purified preparation of fragments containing one or more modified nucleotides.

In an embodiment of the invention, a kit for generating oligonucleotide fragments containing a modified nucleotide is provided that includes an enzyme preparation described above in a container with instructions for use. The kit may further include an activator molecule.

BRIEF DESCRIPTION OF THE FIGURES

FIGS. 1A-1B show the MspJI RM system.

FIG. 1A shows the genomic segment of *Mycobacterium* sp. JLS encoding the MspJI RM system. NCBI annotations for open reading frames are: Mjls0821, putative helicase; Mjls0822 (MspJI), restriction endonuclease; Mjls0823 (V.MspJIP), DNA mismatch endonuclease vsr; Mjls0824 (M.MspJI), DNA cytosine methyltransferase.

FIG. 1B shows the schematic domain structure of the MspJI enzyme family. The N-terminal domain is defined here as about 50% of the protein sequence upstream of the remaining C-terminal domain.

FIG. 1C shows the conserved motif in the N-terminal domain.

FIG. 1D shows the conserved motif in the C-terminal domain.

Lane 1, 1 μg of pBR322(dcm+) DNA only;
Lane 2, 1 μg of pBR322(dcm+)+0.8 μg MspJI;
Lane 3, 1 μg of pBR322(dcm+)+0.8 μg MspJI+10 units of BstNI;
Lane 4, 1 μg of pBR322(dcm+)+10 units of BstNI only;
Lane 5, 1 μg of pBR322(dcm−) DNA only; and
Lane 6, 1 μg of pBR322(dcm−)+0.8 μg MspJI.

All reactions were incubated at 37° C. for 1 hour and resolved on a 1% agarose gel. Lanes 3 and 4 show that MspJI does not cut any sites not cut by BstNI. Thus, on this substrate which is methylated at CmC A/T GG, only modified Dcm sites are cut by MspJI. All Dcm sites are cut by BstNI which is not sensitive to Dcm methylation.

Figure 2A:
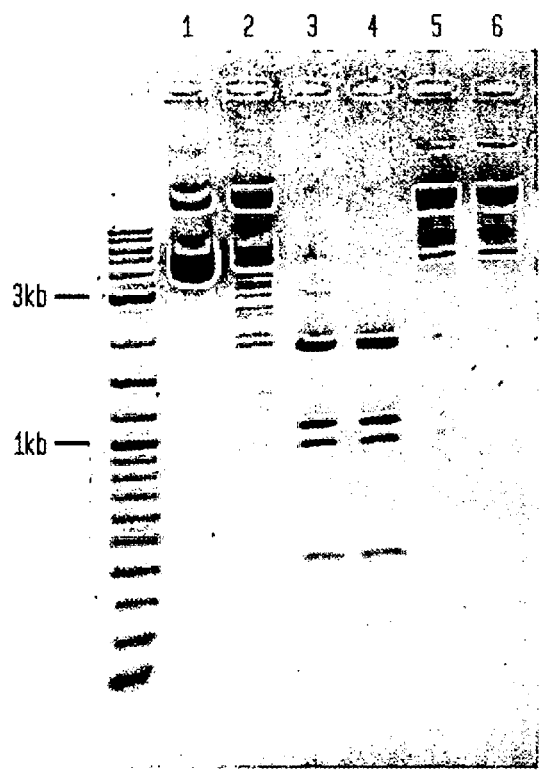
FIG. 2A shows modification-dependent enzyme activity for MspJI.
Figure 2B:
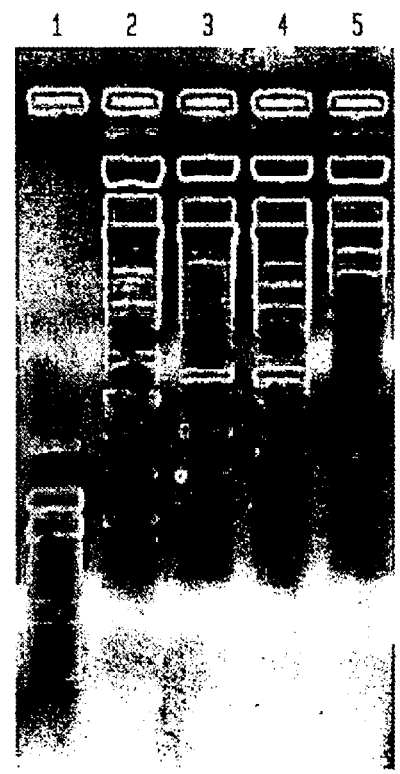

FIG. 2B shows MspJI digestion on pBR322(dcm−) methylated at other sites. All reactions were done in 50 μl volume at 37° C. for 2 hours and resolved on 1% agarose gel. 0.8 μg of MspJI were used in all reactions.

Lane 1, 1 μg of M.MspI ($C^mCGG$) modified pBR322;
Lane 2, 1 μg of M.HaeIII ($GG^mCC$) modified pBR322;

Lane 3, 1 μg of M.HpaII (C'"CGG) modified pBR322;
Lane 4, 1 μg of M.HhaI (G'"CGC) modified pBR322; and
Lane 5, 1 μg of M.AluI (AG'"CT) modified pBR322.

Figure 2C:
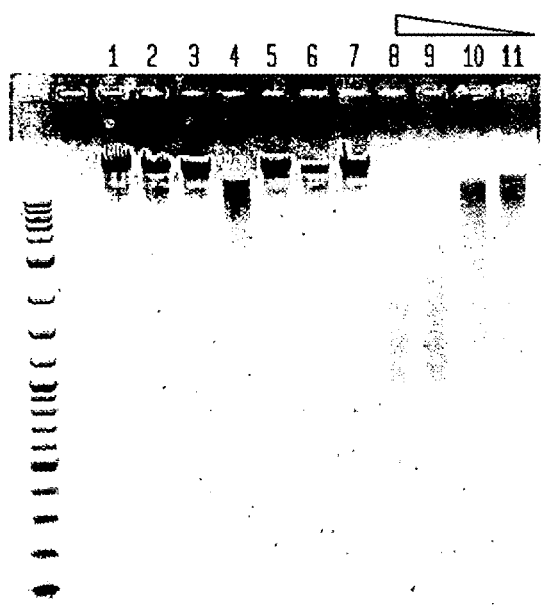

FIG. 2C shows MspJI digestion on hydroxymethylcytosine-containing DNA. All reactions were carried out in 50 μl volume at 37° C. for 1 hour.
Lane 1, 1 μg of T4 wild-type (wt) DNA with glucosylated hydroxymethylcytosine;
Lane 2, 1 μg of T4 gt DNA with hydroxymethylcytosine;
Lane 3, 1 μg of T4 wt DNA+10 units of McrBC;
Lane 4, 1 μg of T4 gt DNA+10 units of McrBC;
Lane 5, 1 μg of T4 wt DNA+20 units of MspI;
Lane 6, 1 μg of T4 gt DNA+20 units of MspI;
Lane 7, 1 μg of T4 wt DNA+0.8 μg of MspJI; and
Lanes 8 through 11, 1 μg of T4 gt DNA with 2-fold serially-diluted MspJI starting at 1.6 μg (Lane 8).

Figure 2D:
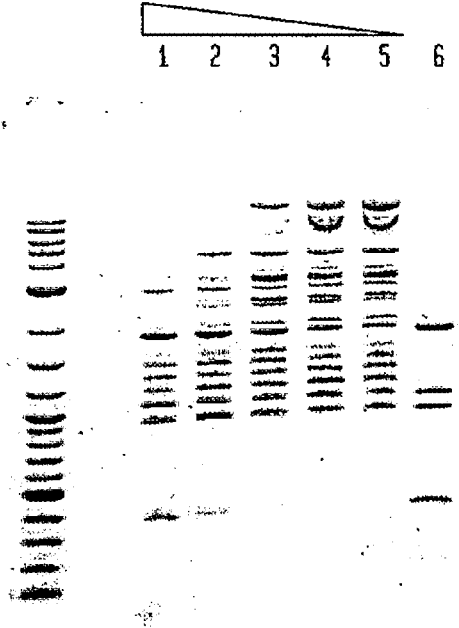

FIG. 2D shows the effect of different amounts of a DNA activator on MspJI activity. From Lanes 1 to 5, each reaction contains 1 μg (0.35 pmol) pBR322 and 1.6 pmol MspJI. Lanes 1-4 show a titration (40, 20, 10, 5 pmol) of the DNA activator containing methylated CCWGG sites. Lane 5 shows pBR322-digestion using MspJI without DNA activator. Lane 6 shows pBR322-digestion using BstNI (CCWGG).

Figure 3:
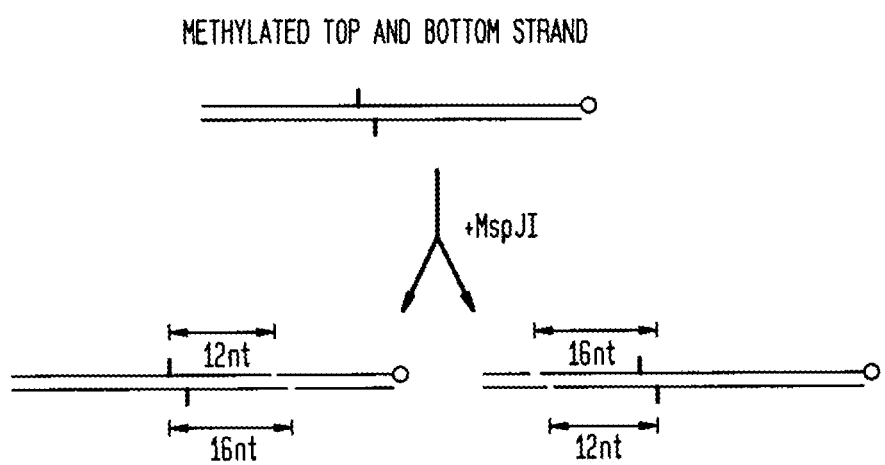

FIG. 3 shows a schematic diagram of MspJI's cleavage activity on fully-methylated DNA. The double-stranded cleavage can happen at either side of the methylated site. The cleavage is on the 3' side of the recognized methylated base. In this figure, when the top strand methylated cytosine is recognized, MspJI cleaves on the right side; when the bottom strand methylated cytosine is recognized, MspJI cleaves on the left side. The distances from the cleavage sites to the recognized methylated cytosine are fixed. For example, when top strand methylated cytosine is recognized, the bottom strand nicking site is 16 nucleotides away from it and the top strand nicking site is 12 nucleotides away from it.

FIGS. 4A-4D show MspJI cleavage on fully-methylated and hemi-methylated oligo substrates, fractionated on a denaturing gel.

Figure 4A:
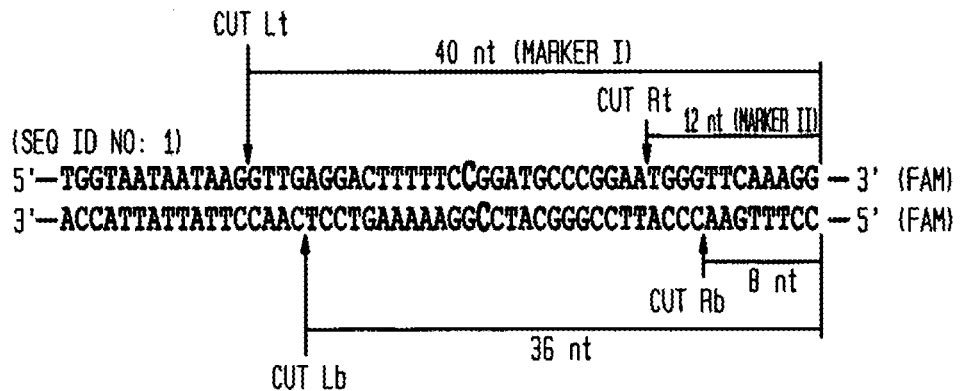

FIG. 4A shows the expected enzyme cleavage sites (designated Rt, Rb, Lt, Lb) in a synthetic double-stranded oligonucleotide TGGTAATAATAAGGTTGAGGACTTTTTC-CGGATGCCCGGAATGGGTTCAAAGG (SEQ ID NO:1). The 3' end of the top strand or the 5' end of the bottom strand is labeled with FAM as indicated in 4B.

Figure 4B:
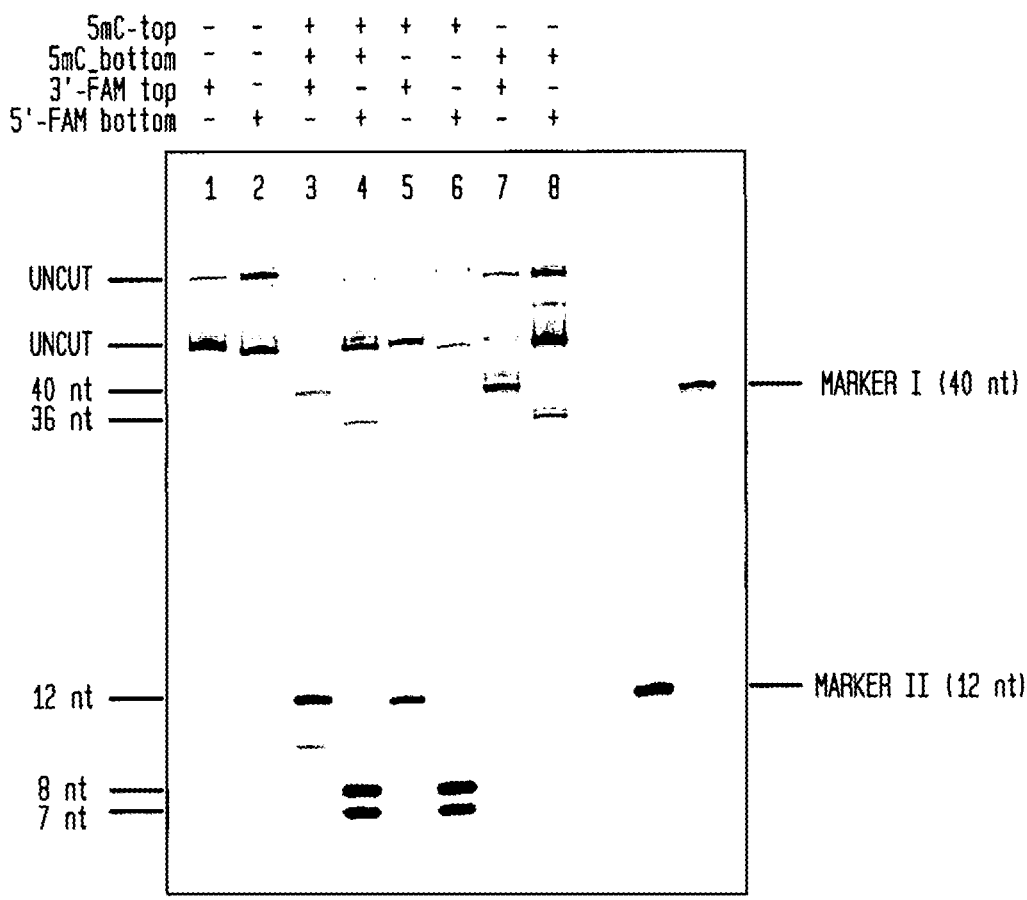

FIG. 4B shows MspJI-digestion on fully and hemi-methylated oligo substrates.
Lane 1, no methylation, top strand labeled;
Lane 2, no methylation, bottom strand labeled;
Lane 3, both top and bottom methylated, top strand labeled;
Lane 4, both top and bottom strand methylated, bottom strand labeled; cleaved products with sizes of 8 nt and 7 nt suggest wobbling cuts in the bottom strand;
Lane 5, top strand methylated, top strand labeled;
Lane 6, top strand methylated, bottom strand labeled; as in Lane 4, cleaved products with sizes of 8 nt and 7 nt suggest wobbling cuts in the bottom strand;
Lane 7, bottom strand methylated, top strand labeled; and
Lane 8, bottom strand methylated, bottom strand labeled.
As a control, markers are run on the right side of the gel.

Figure 4C:
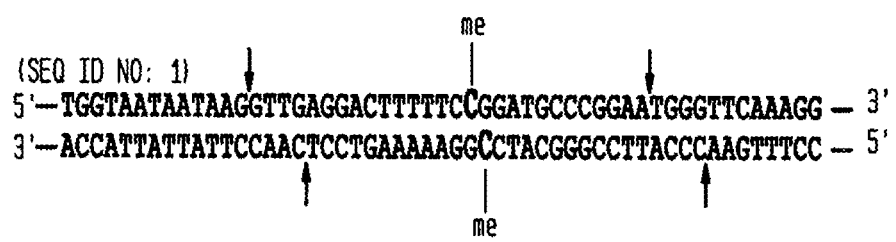

FIG. 4C shows an oligonucleotide sequence having a CpG and enzymatic cleavage sites that would yield a fragment with the CpG in a central location.

Figure 4D:
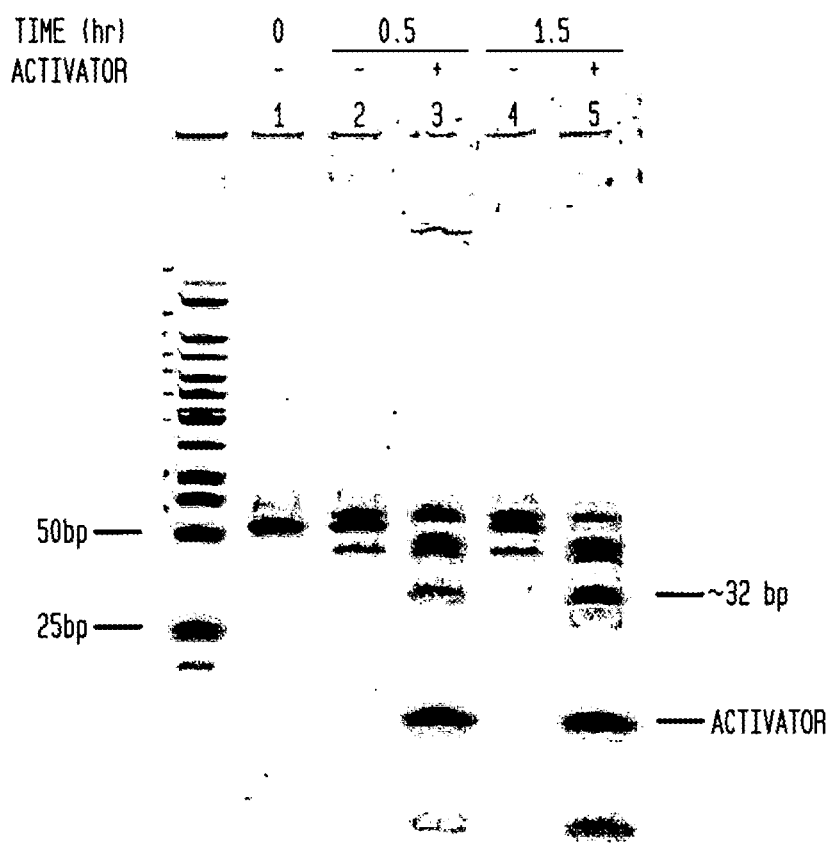

FIG. 4D shows digestion of the oligonucleotide shown in FIG. 4C using MspJI in the presence or absence of activator DNA. Reactions were done in 10 μl at 37° C. for 1 hour. The oligonucleotide is 1 pmol and MspJI is 0.4 μg in each reaction. In reactions with activator, 1 μl of stock (15 μM) was added into the 10 μl reaction. 5 μl of reactions were taken out and stopped at different time points and resolved on 20% native polyacrylamide gel.
Lane 1, DNA only;
Lane 2, digestion reaction without activator at 30 min;
Lane 3, digestion reaction with activator at 30 min;
Lane 4, digestion reaction without activator at 1.5 hour; and
Lane 5, digestion reaction with activator at 1.5 hour.

FIG. 5 shows the sequence analysis of MspJI cleavage site positions on different m5C methylated sites. pBR322 DNA (dcm−) was methylated using various methyltransferases. The methyltransferases are shown under the column heading "methylase". The run-off sequencing pattern is shown under the column "examples of sequencing chromatogram" (SEQ ID NOS:2-6). The deduced cleavage patterns are shown in column "MspJI cleavage site".

Figure 6A:

FIG. 6A shows a double-stranded DNA with a centrally located modified cytosine, which is a representative fragment of the set of oligonucleotides obtained when a large DNA is cleaved with a member of the novel enzyme family.

Figure 6B:

FIG. 6B shows a DNA sample of human genomic DNA on a polyacrylamide gel in which the set of oligonucleotide fragments shown in FIG. 6A appear as a coherent band. The 32 bp band represents the pool of short fragments containing methylated CpG sites from the genome. This pool can be purified and directly put into the Next-Generation sequencing platforms for methylome analysis.

FIG. 6C shows a comparison of cleavage products generated by various member enzymes in the MspJI family. The first lane contains DNA markers. All subsequent lanes contain the digests of CpG-methyated Hela genomic DNA, each with a different MspJI family member enzyme. Lanes 1-3 and 5 show a band that corresponds to about 32 nucleotides in length (arrow). In lane 4, RlaI recognizes CCWGG and cleaves on either side of the recognition site to provide a centrally located modified cytosine. However, this sequence is not found in Hela genomic DNA.
Lane 1 shows the cleavage product from MspJI;
Lane 2 shows the cleavage product from Frankia 5336;
Lane 3 shows the cleavage product from Lpg 1234;
Lane 4 shows the cleavage product from RlaI;
Lane 5 shows the cleavage product from AspBHI; and
Lane 6 shows DNA only.

FIGS. 7-1 to 7-8 shows the amino acid sequence alignment of representative members of the MspJI family of enzymes. Residues conserved in 5 or more members of the alignment are indicated in the top line ("Conservation"). Secondary structure prediction is listed at the bottom ("Consensus_ss"). Secondary structural elements are: e, β sheet; h, α helix.

FIGS. 8-1 to 8-2 shows a bioinformatics analysis of CG-centered sequences of different lengths in three organisms. Total number of CG sites are listed for each organism for human, mouse and *Arabidopsis* genomes. Columns report the number of CG-centered sequences that are distinct (differ in sequence), the number that are unique (occur in single copy), the fraction of the total such CG-centered sequences that are unique and the fraction of distinct CG-centered sequences that are unique (single copy).

DETAILED DESCRIPTION OF THE EMBODIMENTS

A novel family of modification-specific DNA cleavage enzymes has been found where the members of the family recognize a modified nucleotide in double-stranded DNA and then cut at a non-random distance downstream (3' direction) from the modified nucleotide. One of the unique properties of these enzymes is that they are capable of releasing short DNA fragments containing a modified nucleotide directly from large DNA including genomic DNA. These enzymes are capable of generating double-stranded breaks in the DNA on both strands when a modified nucleotide is present in opposing positions on each strand. When DNA contains a modified nucleotide on one strand only, double strand breaks occur on one side of the modified nucleotide. The location of the modified nucleotide in a large DNA can thus be deduced by cloning the cleavage products and/or by sequencing. Using ultra high throughput sequencing platforms, it is possible to identify and map modified nucleotides such as methylated cytosines or hydroxyl-methylated cytosines in a reliable and quick manner.

"Modified" nucleotide is intended to refer to any nucleotides that contain an extra chemical group such as a 5-hydroxymethyl or 5-methyl group. For example, a "modified" cytosine generally arises in mammalian genomes as a CpG and in plant genomes as a CNG which, because of the symmetry, make possible methylation on both strands at the same position. Hydroxymethylcytosine has been recognized as a constituent of human DNA (Tahiliani et al., *Science* 324 (5929): 930-5 (2009); Kriaucionis and Heintz, *Science* 324 (5929): 929-30 (2009)).

"Large DNA" is intended to refer to any naturally occurring or synthetic DNA having a size greater than 100 nucleotides up to a size of a genome.

"Similar size" with reference to a "set" of oligonucleotide fragments is intended to refer to fragments that vary no more than about ±5 nucleotides in length. However, different "sets" of fragments may have a size range of 5-50 nucleotides.

"Centrally positioned" is intended to correspond to a location of a modified nucleotide on one strand which is approximately centered in the same strand of a double-stranded fragment. The location is generally within 5 nucleotides of the center determined by counting the nucleotides from either end of the fragment.

"N-terminal domain" refers to a region extending to about 50% of the amino acid sequence of the protein. In an embodiment of the invention, a conserved region within the N-terminal domain corresponds to amino acids 81 to 224 of SEQ ID:NO:22 (MspJI) and a conserved region within the C-terminal domain corresponds to amino acids 300 to the C-terminus of the protein (SEQ ID NO: 22 (MspJI)).

A "set of oligonucleotide fragments" of similar size obtained by cleavage of a large double-stranded DNA refers to the fragments resulting from cleavage of the large DNA on both sides of a modified nucleotide when the modified nucleotide is located on one strand approximately opposite to another modified nucleotide on the second complementary strand.

An "enzyme preparation" is intended to refer to a reagent and not something occurring in its natural state in vivo.

If a genome that consists of multiple large DNAs (e.g., chromosomes) is cleaved, each large DNA will give rise to a set of oligonucleotide fragments of similar size. A mixture of fragments obtained from cleavage of an entire human genome can be considered as a plurality of sets of oligonucleotide fragments, each set derived from a chromosome or as a single set of fragments depending on the context. In an embodiment, the set of oligonucleotides comprises at least 6 oligonucleotide fragments with different DNA sequences. For example, the set of oligonucleotides may comprise at least 10 oligonucleotides with different sequences or at least 20 oligonucleotides with different sequences. In one embodiment, a cloned double-stranded DNA can be enzymatically modified at a target nucleotide at one site for example, modification of a cytosine at a CpG on both strands. In this example, double strand cleavage by a member of the MspJI enzyme family will occur on both sides of the modified cytosine at a non-random distance. The set of oligonucleotides will consist of similarly sized fragments with a centrally located modified nucleotide.

Members of the newly described MspJI family of enzymes have been identified from microbial sources although enzymes in the family are not limited to those found in microbes. A BLAST search has shown that the number of sequences identified in the DNA database containing genomes from all living sources that encode proteins in the family as defined herein is relatively small. Sixteen homologs are shown in FIGS. 1C, 1D and 7-1 to 7-7 and their % sequence identity and % homology (similarity) are shown in Table 2.

Enzymes capable of recognizing a modified nucleotide and cleaving the DNA at a non-random distance from the modified nucleotide have been found to share sequence motifs in the N-terminal domain. These enzymes have been found to be capable of uniquely cleaving the DNA on both sides of the modified nucleotide to produce a fragment of a non-random size. A modification on the 5 position of cytosine (m5C) in a eukaryotic genome is most commonly associated with regulation of gene expression. Embodiments of the invention may encompass enzymes capable of recognizing a modified cytosine at a CpG site, the exocyclic N4 position of cytosine (mN4C) or a modified nucleotide other than cytosine such as adenine, for example, the exocyclic N6 position of adenine (mN6A) where such enzymes cleave on either side of the modified recognition sequence.

The family of enzymes defined herein by a conserved sequence domain and certain functional features include derivative enzymes or variants that have sequence modifications outside or inside the recognition and/or catalytic domains. Additionally, recombinant derivative enzymes or enzyme variants are included in the family that may be fused to a second protein which serves as a label, tag or marker (U.S. Pat. No. 5,643,758) or may contain a substitution which acts as a label such as occurs with a selenocysteine substitution (see U.S. Pat. No. 7,141,366). In addition to the above described family of enzymes, derivative enzymes and enzyme variants are contemplated in which the catalytic domain is modified or absent such that the N-terminal domain acts as a methylated DNA or hydroxymethylated DNA binding domain.

The use of the MspJI family of enzymes to generate a set of oligonucleotide fragments may rely on a single enzyme or may include a plurality of enzymes where some or all of the enzymes are members of the MspJI family or are derived from members of the MspJI family.

The members of the newly defined family, before chemical modification or mutation, can be defined structurally by one or more of the features listed below.
  (a) non-heteromeric;
  (b) recognition and cleavage functions in a single open reading frame;
  (c) the coding sequence and protein sequence do not contain methyltransferase motifs;
  (d) at least 90% sequence homology to a conserved motif in the N-terminal domain which is WXD(X)$_{10}$YXGD; and
  (e) common secondary structure elements that encompass the conserved motif.

FIG. 1B and FIGS. 7-1 to 7-7 show an embodiment of the enzyme family in which the overall order of the secondary structure elements that build the catalytic core is helix(H1)- helix(H2)-sheet(S1)-sheet(S2)-sheet(S3)-helix(H3)-sheet(S4)-helix(H4) (see, for example, FIGS. 7-1 to 7-7 where h=helix and a series of e represents a β-pleated sheet). The conserved FE is in an α-helix H2; the first conserved aspartic acid (D) is in a hinge region between two β sheets S1 and S2; the second conserved aspartic acid is in β sheet S2; the conserved (Q/E)XK is in a β sheet S3.

Members of the family may be identified by a BLAST search using a sequence selected from SEQ ID NO:7-22 or a related sequence. The hits are then further searched for the above specified consensus sequence in the N-terminal domain and also optionally searched for at least 90% sequence homology or identity in the C-terminal domain of a consensus sequence $FEX_{20-30}DX_{2-4}DX_{19-22}(Q/E)XK$. Optionally, the conserved sequence in the N-terminal domain can be extended to greater than 90% sequence homology to $WXD(X)_6G\ (X)_3YXGD(X)_{10-15}GN(X)_2L\ X_{10-20}PX_3F$ and/or greater than 90% sequence homology with $FE(X)_2A(X)_{15-18}\ T/SX_4DGGXDX_2G/LX_{15-20}E/QAK$.

The selected sequences may then be expressed by techniques known in the art, for example in vitro transcription-translation (PURExpress™, New England Biolabs, Inc. (NEB), Ipswich, Mass.) or by cloning into a microbial host lacking modified bases such as #ER2655 (NEB Express, #C2523, NEB, Ipswich, Mass.) and assayed for cleavage of DNA containing modified nucleotides to produce oligonucleotide fragments of a defined size and/or containing a centrally located modified nucleotide.

Antibodies may be raised to members of the newly defined family of enzymes (MspJI enzyme family) using standard techniques for generating monoclonal or polyclonal antibodies. These antibodies or fragments thereof may be used for in situ-labeling of a member of an MspJI enzyme family bound to the modified large DNA. The enzyme may be mutated so that the cleavage function is inactivated or removed. In this context, the fragments may then be separated by binding to affinity matrices capable of antibody binding.

Functionally, MspJI was identified as a DNA sequence in the database adjacent to a methylase gene sequence and was hence named an endonuclease gene. However, when it was expressed as a protein, it was found to be inactive using standard assays for determining restriction endonuclease activity. This would have normally terminated any further study but for the fortuitous discovery described here that when incubated with DNA from a Dcm+ strain of *E. coli*, the enzyme was active, while it was inactive when tested on DNA from a Dcm− strain of *E. coli*. When the enzyme was incubated with eukaryotic DNA that is known to contain modified cytosines such as human genomic DNA, a smear of high molecular weight DNA was observed on polyacrylamide gels together with a clearly visible band containing fragments that correspond to a size of about 32 base pairs (see FIG. 6B).

A family of related enzymes were identified (FIGS. 7-1 to 7-7) and DNA cleavage by representative examples of these enzymes were tested with human genomic DNA. The tested enzymes yielded a set of similarly sized oligonucleotide fragments of about 32 nucleotides as can be observed on the gel in FIG. 6C.

The newly defined family of enzymes described here is of particular interest for reasons that include their ability to recognize nucleotide residues modified at the 5 position and to produce a set of oligonucleotide fragments where cleavage occurs at a substantially fixed distance downstream of the enzyme recognition site on the DNA (see FIGS. 6A, 6B and 6C). In embodiments of the invention, the cleavage distance from the modified sites conform to the following rules:

(1) For double-stranded DNA with a palindromic m5 CpG or other modified nucleotide on both strands in close proximity, a double-stranded break may be generated on each side of the modified nucleotide to generate fragments of similar size. In one embodiment, the distance between the cleavage site on one strand with a modified CpG was found to be 12 bases and the distance to the cleavage site on the opposite strand from the m5C was found to be 16 bases (MspJI) including a 4 base overhang resulting in oligonucleotide fragments of 32 bases in length.

(2) For hemi-modified double-stranded DNA, a double-stranded break occurs at a position which is 3' downstream from the modified nucleotide. The distance from the cleavage site on the same strand to the modified nucleotide is constant (for example for MspJI the distance is 12 bases and the distance from the cleavage site on the other strand to the modified nucleotide is 16 bases). Sites of hemi-modification in the DNA can be detected by ligating an oligonucleotide containing a site recognized by an MmeI-like enzyme (such as MmeI, see U.S. Pat. No. 7,115,407) to a hemi-modified DNA cleaved at one side at a site 16 nucleotides from the modified nucleotide. The oligonucleotide may include four degenerate nucleotides at the 5' end of the MmeI-site oligonucleotide to allow annealing to the 4 base extension on the bottom strand. Alternatively, a blunt-ended oligonucleotide might be used such that the single strand region at the 4-base extension is filled in using standard molecular biology techniques. The MmeI-like enzyme will cleave 18 or 19 nucleotides upstream which for MspJI cleavage fragments is about 2 nucleotides upstream of the modified fragment. Fragments produced in this manner can be sequenced and the position of the hemi-modified nucleotide in the DNA determined.

The number of CpG sites in genomes from human, mouse and *Arabidopsis* has been determined using bioinformatics. If the genomes of these organisms are then cleaved into various length fragments from 24 bases to 60 bases containing a centrally positioned CpG, then the fragments with unique sequences represent between 71% and 91% of the total unique sequence in humans according to increasing size, 83% to 90% in mice and 89% to 95% in *Arabidopsis* by the same criteria.

If those sequences of a defined length which have a distinct sequence are distinguished from the total sequence and separately analyzed, then 96%-98% of fragments of size 24-60 nucleotides will match a single locus in the human genome. In the bioinformatic analysis provided in FIGS. 8-1 to 8-2, if the fragment length is 60 nucleotides, then there are 26,185,493 fragments that contain a centrally positioned CpG of which 25,538,480 have distinct sequences and 98% of these match a single locus in the genome (see FIGS. 8-1 to 8-2).

Hence, there is significant informational value in a set of oligonucleotide fragments generated by an enzyme in the newly defined family where the enzyme recognizes a modified nucleotide and cleaves the DNA at a distance from the modified nucleotide to preferably generate fragments of a similar size. The data shows that a large fraction of such fragments are highly likely to map to a single locus in the genome. This makes possible for the first time a simple and efficient method for creating a methylome. Consequently, high throughput sequence analysis can yield the location of the majority if not all of the actual modified nucleotides in the genome rapidly and easily.

In an embodiment of the invention, screening assays are described for determining modification-specific cleavage activity of an enzyme (see Example 1). These assays are not intended to be limiting. In one embodiment, selected host cells were transformed with a plasmid containing a specific DNA methyltransferase gene. The expressed methyltransferase then methylated the host genome at specific sites. Hundreds of methyltransferases with varying defined sequence specificities have been described in the literature (see for example REBASE®, a publicly available online database maintained by New England Biolabs, Ipswich, Mass.). Any of these methyltransferases with different methylation specificities can be used for screening purpose. Introduction of a compatible plasmid expressing a gene with modification-dependent cleavage activity able to act on the host's modification pattern would reduce or eliminate the viability of these transformed cells, leading to a low transformation plating efficiency. Non-methylated hosts would show high plating efficiency in a parallel transformation with the methylation-specific endonuclease gene. Thus, this test would confirm the modification-dependent cleavage property of the encoded gene product.

It was found that the activity of the enzymes in the MspJI family can be enhanced in the presence of a double strand DNA activator preferably having a length of less than 16 bp and containing a modified dcm site (for example, dcm ($C^{5m}CWGG$) site). A 30 bp cleavage-resistant DNA activator containing phosphorothioate linkages at the cleavage site also stimulated the enzyme reaction.

Determining the level of methylation or hydroxymethylation of DNA samples is important for epigenetic studies. Epigenetic regulation of the genome includes chromatin remodeling which may be accomplished by the addition of methyl groups to the DNA, mostly at CpG sites to convert cytosine to 5-methylcytosine, and its reversal possibly via hydroxymethylcytosine. Methylation of cytosines in the eukaryotic genome may persist from the germline of one parent into the zygote marking the chromosome as being inherited from this parent (genetic imprinting). Moreover, large changes in methylation occur following zygosis and in tissues of the developing organism (Morgan et al. *Hum Mol Genet* 14 Spec No. 1:R47-58 (2005)). In addition, methylation in some regions of the genome may vary in response to environmental factors (Li, et al *Cell* 69 (6): 915-926 (1992)). Differences in methylation pattern may be critical indicators of inappropriate developmental processes for example for embryonic stem cells (Brunner et al. *Genome Research* 19:1044-1056 (2009)).

Certain enzymes (such as DNMT1) have a high affinity for the m5C. If this enzyme reaches a "hemi-methylated" portion of DNA (where methylcytosine is in only one of the two DNA strands), the enzyme will methylate the other half.

DNA methylation occurs in repeated sequences, and helps to suppress the expression and mobility of transposable elements (Slotkin, et al. *Nat Rev Genet.* 8(4):272-85 (2007)). Because of spontaneous deamination, 5-methylcytosine can be converted to thymidine; hence, CpG sites are frequently mutated and thus become rare in the genome, except at CpG islands where they remain unmethylated. Deamination in this situation converts cytosine to uracil. Diagnostic changes in methylation pattern have the potential to detect increased frequencies of permanent genetic mutation. Methylation in the human genome has been studied in cancer cells for purposes of exploring therapies (see for example, Gargiulo, et al. *The International Journal of Biochemistry & Cell Biology* 41:127-35 (2009); and Gronbaek, et al. *Basic Clin Pharmacol Toxicol* 103:389-96 (2008)).

Embodiments of the invention significantly advance the ability to map modified nucleotides in a genome to generate a map (methylome). A human methylome would facilitate studies on interpersonal phenotypic variations in whole organisms and in individual cells and can yield useful information on development, aging and disease. From this information, it may be possible to determine susceptibility for diseases such as cancer even before a pathology appears and to design appropriate treatments with the possibility of providing powerful diagnostic tests and therapeutic agents.

The identification of a family of enzymes with novel properties and the creation of novel oligonucleotide fragments permits a description of the status of the human methylome by allowing the isolation of a set or sets of oligonucleotide fragments that provide a concentration of modified bases found in the human genome. Isolation of the set(s) of fragments can be facilitated by gel electrophoresis, solid phase affinity-binding or other means. Methylome analysis can be aided by the addition of a control that may include treating the genome with M.SssI, which methylates substantially all CpG dinucleotides in the genome. (Yegnasubramanian et al. *Nucleic Acids Res* 34:e19 (2006)).

The set(s) of oligonucleotide fragments resulting from enzyme cleavage can be sequenced using high throughput sequencing methods of the sort that are currently available using NextGen sequencing methods to identify and map modified cytosine nucleotides in a DNA. This approach greatly simplifies the generation of a methylome for any large DNA or genome such as a mammalian genome. Selection of specific oligonucleotide cleavage products for rapid diagnostic methods to particular regions of the genome can determine the abnormal presence or absence of modified cytosines correlated with a disease such as cancer. Specific oligonucleotides may be used to determine a particular phenotype for an individual. For example, hybridization of a set of fragments to a defined sequence or set of sequences presented on a solid surface (array hybridization) or tagged in a solution (or visa versa) can reveal discrepancies with a standard set of fragments that characterize the methylome. qPCR or array hybridization may also be used to interrogate one or more known locations of interest for abundance. The modified nucleotide or binding molecule may be labelled with a fluorescent or chemiluminescent tag or other labelling methods known in the art to facilitate detection.

Modified nucleotides in the genome may be identified in situ using a mutant enzyme member of the newly defined family having an inactivated cleavage site. By visualizing the binding sites of the mutant enzyme, the location of the modified nucleotides can be determined.

The members of the newly defined family of enzymes may be genetically engineered so as to form recombinant proteins for large scale production. The purification of recombinant proteins may be facilitated by the formation of fusion proteins such that the enzyme is fused to an affinity tag which has an additional use. For example, if the tag is biotin, a His peptide, chitin-binding domain or maltose-binding protein or another substrate-binding domain, the member of the family may be isolated on an affinity matrix either directly itself acting as a methyl-binding domain or by binding to an antibody affinity matrix or by means of the affinity tag. The recombinant protein either alone, modified or fused to a tag may be fluorescently labeled for imaging purposes.

Where the enzyme kinetics are single turnover, low turnover or the enzyme lacks catalytic activity altogether, the enzyme or enzyme fusion protein while bound to a modified nucleotide-containing fragment may also be bound directly to an affinity matrix to separate the oligonucleotide fragments containing modified nucleotides from the remaining fragments for sequencing or for diagnostic tests.

The experimental protocols provided below in large part for MspJI are not intended to be limiting. One of ordinary skill in the art could employ the experimental design as provided below to any additional member of the newly defined family.

EXAMPLES

Example 1

Methylation-Specific DNA Cleavage Activity of MspJI Enzyme Family

Production of the Enzymes

Recombinant members of the MspJI enzyme family were expressed in dcm– strain ER2566 and purified until substantially homogeneous using multiple chromatography steps. The enzymes which had an N-terminal 8×His Tag were first purified on a HiTrap Heparin HP column (GE, Piscataway, N.J.), then a HisTrap HP column (GE, Piscataway, N.J.), and finally a HiTrap SP column (GE, Piscataway, N.J.). The purification procedure followed the manufacturer's recommendation. The cleavage activity of the enzyme fractions were assayed on lambda DNA (which is partially dcm-methylated). To further improve expression levels, the DNA encoding the enzymes can be codon-optimized.

Determining Cleavage Patterns of MspJI Enzyme Family by a Screening Assay

The assay may include one or more of the following steps:
1. Methylate a target nucleotide in a synthetic or naturally occurring large DNA optionally having a known sequence. For example, lambda DNA can be used which is partially dcm-methylated at CmCWGG sites and XP-12 phage genomic DNA whose cytosines are completely replaced by 5 mC cytosines.
2. React the large DNA with an MspJI enzyme family.
3. Size-separate the cleavage products for example using a polyacrylamide gel.
4. Sequence a set of oligonucleotide fragments of similar size to determine the position of the modified nucleotide; and
5. Optionally map the fragment sequence on the large DNA sequence.

An elaboration of step (1) includes using different large DNA preparations which have been reacted with different methyltransferases for modifying the DNA in vitro. These substrates are used to identify substrate specificities.

The products are analyzed by 1% agarose gel electrophoresis and can be visualized by ethidium bromide. For example, M.HpaII (NEB, Ipswich, Mass.) can produce CmCGG-modified DNA. Plasmid DNA-digestion can be monitored by 1% agarose gel electrophoresis and visualization using ethidium bromide staining. Alternatively, synthetic double-stranded oligonucleotide containing a modified site can be used in which any methylated sites can be easily created, independent of the availability of the methyltransferases. Modified nucleotides in palindromic sites of interest include for example, NmCGN, mCNG, NGmCN, GNmC etc., where N is A, T, G or C. In addition to fully-methylated oligonucleotides, oligonucleotides with hemi-methylated sites can be tested in this way. Other types of modification, such as 5-hydroxymethylated cytosine and 5-glucosylated-hydroxymethylated cytosine, can be either directly incorporated into the oligonucleotides during synthesis or by further modification of hydroxymethylated cytosine residues with bacteriophage T4 glucosyltransferase.

To determine cleavage sites, substrate oligonucleotides are labeled either at their 5' end or 3' end with $^{33}$P. Cleavage products are run on a 7M-urea 20% polyacrylamide denaturing gel to single nucleotide resolution and analyzed.

Characterizing MspJI Enzyme Family Members by an In Vivo Screening Assay

The ER1992 strain with endogenous methylase gene dcm, which methylates the inner cytosine in CCWGG sites to CmCWGG and serves as a target substrate for an enzyme with the desired cleavage activity, and ER2566, with a dcm– genotype with no 5-methyl cytosine and not subject to cleavage by a methylation-specific enzyme, were used to screen for methylation-specific activity of a novel recombinant restriction endonuclease.

Measuring the Activity of MsDJI Enzyme Family Members by an In Vitro Assay

A plasmid is used which contains only two methyl-C's separated by 1 kb of intervening sequence. This cleaves leaving three fragments, the plasmid backbone 3 kb, the insert 1 kb and the two 32 bp fragments. When this digest goes to completion, the uncut plasmid disappears and subsequent appearance of the 1 kb and backbone bands is easily quantifiable on an agarose gel. This plasmid is transformed into a dam–dcm– strain and purified as an assay substrate. Such plasmids are described in Stewart, F., et al. *Biological Chemistry* 379:611-616 (1998).

Determining Specificity of MspJI Enzyme Family Members for Modified Binding Sequences Versus Unmodified Binding Sequences Using an in Vitro Assay The in vitro activity of MspJI was assessed on a variety of methylated and non-methylated DNA substrates, as shown in FIG. 2A for the dcm-methylated plasmid DNA pBR322. MspJI showed endonuclease activity (FIG. 2A, Lanes 1 and 2) where this endonuclease activity was DNA methylation-dependent. In contrast, MspJI did not act on pBR322 without dcm-modification (FIG. 2A, Lanes 5 and 6). By using the restriction enzyme BstNI (CC↓WGG), which is insensitive to m5C methylation, in a double-digestion assay, cleavage sites on pBR322(dcm+) by MspJI were shown to be at or close to the dcm sites (FIG. 2A, Lanes 2, 3 and 4). The double digest did not alter the BstNI pattern, suggesting that MspJI did not cleave at non-BstNI sites.

In addition to the m5C-modified DNA tested above, MspJI did not exhibit endonuclease activity on M.TaqI-(TCGmA) or dam– (GmATC) methylated pBR322(dcm–) DNA. This confirmed that MspJI did not target m$^6$-adenine methylated DNA, consistent with the fact that the MspJI gene can be maintained and expressed in a dam+ strain (ER2566, NEB, Ipswich, Mass.). Moreover, MspJI does not apparently act on N$^4$-methylcytosine-containing plasmid DNA, as can be determined by using M.BstNI (CCWGG, a N4-cytosine methylase) methylated DNA.

Assaying Activity of MspJI Enzyme Family Members on DNA Substrates Which Contain 5-Hydroxymethylcytosine or 5-Glucosyl-Hydroxymethylcytosine Wild-type T4 phage DNA with glucosylated cytosines and the DNA from a T4 α gt57 β gt14 (a mutant which has defective glucosyltransferases and therefore contains hydroxymethylated cytosines in DNA hereafter T4gt) were used as substrates (FIG. 2C, Lanes 1 and 2). MspJI was able to degrade T4 gt DNA (FIG. 2C, Lanes 8-11) and was inactive on glucosylated DNA (FIG. 2C, Lane 7). For comparison, activity of another modification-dependent endonuclease, McrBC (FIG. 2C, Lanes 3 and 4) and a typical type IIP restriction enzyme MspI (FIG. 2C, Lanes 5 and 6) with these modified DNA substrates were shown. McrBC, which recognizes pairs of (A/G)$^m$C separated by 40~3000 base pairs, also exhibited nuclease activity on the hydroxymethylcytosine-containing DNA but not on T4 wild-type DNA, while MspI was inactive with respect to both substrates. Note that MspJI was able to degrade T4 gt DNA to a greater extent than McrBC, which can be explained by its broader recognition sequence than McrBC. Overall, it appears that MspJI specifically targets cytosine-modified DNA with 5-$CH_3$ or 5-$CH_2OH$ addition on the pyrimidine ring.

Determining Substrate Sequences Around a Cleavage Site

MspJI-digested DNA samples with different methylated sites were subjected to capillary sequencing and the cleavage sites were deduced from the location at which peaks are reduced in height near the methylated sites in the sequencing chromatograms (examples shown in FIG. 5). Positions of cleavage occur at locations where the sequence signals (peaks) are reduced in height. In many cases, a non-templated adenine is added as the polymerase runs off the DNA, and location of such a "runoff peak" adenine is additional evidence for the location of cleavage. One observation on the sequencing chromatogram data was that cleavage sites occur at a site distant from the methylated sites. FIG. 5 also displays the deduced cleavage pattern of MspJI on different methylated sites. Another observation was that the height reduction in sequencing peaks and addition of adenine not present in the substrate were generally present on both sides of the methylated sites. The response in the chromatogram on both sides demonstrated that MspJI cleaved the DNA each side of the methylated binding sequence. This is consistent with the symmetry of the methylated binding sites. The presence of two run-off peaks is evidence for two independent cleavage events on the same strand.

It was concluded that MspJI recognized the m5C on one strand and then cut 12 nucleotides 3' downstream on the same strand and 16 nucleotides downstream on the complementary strand to leave a 4-base 5' overhang. Similarly, when the m5C on the complementary strand was recognized, the same pattern of cleavage was observed demonstrating that two double-stranded breaks around the same recognition site released the fragment with the methylated site in the middle. The exact length of that fragment depended on the distance between the methyl groups on the two strands. In the case of HpaII methylated sites (Cm5CGG) or HhaI methylated sites (Gm5CGC), the length of the fragment excised from the DNA substrate was expected to be 32 nucleotides including the two 4-base 5' overhangs.

Comparing the Activity of an MspJI Enzyme Family Members on Fully-Methylated and Hemi-Methylated DNA To investigate whether MspJI is active on hemi-methylated DNA substrates, which can arise during replication, FAM-labeled synthetic substrates were used in a digestion assay (FIG. 4A). FIG. 4A indicates the expected cleavage sites and product sizes and FIG. 4B shows the digestion reactions resolved on a 7M urea 20% polyacrylamide denaturing gel. The m5C for interrogation is at an M.HpaII site (CmCGG) in the oligos. Null-methylation, full-methylation, hemi-methylation on the top strand or bottom strand were tested and the cleavage events on the top strand and bottom strands were observed by labeling them individually, as shown in FIG. 4B.

On fully-methylated DNA, MspJI makes cuts on both sides of the methylated site. On the top strand, it cleaves on either side of the methylated site, resulting in 40 bp (from cut Lt) and 11 or 12 bp (from cut Rt) fragments (FIG. 4B, Lane 3). Symmetrically, on the bottom strand, it cleaves twice and generates a long fragment of 36 nt (from cut Lb) and a shorter fragment of 7 or 8 nt (from cut Rb) (FIG. 4B, Lane 4).

On the hemi-methylated substrates, strand methylation status dictates the side of the cleavage, so that double-stranded breaks only occur on the 3' side of the strand containing the methylated base. For example, for substrate with only top strand methylation, each cleavage event is at the 3' side of the 5 mC so that only shorter fragments are observed (FIG. 4B, Lanes 5 and 6). The same applies to the substrate with bottom strand methylation where only longer fragments are seen (FIG. 4B, Lanes 7 and 8). The results show that each m5C is associated with two cuts on the same side and such association is symmetrical. Thus, while not wishing to be bound by theory, it is proposed that MspJI recognizes each half of the methylated site separately in a fully-methylated site, either the top or the bottom strand, and that the half site then dictates the directionality of the cleavage.

Characterizing the MspJI Enzyme Family Members with Shared Conserved DNA Sequences, Secondary Sequence Motifs, and Binding and Cleavage Properties By using the amino acid sequence of a member of the MspJI family such as MspJI as the query sequence, a PSI-BLAST search (Altschul et al., *Nucleic Acids Res* 25:3389-3402 (1997)) against GenBank retrieved more than 100 hits with significant sequence homology. Sixteen genes among the top hits had significant similarity to MspJI throughout the sequence length. In FIG. 1D, a partial multiple sequence alignment is provided around the conserved catalytic motif inside the MspJI subfamily. The significance of the conserved catalytic motif is shown by the site-directed mutagenesis experiments, in which both D334A and Q355A mutations completely abolish the catalytic activity of MspJI.

The predicted secondary structure elements of the MspJI family were determined using multiple sequence alignment created by PROMALS webserver (Pei et al. *Nucleic Acids Res* 35:W649-652 (2007)) (FIG. 1B shows a schematic and FIGS. 7-1 to 7-7 the full alignment). The structure core of the catalytic C-terminal domain has three consecutive strands ($\beta1\beta2\beta3$ in FIG. 1B), with the motif (Q/E)xK at the end of $\beta3$ and the conserved residue D at the beginning of $\beta2$ (FIGS. 7-1 to 7-7) (Wah et al. *Proc Natl Acad Sci USA* 95:10564-10569 (1998)). The two helices and strands in the order of $\alpha4$-$\beta4$-$\alpha5$-$\beta5$ after $\beta1\beta2\beta3$ forms an interaction interface between monomers (FIG. 1B).

Determining the Role of an Activator in Improving Cleaving Activity of Members of the Newly Defined Family of Enzymes An activator dimer containing double-stranded 5-methyl cytosine (e.g., 11mer, 15-mer, 19mer and 23mer) are tested to determine whether digestion by members of the MspJI enzyme family can be enhanced. These dimers are constructed by annealing two single strand oligonucleotides or by hairpin formation of a single oligonucleotide.

The assay for the activator includes constructing self-complementary oligonucleotides containing 5-methyl-C's at the center of various lengths. Oligonucleotides are biotinylated at the 5' end for subsequent removal from reactions and 3' amino-modified such that they cannot be ligated or extended. The activators are then assayed for their abilities to enhance cleavage before and after streptavidin bead removal for interference in sequencing.

Example 2

Demonstration of the Application of Enzymes in Mapping the Methylome

To analyze the methylome analysis of a mouse or a human genome, 1-2 µgs of human or mouse genomic DNA is used for the methylome analysis at single nucleotide resolution. The genome is digested with a member of the MspJI family optionally in the presence of biotin-containing activator molecules, followed by removal of activator molecules using streptavidin magnetic affinity beads. The digested DNA is end-repaired using the NEBNext™ (NEB, Ipswich) end-repair module, ethanol-precipitated and dissolved in a suitable volume of water. The digested genomic DNA is ligated to bar-coded SOLiD primer and P1 primer using NEBNext™ quick ligation module (NEB, Ipswich, Mass.). The ligated product is separated on a 10% TBE polyacrylamide gel and the ligated product of ~110 bps (between 100-130 bp) is excised after visualization by ethidium bromide staining. A crush and soak or a suitable elution method is used to isolate DNA for SOLiD sequencing (Applied Biosystems, Inc., Life Technologies, Inc., Carlsbad, Calif.). MspJI for example does not distinguish between methylated and hydroxymethylated cytosine residues for cleavage, thus the sequencing data will result in analysis of the whole methylome.

Determination of the Biological Role of 5-Hydroxy Methylcytosine in Mammals

The dynamic changes of DNA methylation during mouse embryonic stem cell (ES) differentiation can be identified using the newly defined family of enzymes. Previous reports suggest that as much as 10% of the modified cytosines are in the form of 5-hydroxymethylcytosine. These will have been missed using current methodologies involving bisulfite. This modified adduct is complementary to guanine and is read as cytosine in polymerase-based amplification.

Exploration of Methylomes of Other Model Organisms.

The MspJI enzyme family not only acts on mCpG, but is capable of recognizing and cleaving other types of methylated sites. For example, mCNG, which is present in the genomic DNA of *Arabidopsis*, is a natural substrate for MspJI. This provides a simple method of assaying for the presence of modified bases in any organism. For instance, digestion of total genomic DNA with MspJI gives a 32 bp fragment that is easy to isolate from a polyacrylamide gel. It can then be digested to mononucleotides using a standard cocktail of enzymes and the total digest examined by HPLC and/or mass spectrometry to identify the modified bases. A variety of organisms such as *Arabidopsis, Xenopus*, zebrafish, chicken, *Neurospora crassa* as well as genomes known to contain unusual modifications like Base J found in kinetoplastid protozoans such as *Trypanosomes* (Cross et al. *EMBO J.* 18:6573-6581 (1999)) is studied by the methods described herein. Once an epigenome is confirmed, the digested bands can be sent for high throughput sequencing using the established protocols for human.

TABLE 1

Genomic context analysis of the MspJI subfamily

| # | Gene ID | Genbank ID | Close to methylase? | Species | Additional notes | Activity on 5 mC DNA* |
|---|---|---|---|---|---|---|
| 1 | MspJI | YP_001069123 | Y | *Mycobacterium* sp. JLS | close to M and V genes | Y |
| 2 | Sbal195_0369 | YP_001552810 | Y | *Shewanella baltica* OS195 | 2 ORFs from M gene | N/T |
| 3 | PE36_01892 | ZP_01896882 | Y | *Moritella* sp. PE36 | SAM-dependent methylase | N/T |
| 4 | Spea_3849 | YP_001503694 | N | *Shewanella pealeana* ATCC 700345 | | N |
| 5 | Xcc3577 | NP_638923 | N | *Xanthomonas campestris* ATCC 33913 | Among transposase islands | N |
| 6 | Lhv_0031 | YP_001576608 | N | *Lactobacillus helveticus* DPC 4571 | Among transposase islands | N |
| 7 | Lpg1234 | YP_095265 | Y | *Legionella pneumophila* strain Philadelphia 1 | Close to R and M genes; M gene is active. | Y |
| 8 | Franean1_5336 | YP_001509600 | N | *Frankia* sp. EAN1pec | Standalone | Y |
| 9 | CATMIT_00196 | ZP_03681584 | N/A | *Catenibacterium mitsuokai* DSM 15897 | Unfinished genome sequence | N/T |
| 10 | Rmet_0004 | YP_582159 | N | *Ralstonia metallidurans* CH34 | Standalone | N |
| 11 | Bcenmc03_0011 | YP_001763314 | Y | *Burkholderia cecepacia* MC0-3 | Close to M and V genes | N/T |
| 12 | AspBH1 | YP_931859 | Y | *Azoarcus* sp. BH72 | Close to M and V genes | Y |
| 13 | RlaI | ZP_03168528 | N | *Ruminococcus lactaris* ATCC 29176 | Close to V gene | Y |
| 14 | Xccb100_0619 | YP_001902024 | N | *Xanthomonas campestris* strain B100 | Among transposase islands | N/T |
| 15 | ZP_03855940 | ZP_03855940 | Y | *Veillonella parvula* DSM 2008 | Close to M gene | N |

TABLE 2

Similarity and identity of sequences in the family

| | similarity | | | | | | | |
|---|---|---|---|---|---|---|---|---|
| identity | AspBHI | Bcenmc03_0011 | CATMIT_00196 | Franean1_5336 | MspJI | PE36_01892 | RlaI | Rmet_0004 |
| AspBHI | 100/100 | 36.5/47.4 | 41.3/57.7 | 40.1/52.4 | 25.6/38.0 | 22.8/38.3 | 42.2/58.0 | 38.6/52.7 |
| Bcenmc03_0011 | 36.5/47.4 | 100/100 | 30.8/43.6 | 27.9/40.6 | 18.9/28.7 | 16.7/29.8 | 32.8/45.9 | 33.4/47.4 |
| CATMIT_00196 | 41.3/57.7 | 30.8/43.6 | 100/100 | 35.9/51.1 | 20.2/37.1 | 24.7/41.2 | 40.9/61.8 | 33.1/47.3 |
| Franean1_5336 | 40.1/52.4 | 27.9/40.6 | 35.9/51.1 | 100/100 | 22.3/34.5 | 23.2/37.0 | 36.6/51.7 | 35.9/46.7 |
| MspJI | 25.6/38.0 | 18.9/28.7 | 20.2/37.1 | 22.3/34.5 | 100/100 | 36.5/53.4 | 23.1/40.2 | 22.6/35.3 |

TABLE 2-continued

Similarity and identity of sequences in the family

| | | | | | | | | |
|---|---|---|---|---|---|---|---|---|
| PE36_01892 | 22.8/38.3 | 16.5/29.1 | 24.7/41.2 | 23.2/37.0 | 36.5/53.4 | 100/100 | 21.6/36.8 | 24.1/36.7 |
| RlaI | 42.3/58.2 | 32.8/45.9 | 40.9/61.8 | 36.6/51.7 | 23.1/40.2 | 21.6/36.8 | 100/100 | 38.0/53.4 |
| Rmet_0004 | 38.6/52.7 | 32.3/48.5 | 33.1/47.3 | 35.5/46.5 | 22.5/36.6 | 24.0/37.7 | 38.0/53.4 | 100/100 |
| Sbal195_0369 | 22.6/36.7 | 16.4/28.8 | 24.7/42.0 | 22.8/35.0 | 36.3/54.4 | 73.8/83.3 | 24.3/41.3 | 24.1/35.1 |
| SgriT_16873 | 45.7/60.9 | 30.2/42.8 | 37.0/55.4 | 52.1/64.2 | 25.4/39.8 | 26.4/40.6 | 41.3/57.7 | 37.4/50.8 |
| Spea_3849 | 21.5/35.2 | 17.5/29.7 | 24.8/43.5 | 23.6/36.3 | 34.3/53.9 | 70.6/81.7 | 23.9/42.0 | 24.2/35.2 |
| Xcc3577 | 24.2/37.9 | 19.6/30.2 | 25.7/38.7 | 22.4/32.0 | 38.2/51.5 | 40.9/60.0 | 21.5/39.5 | 22.6/36.7 |
| gi\|227372459\|ref\|ZP_03855940.1\| V. par | 39.1/58.0 | 29.6/44.8 | 42.3/60.6 | 31.9/47.7 | 22.2/41.2 | 24.8/39.7 | 42.3/59.9 | 34.8/49.2 |
| gi\|260101829 DSM 20075 | 22.2/36.1 | 19.4/34.6 | 22.3/39.1 | 21.4/30.3 | 29.2/43.6 | 34.6/50.9 | 24.1/38.0 | 23.8/39.2 |
| lhv_0031 | 21.3/34.8 | 17.3/30.8 | 23.2/40.7 | 21.7/31.0 | 30.4/46.0 | 36.3/53.5 | 24.8/40.0 | 21.5/34.9 |
| lpg1234 | 42.6/62.9 | 28.4/43.8 | 37.8/57.0 | 37.0/52.4 | 21.3/37.8 | 26.1/40.9 | 41.6/58.7 | 49.3/62.1 |

| | | | | | similarity | | | |
|---|---|---|---|---|---|---|---|---|
| identity | Sbal195_0369 | SgriT_16873 | Spea_3849 | Xcc3577 | gi\|227372459\|ref\|ZP_03855940.1\| V. par | gi\|260101829 DSM 20075 | lhv_0031 | lpg1234 |
| AspBHI | 22.6/36.7 | 45.7/60.9 | 21.5/35.2 | 24.2/37.9 | 39.1/58.0 | 22.2/36.1 | 21.3/34.8 | 42.6/62.9 |
| Bcenmc03_0011 | 16.4/28.8 | 30.2/42.8 | 17.5/29.7 | 19.6/30.2 | 29.6/44.8 | 19.4/34.6 | 17.3/30.8 | 28.4/43.8 |
| CATMIT_00196 | 24.7/42.0 | 37.0/55.4 | 24.8/43.5 | 25.7/38.7 | 42.3/60.6 | 22.3/39.1 | 23.2/40.7 | 37.8/57.0 |
| Franean1_5336 | 22.8/35.0 | 52.1/64.2 | 24.0/36.3 | 22.4/32.0 | 31.9/47.7 | 21.4/30.3 | 21.7/31.0 | 37.0/52.4 |
| MspJI | 36.3/54.4 | 25.4/39.8 | 34.3/53.9 | 38.2/51.5 | 22.2/41.2 | 29.2/43.6 | 30.4/46.0 | 21.3/37.8 |
| PE36_01892 | 73.8/83.3 | 26.2/40.4 | 70.6/81.7 | 40.9/60.0 | 24.8/39.7 | 34.6/50.9 | 36.3/53.5 | 26.1/40.9 |
| RlaI | 24.3/41.3 | 41.3/57.7 | 23.9/42.0 | 22.2/40.2 | 42.5/60.1 | 24.1/38.0 | 24.8/40.0 | 41.6/58.7 |
| Rmet_0004 | 24.1/35.1 | 37.1/50.4 | 24.2/35.2 | 22.6/36.7 | 34.8/49.2 | 23.8/39.2 | 21.5/34.9 | 49.3/62.1 |
| Sbal195_0369 | 100/100 | 24.0/36.5 | 86.5/93.1 | 40.6/60.7 | 22.9/40.7 | 36.0/50.1 | 38.6/54.9 | 25.1/41.3 |
| SgriT_16873 | 24.0/36.5 | 100/100 | 25.4/38.2 | 23.2/32.7 | 38.8/56.1 | 23.7/36.4 | 25.3/38.4 | 44.3/60.1 |
| Spea_3849 | 86.5/93.1 | 25.4/38.2 | 100/100 | 39.9/58.9 | 24.7/42.7 | 35.1/49.8 | 36.5/53.0 | 23.5/38.0 |
| Xcc3577 | 40.6/60.7 | 23.2/32.7 | 39.9/58.9 | 100/100 | 21.2/38.2 | 31.5/48.5 | 33.1/51.6 | 19.8/39.0 |
| gi\|227372459\|ref\|ZP_03855940.1\| V. par | 22.9/40.7 | 38.8/56.1 | 24.7/42.7 | 21.2/38.2 | 100/100 | 100/100 | 23.9/40.7 | 42.0/60.9 |
| gi\|260101829 DSM 20075 | 36.0/50.1 | 23.9/36.6 | 35.1/49.8 | 31.5/48.5 | 100/100 | 100/100 | 88.2/88.2 | 21.3/35.6 |
| lhv_0031 | 38.6/54.9 | 25.5/38.5 | 36.5/53.0 | 33.1/51.6 | 23.9/40.7 | 88.2/88.2 | 100/100 | 23.2/38.7 |
| lpg1234 | 25.1/41.3 | 44.3/60.1 | 23.5/38.0 | 19.8/40.4 | 42.0/60.9 | 21.3/35.6 | 23.2/38.7 | 100/100 |

What is claimed is:

1. A composition comprising a plurality of similar sized double-stranded fragments, the fragments further characterized by:
   (a) staggered ends; and
   (b) a centrally positioned methylated or hydroxymethylated cytosine proximal to a guanine;
   wherein the fragments are obtainable by in vitro enzymatic cleavage of a large DNA, the large DNA comprising genomic DNA.

2. The composition according to claim 1, wherein plurality of fragments are isolated.

3. The composition according to claim 1, wherein the large DNA is at least 100 nucleotides in length.

4. The composition according to claim 1, wherein the large DNA is a mammalian genomic DNA.

5. The composition according to claim 1, wherein the large DNA is human genomic DNA.

6. The composition according to claim 1, wherein the fragments are less than 60 nucleotides in size.

7. The composition according to claim 6, wherein the fragments have a similar size in the range of 28-36 nucleotides.

8. The composition according to claim 1, wherein the centrally positioned methylated or hydroxymethylated cytosine is located within 30 nucleotides from one end of the fragments.

9. The composition according to claim 1, wherein the centrally positioned methylated or hydroxymethylated cytosine and guanine are in a CpG dinucleotide.

10. The composition according to claim 1, wherein the centrally positioned methylated or hydroxymethylated cytosine and guanine are in a CNG trinucleotide.

* * * * *

SEQUENCE LISTING

<160> NUMBER OF SEQ ID NOS: 58

<210> SEQ ID NO 1
<211> LENGTH: 53
<212> TYPE: DNA
<213> ORGANISM: artificial
<220> FEATURE:
<223> OTHER INFORMATION: oligonucleotide

<400> SEQUENCE: 1
tggtaataat aaggttgagg acttttccg gatgcccgga atgggttcaa agg      53

<210> SEQ ID NO 2
<211> LENGTH: 76
<212> TYPE: DNA
<213> ORGANISM: artificial
<220> FEATURE:
<223> OTHER INFORMATION: synthetic construct
<220> FEATURE:
<221> NAME/KEY: misc_feature
<222> LOCATION: (67)..(67)
<223> OTHER INFORMATION: n is a, c, g, or t

<400> SEQUENCE: 2
gcaagaggcc cggcagtacc ggcataacca agcctatgcm tacagcatcc agggtgacgg      60
tgccgangat gacgat                                                        76

<210> SEQ ID NO 3
<211> LENGTH: 63
<212> TYPE: DNA
<213> ORGANISM: artificial
<220> FEATURE:
<223> OTHER INFORMATION: synthetic construct
<220> FEATURE:
<221> NAME/KEY: misc_feature
<222> LOCATION: (27)..(33)
<223> OTHER INFORMATION: n is a, c, g, or t
<220> FEATURE:
<221> NAME/KEY: misc_feature
<222> LOCATION: (36)..(42)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (54)..(55)
<223> OTHER INFORMATION: n is a, c, g, or t
<220> FEATURE:
<221> NAME/KEY: misc_feature
<222> LOCATION: (57)..(61)
<223> OTHER INFORMATION: n is a, c, g, or t

<400> SEQUENCE: 3
gcagcggtcg ggctgaacgg ggggttnnnn nnnacnnnnn nncttgnann gaannannnn        60 nac                                                                     63

<210> SEQ ID NO 4
<211> LENGTH: 71
<212> TYPE: DNA
<213> ORGANISM: artificial
<220> FEATURE:
<223> OTHER INFORMATION: synthetic construct
<220> FEATURE:
<221> NAME/KEY: misc_feature
<222> LOCATION: (24)..(24)
<223> OTHER INFORMATION: n is a, c, g, or t

<400> SEQUENCE: 4
gatcaaagga tcttcttgag atcnttttttt tctgcgcgta atctgctgct trcaaacaaa       60
aaaaccaccg c                                                            71

<210> SEQ ID NO 5
<211> LENGTH: 73
<212> TYPE: DNA
<213> ORGANISM: artificial
<220> FEATURE:
<223> OTHER INFORMATION: synthetic construct

<400> SEQUENCE: 5
gcacaacatg ggggatcatg taactcgcct tgatmgttgg gaaccggagc tgaatgaagc        60
mataccaaac gac                                                          73

<210> SEQ ID NO 6
<211> LENGTH: 66
<212> TYPE: DNA
<213> ORGANISM: artificial
<220> FEATURE:
<223> OTHER INFORMATION: synthetic construct
<220> FEATURE:

```
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t

<400> SEQUENCE: 6
ccacgggtgc gcntaatcgt gctcctgtmg ttgnggaccc ggctaggctg gcggggttgc      60
cttact                                                                66

<210> SEQ ID NO 7
<211> LENGTH: 390
<212> TYPE: PRT
<213> ORGANISM: Veillonella parvula

<400> SEQUENCE: 7
```

| Met | Ile | Ser | Phe | Lys | Asp | Val | Cys | Glu | Thr | Glu | Val | Asp | Leu | Val | Ile |
|---|---|---|---|---|---|---|---|---|---|---|---|---|---|---|---|
| 1 | | | | 5 | | | | | 10 | | | | | 15 | |

| Asp | Glu | Ile | Tyr | Glu | Gly | Gly | Ala | Val | Gly | Asn | Ile | Leu | Asp | Asp | Val |
|---|---|---|---|---|---|---|---|---|---|---|---|---|---|---|---|
| | | | 20 | | | | | 25 | | | | | 30 | | |

| Leu | Thr | Lys | Leu | Met | Gly | Val | Gln | Asn | Ala | Gly | Gly | Phe | Arg | Tyr | Arg |
|---|---|---|---|---|---|---|---|---|---|---|---|---|---|---|---|
| | | 35 | | | | | 40 | | | | | 45 | | | |

| Asn | Val | Leu | Asn | Thr | Thr | Asp | Lys | Ala | Tyr | Ile | Val | Leu | Tyr | Ser | Ser |
|---|---|---|---|---|---|---|---|---|---|---|---|---|---|---|---|
| | 50 | | | | | 55 | | | | | 60 | | | | |

| Asn | Glu | Asp | Ile | Asp | Trp | Pro | Asp | Val | Leu | Glu | Ala | Glu | Thr | Gly | Lys |
|---|---|---|---|---|---|---|---|---|---|---|---|---|---|---|---|
| 65 | | | | | 70 | | | | | 75 | | | | | 80 |

| Phe | Lys | Tyr | Tyr | Gly | Asp | Asn | Lys | Arg | Pro | Gly | Asp | Lys | Val | Asp | Ser |
|---|---|---|---|---|---|---|---|---|---|---|---|---|---|---|---|
| | | | | 85 | | | | | 90 | | | | | 95 | |

| Lys | Lys | Gly | Asn | Leu | Ile | Leu | Glu | Thr | Ile | Phe | Asn | Glu | Lys | Asn | Arg |
|---|---|---|---|---|---|---|---|---|---|---|---|---|---|---|---|
| | | | 100 | | | | | 105 | | | | | 110 | | |

| Asn | Lys | Ile | Pro | Pro | Val | Phe | Ile | Phe | Met | Lys | Asn | Pro | Thr | Val | Ala |
|---|---|---|---|---|---|---|---|---|---|---|---|---|---|---|---|
| | | 115 | | | | | 120 | | | | | 125 | | | |

| Ser | Asn | Arg | Ser | Val | Arg | Phe | Leu | Gly | Leu | Ala | Val | Pro | Glu | Asp | Tyr |
|---|---|---|---|---|---|---|---|---|---|---|---|---|---|---|---|
| | 130 | | | | | 135 | | | | | 140 | | | | |

| Tyr | Leu | Gly | Lys | Asp | Asn | Ser | Leu | Lys | Ala | Ile | Trp | Arg | Thr | Ser | Asn |
|---|---|---|---|---|---|---|---|---|---|---|---|---|---|---|---|
| 145 | | | | | 150 | | | | | 155 | | | | | 160 |

| Ser | Glu | Arg | Phe | Ile | Asn | Tyr | Glu | Ala | His | Phe | Thr | Ile | Leu | Asn | Thr |
|---|---|---|---|---|---|---|---|---|---|---|---|---|---|---|---|
| | | | | 165 | | | | | 170 | | | | | 175 | |

| Lys | Ser | Ile | Asn | Arg | Glu | Trp | Leu | Ser | Cys | Leu | Ile | Asn | Gly | Asp | Ser |
|---|---|---|---|---|---|---|---|---|---|---|---|---|---|---|---|
| | | | 180 | | | | | 185 | | | | | 190 | | |

| Leu | Asn | Thr | Arg | Phe | Ala | Pro | Asp | Ala | Trp | Leu | Lys | Tyr | Val | Lys | Gln |
|---|---|---|---|---|---|---|---|---|---|---|---|---|---|---|---|
| | | 195 | | | | | 200 | | | | | 205 | | | |

| Gly | Leu | Thr | Asp | Asp | Ile | Ile | Leu | Ser | Ala | Pro | Lys | Asn | Lys | Glu | Tyr |
|---|---|---|---|---|---|---|---|---|---|---|---|---|---|---|---|
| | 210 | | | | | 215 | | | | | 220 | | | | |

| Arg | Ser | Lys | Ile | Glu | Gln | Leu | Pro | Ser | Thr | Asp | Lys | Asp | Leu | Arg | Lys |
|---|---|---|---|---|---|---|---|---|---|---|---|---|---|---|---|
| 225 | | | | | 230 | | | | | 235 | | | | | 240 |

| Leu | Asp | Phe | Ile | Tyr | Gln | Tyr | Tyr | Lys | Asp | Glu | Pro | Tyr | Lys | Phe | Glu |
|---|---|---|---|---|---|---|---|---|---|---|---|---|---|---|---|
| | | | | 245 | | | | | 250 | | | | | 255 | |

| Tyr | Phe | Ala | Ala | Lys | Leu | Val | Gly | Leu | Met | Asp | Asn | Asn | Phe | Leu | Asn |
|---|---|---|---|---|---|---|---|---|---|---|---|---|---|---|---|
| | | | 260 | | | | | 265 | | | | | 270 | | |

| Phe | Asn | Ile | Thr | Arg | Thr | Val | Arg | Asp | Gly | Gly | Ile | Asp | Ala | Ile | Gly |
|---|---|---|---|---|---|---|---|---|---|---|---|---|---|---|---|
| | | 275 | | | | | 280 | | | | | 285 | | | |

| Glu | Tyr | Arg | Leu | Gly | His | Lys | Asn | Asn | Ser | Ile | Lys | Leu | Arg | Cys | Ala |
|---|---|---|---|---|---|---|---|---|---|---|---|---|---|---|---|
| | 290 | | | | | 295 | | | | | 300 | | | | |

| Leu | Glu | Ala | Lys | Cys | Tyr | Gln | Arg | Asp | Asn | Ser | Asn | Gly | Val | Lys | Leu |

```
                305                 310                 315                 320
Leu Ser Arg Leu Ile Ser Arg Leu Lys Tyr Arg Asp Phe Gly Ile Phe
                    325                 330                 335

Val Thr Thr Ser Tyr Val Ser Glu Gln Ala Tyr Lys Glu Leu Leu Glu
                    340                 345                 350

Asp Gly His Pro Val Ile Ile Ile Ser Gly Gly Asp Ile Ile Glu Ile
                    355                 360                 365

Leu Thr Asn Asn Arg Ile Asn Thr Lys Glu Ser Leu Leu Asn Phe Met
                    370                 375                 380

Asp Thr Ile Asp Tyr Leu
385                 390

<210> SEQ ID NO 8
<211> LENGTH: 405
<212> TYPE: PRT
<213> ORGANISM: Catenibacterium mitsuokai

<400> SEQUENCE: 8

Met Val Glu Val Ala Phe Glu Asp Leu Gln Asn Ala Asp Leu Gln Ile
1               5                   10                  15

Gly Cys Val Tyr Lys Gly Gly Thr Ala Pro Asn Leu Gly Ser Asp Pro
                20                  25                  30

Leu Ser His Leu Phe Pro Cys Gly Asn Ala Gly Gly Phe Arg Arg Val
            35                  40                  45

Asn Arg Arg Asp Gly Ser Arg Leu Pro Ala Tyr Val Ile Leu Tyr Thr
        50                  55                  60

Ser Met Glu Glu Leu Glu Trp Pro Asp Phe Leu Asp Glu Glu Thr Gly
65                  70                  75                  80

Val Phe Arg Tyr Tyr Gly Asp Asn Arg Lys Pro Gly Asn Asp Ile Arg
                85                  90                  95

Asn Thr Lys Lys Lys Gly Asn Leu Leu Leu Glu Glu Val Phe Glu Leu
                100                 105                 110

Leu Asn Ser Asn Asn Leu Glu Asp Met Pro Pro Phe Phe Val Phe Lys
            115                 120                 125

Lys Thr Gly Asn Gly Arg Asp Ile Gln Phe Leu Gly Leu Ala Ala Pro
        130                 135                 140

Gly Asn Ser Asn Ile Ser Pro Gly Arg Asp Leu Val Ala Leu Trp Cys
145                 150                 155                 160

Ser Leu Asn Gly Gln Lys Phe Gln Asn Tyr Glu Ala Tyr Phe Thr Ile
                165                 170                 175

Leu Asp Thr Lys Gly Lys Gly Ile Ser Arg Asp Trp Ile Lys Ser Leu
            180                 185                 190

Ser Glu Asp His Ser Ala Ser Ile Asp Val Ala Pro Asp Val Trp Lys
        195                 200                 205

Lys Phe Ile Ser Gln Gly Arg Asp Gly Ile Glu Ala Leu Lys Ala Pro
210                 215                 220

Lys Ile Ile His Ile Pro Ser Lys Cys Asp Gln Leu Gln Cys Asp Asp
225                 230                 235                 240

Glu Gly Lys Lys Cys Val Asp Ala Ile Arg Glu His Tyr Lys Asp Asn
                245                 250                 255

Pro Tyr Gly Phe Glu Ser Cys Ala Met Asp Leu Leu Met Lys Met Asp
            260                 265                 270

Asn His Phe Val Asp Phe Asn Leu Thr Arg Pro Trp Arg Asp Gly Gly
        275                 280                 285

Arg Asp Ser Ile Gly Tyr Tyr Ser Ile Asn Ser Gly Gly Lys Val Asn
```

```
            290                 295                 300
Ala Pro Leu Lys Ile Asp Cys Ala Leu Glu Ala Met Cys Tyr Ala Glu
305                 310                 315                 320

Thr Asn Gly Ile Gly Ile Lys Gln Met Ser Arg Leu Ile Ser Arg Ile
                325                 330                 335

Arg Tyr Arg Gln Phe Gly Ile Leu Ile Thr Thr Ser Tyr Val Asp Glu
                340                 345                 350

Gln Ala Tyr Gln Glu Val Val Glu Asp Gly His Pro Ile Leu Val Val
                355                 360                 365

Thr Ala Thr Asp Ile Ala Arg Ile Leu Arg Ile Asn Ser Ile Thr Ser
        370                 375                 380

Glu Asn Ile Asp Glu Tyr Leu Asn Ser Ile Asp Ser Arg Arg Lys Glu
385                 390                 395                 400

Trp Glu Gln Asp Lys
                405

<210> SEQ ID NO 9
<211> LENGTH: 450
<212> TYPE: PRT
<213> ORGANISM: Frankia sp.

<400> SEQUENCE: 9

Met Gln Ser Thr Gly Val Arg Pro Cys Pro Leu Ala Ser Val Ala Val
1               5                   10                  15

Ala Thr Glu Val Ala Thr Pro Gly Gly Ala Ser Asp Ala Arg Cys Leu
                20                  25                  30

Asp Glu Pro Ser Ser Gly Leu Gly Ser Leu Arg Ala Val Asp Asp Lys
            35                  40                  45

Ser Gln Val Val Pro Phe Val Asp Leu Pro Thr Ala Ala Leu Val Val
    50                  55                  60

Asp Gln Leu Tyr Glu Gly Gly Thr Ala Gly Thr Leu Ala Asp Asp Pro
65              70                  75                  80

Leu Ala Arg Leu Leu Pro Val Gly Asn Gln Gly Gly Phe Arg Tyr Ala
                85                  90                  95

Gly Ser Pro Arg Lys Gly Thr Val Arg Leu Ser Val Leu Tyr Thr Thr
            100                 105                 110

Gly Ala Val Ala Asp Trp Pro Asp Thr Leu Asp Pro Ser Thr Gly Val
        115                 120                 125

Phe Thr Tyr Tyr Gly Asp Asn Arg Lys Pro Gly Arg Asp Leu His Asp
130                 135                 140

Thr Gln Arg Ser Gly Asn Leu Leu Leu Arg Asp Val Phe Glu His Ala
145                 150                 155                 160

His Gly Ser Val Glu Glu Arg Arg Thr Val Pro Pro Phe Leu Leu Phe
                165                 170                 175

Glu Thr Ala Pro Pro Gly Arg Arg Ile Met Phe Arg Gly Leu Leu Ala
            180                 185                 190

Pro Gly Ala Ala Thr Leu Thr Ser Asp Asp Leu Val Ala Ile Trp
        195                 200                 205

Arg Asn Thr Arg Gly His Arg Phe Gln Asn Tyr Arg Ala His Phe Thr
210                 215                 220

Val Leu Asp Val Ala Thr Val Thr Arg Thr Trp Leu Thr Asp Ile Leu
225                 230                 235                 240

Ala Gly His Ala Thr Asp Ser Glu His Cys Pro Pro Ala Trp Thr Ala
                245                 250                 255

Trp Val Asp Gly Arg Ala Tyr Ser Pro Leu Ile Ala Pro Ser Thr Thr
```

```
                260                 265                 270
Ile Ile Arg Thr Lys Ala Glu Gln Gln Pro Pro Asp Pro Thr Gly Val
        275                 280                 285

Ala Ile Leu Ala Ala Ile Arg Glu His Tyr Arg Gly His Glu His Asp
    290                 295                 300

Phe Glu Phe Cys Ala Val Glu Leu Trp Arg Leu Ile Ala Pro Ala Thr
305                 310                 315                 320

Gly Arg Cys Asp Val Thr Pro Pro Ser Arg Asp Gly Arg Asp Ala
                325                 330                 335

Ile Gly Asp Tyr Ile Leu Gly Pro Leu Ser Asp Pro Ile Ala Ile Asp
        340                 345                 350

Phe Ala Leu Glu Ala Lys Cys Tyr Thr Asp Thr Asn Ser Val Gly Val
            355                 360                 365

Arg Asp Val Ala Arg Leu Ile Ser Arg Leu Arg His Arg His Phe Gly
    370                 375                 380

Val Phe Ile Thr Thr Ser His Phe Asn Gln Gln Val Tyr Thr Glu Val
385                 390                 395                 400

Arg Thr Asp Arg His Pro Ile Ala Leu Val Ser Gly Arg Asp Ile Val
                405                 410                 415

Asn Ala Leu Arg Ala His Gly Tyr Ala Asp Val Asn Ala Val Asn Ala
        420                 425                 430

Trp Leu Gly Lys Ile Pro Asn Val His Val Ser Ala Lys Gly Ala Pro
            435                 440                 445

Asn Pro
    450

<210> SEQ ID NO 10
<211> LENGTH: 402
<212> TYPE: PRT
<213> ORGANISM: Streptomyces griseoflavus

<400> SEQUENCE: 10

Met Pro Leu Ala Asp Ala Pro Val Pro His Val Thr Phe Ala Glu Leu
1               5                   10                  15

Thr Thr Thr Asp Leu Val Val Asp Ala Val Tyr Ala Gly Gly Ser Ser
                20                  25                  30

Gly His Thr Gly Asp Asp Pro Met Ser Lys Ile Ile Lys Gly Ile Gly
            35                  40                  45

Asn Gln Gly Gly Phe Arg Tyr Ala Gly Ser Pro Ala Leu Gly Thr Val
        50                  55                  60

Lys Leu Ala Val Leu Tyr Thr Ser Gly Gly Glu Val Asp Trp Pro Asp
65                  70                  75                  80

Tyr Leu Asp Val Glu Thr Gly Thr Phe Thr Tyr Gly Asp Asn Arg
                85                  90                  95

Arg Pro Gly Gln Ser Leu His Glu Thr Pro Arg Ser Gly Asn Ile Leu
            100                 105                 110

Leu Arg Asp Ala Phe Ala Ala Ser His Gly Thr Pro Ala Asp Arg Ser
        115                 120                 125

Lys Val Pro Pro Phe Phe Leu Phe Glu Lys Ala Ala Ala Arg Gly Arg
    130                 135                 140

Ser Val Leu Phe Arg Gly Leu Leu Ala Pro Gly Gly Pro Asn Leu Thr
145                 150                 155                 160

Ser Asp Asp Glu Leu Ala Ala Ile Trp Arg Ala Thr Asp Gly Arg Arg
                165                 170                 175

Phe Gln Asn Tyr Arg Ala Arg Phe Thr Val Leu Glu Val Asp Arg Val
```

```
                    180             185             190
Pro Arg Ala Trp Ile Gln His Leu Leu Asn Gly Gly Asp Pro Leu Asp
        195                     200                 205

Gly Glu Cys Pro Asp Ala Trp Arg Thr Trp Thr Glu Ser Arg Val Tyr
    210                     215                 220

Arg Pro Leu Leu Ala Pro Ser Thr Thr Val Val Arg Ser Lys Ala Asp
225                     230                 235                 240

Gln Leu Pro Gly Asp Ala Val Gly Lys Ala Met Leu Gln Glu Ile Arg
                245                 250                 255

Asp Tyr Phe Arg Gly Arg Glu His Asp Phe Glu Leu Cys Ala Val Ala
            260                 265                 270

Ile Trp Arg Leu Met Ala Pro Ser Thr Gly Ala Val Asp Val Thr Arg
            275                 280                 285

Pro Ser Arg Asp Gly Gly Arg Asp Ala Val Gly Thr Tyr Leu Leu Gly
        290                 295                 300

Pro Ala Ala Asn Arg Ile Ala Val Asp Phe Ala Leu Glu Ala Lys Cys
305                 310                 315                 320

Tyr Gly Pro Asp Asn Ser Val Gly Val Arg Glu Val Ser Arg Leu Ile
                325                 330                 335

Ser Arg Leu Arg His Arg Asn Phe Gly Val Leu Val Thr Thr Ser Phe
            340                 345                 350

Leu Asn Lys Gln Val Gln Glu Ile Gln Glu Asp Gly His Pro Ile
            355                 360                 365

Ala Leu Val Cys Gly Arg Asp Ile Val Glu Val Leu Arg Gln His Gly
        370                 375                 380

Arg Thr Thr Ala Asp Ser Val Arg Gln Trp Leu Thr Gln Ser Phe Pro
385                 390                 395                 400

Gln Pro

<210> SEQ ID NO 11
<211> LENGTH: 388
<212> TYPE: PRT
<213> ORGANISM: Azoarcus sp.

<400> SEQUENCE: 11

Met Thr Phe Phe Thr Gly Glu Thr Leu Gly Gln Val Asp Leu Ile Val
1               5                   10                  15

Asp Ala Val Tyr Ala Gly Tyr Lys Thr Glu Arg Gly Gly Met Ala Asp
                20                  25                  30

Pro Leu Val Pro Leu Val Gly Val Ser Arg Gln Gly Gly Phe Arg Tyr
            35                  40                  45

Arg Gly Thr Arg Glu Arg Pro Thr Leu Leu Val Leu Thr Ser Asn Leu
    50                  55                  60

Ala Glu Pro Glu Trp Pro Asp Gln Leu Asp Glu Thr Thr Gly Thr Phe
65                  70                  75                  80

Ile Tyr Tyr Gly Asp Asn Arg His Pro Gly Arg Leu Leu His Asp Thr
                85                  90                  95

Pro Arg Phe Gly Asn Gln Leu Leu Arg Gln Ile Phe Asp Trp Ala His
            100                 105                 110

Leu Gly Gln Arg His Leu Val Pro Pro Ile Leu Val Phe Thr Thr Glu
        115                 120                 125

Ala Thr Gly Arg Thr Phe Arg Phe Arg Gly Leu Ala Val Pro Gly Ser
    130                 135                 140

Pro Ala Leu Ala Ala Thr Glu Asp Leu Val Ala Leu Trp Lys Thr Thr
145                 150                 155                 160
```

-continued

```
Glu Gly Gln Arg Phe Gln Asn Tyr Lys Ala Val Phe Thr Ile Leu Asp
                165                 170                 175

Glu Ala Val Ile Pro Arg Ala Trp Val His Ala Val Gly Arg Gly Glu
            180                 185                 190

Thr Ser Gly Leu Ala Pro Val Ala Trp Asn Ala Trp Leu Ser Ala Gly
        195                 200                 205

Gly Ile Arg Pro Leu Met Ala Pro Arg Ser Leu Leu Val Arg Ser Lys
    210                 215                 220

Ala Glu Gln Leu Pro Ala Thr Pro Glu Asp Gln Ala Leu Ile Glu Val
225                 230                 235                 240

Ile Arg Gln Arg Tyr Lys Glu Asn Pro Phe Gly Phe Glu Ala Cys Ala
                245                 250                 255

Gly Ala Leu Thr Arg Leu Leu Leu Pro Asp Val Ala Arg Leu Asp Leu
            260                 265                 270

Thr Arg Pro Trp Arg Asp Gly Gly Arg Asp Gly Ile Gly Arg Leu Arg
        275                 280                 285

Ile Gly Gln Ser Pro Ala Ala Ile Glu Val Asp Phe Ala Leu Glu Ala
    290                 295                 300

Lys Cys Tyr Gly Ala Asn Asn Ala Val Gly Val Lys Glu Val Ser Arg
305                 310                 315                 320

Leu Ile Ser Arg Ile Lys His Arg Glu Phe Gly Val Leu Val Thr Thr
                325                 330                 335

Ser Tyr Val Asp Arg Gln Ala Tyr Gln Glu Val Thr Asp Asp Gly His
            340                 345                 350

Pro Val Ile Leu Thr Thr Ala Gln Asp Ile Val Gly Leu Leu Arg Ser
        355                 360                 365

Ala Gly Val Arg Thr Pro Thr Gln Val Asp Ala Trp Leu Asp Gly Ile
    370                 375                 380

Thr Ala Ser Val
385

<210> SEQ ID NO 12
<211> LENGTH: 285
<212> TYPE: PRT
<213> ORGANISM: Burkholderia cenocepacia

<400> SEQUENCE: 12

Met Leu Arg Asn Leu Phe Asp Glu Ala His Gln Phe Gln Gln Ser Ser
1               5                   10                  15

Ser Phe Pro Pro Ile Leu Leu Phe Gly Asn Ala Gly Thr Tyr Arg Asp
            20                  25                  30

Val Arg Phe Leu Gly Leu Ala Val Pro Gly Ala Ala Gly Met Gly Ala
        35                  40                  45

Asp Asp Asp Leu Val Ala Val Trp Arg Thr Thr Glu Asp Gly Val Arg
    50                  55                  60

Phe Gln Asn Tyr Lys Ala Thr Phe Thr Ile Leu Asp Leu Pro Val Val
65                  70                  75                  80

Ser Arg Ala Trp Ile Lys Asp Val Gln Asn Gly Asn Ala Val Ser Ser
                85                  90                  95

Ala His Ala Pro Lys Ala Trp Leu Asp Trp Val Ser Gly Arg Lys Tyr
            100                 105                 110

Thr Pro Leu Lys Ser Val Pro Val Ser Val Val Arg Ser Lys Arg Gln
        115                 120                 125

Gln Val Pro Asp Thr Pro Glu Leu Ala Ala Tyr Val Lys Thr Val Tyr
    130                 135                 140
```

-continued

```
Glu His Tyr Lys Glu Asp Pro Tyr Ala Phe Glu Arg Cys Ala Met Glu
145                 150                 155                 160

Leu Ala Arg Leu Phe Met Pro Ala Ile Gln His Trp Glu Leu Thr Arg
                165                 170                 175

Pro Trp Arg Asp Gly Gly Arg Asp Ala Leu Gly Thr Tyr Arg Ile Gly
            180                 185                 190

His Gly Ala Gly Ala Ile Asp Val Glu Phe Ala Met Glu Ala Lys Cys
        195                 200                 205

Tyr Asp Gln Asn Val Gly Val Gly Ile Lys Pro Leu Ser Arg Leu Ile
    210                 215                 220

Ser Arg Leu Arg His Arg Gln Phe Gly Ile Leu Val Thr Thr Ser Tyr
225                 230                 235                 240

Leu Asp Ala Gln Ala Tyr Ser Glu Leu Val His Asp Thr His Pro Val
                245                 250                 255

Val Val Ile Ser Ala Lys Asp Ile Ser Met Lys Leu Arg Glu Arg Phe
            260                 265                 270

Gly Ser Leu Glu Ser Ile Lys Leu Trp Leu Gln Arg Ile
        275                 280                 285

<210> SEQ ID NO 13
<211> LENGTH: 399
<212> TYPE: PRT
<213> ORGANISM: Legionella pneumophila

<400> SEQUENCE: 13

Met Lys Ile Tyr Ser Phe Asp Thr Leu Ala Asn Ala Asp Leu Ile Ile
1               5                   10                  15

Asp Ala Val Tyr Glu Gly Gly Ser Ser Gly Asn Ala Ser Asp Asp Pro
            20                  25                  30

Ile Ser Lys Ile Ile Lys Gly Ile Gly Asn Met Gly Gly Phe Arg Ser
        35                  40                  45

Ala Gly Gln Gly Ile Phe Lys Lys Leu Ile Val Leu Tyr Thr Asn Met
    50                  55                  60

Glu Asp Gly Asp Trp Pro Asp Ser Ile Asp Thr Ser Lys Gly Gln Phe
65                  70                  75                  80

Ile Tyr Tyr Gly Asp Asn Lys His Pro Gly His Asp Ile His Asp Thr
                85                  90                  95

Pro Arg Gln Gly Asn Ala Thr Leu Lys Met Leu Phe Asp Ser Thr His
            100                 105                 110

Asn Glu Lys Asp Ala Arg Arg Ile Val Pro Pro Ile Phe Ile Phe Val
        115                 120                 125

Lys Tyr Pro Thr Ala Ser Ser Ser Arg Ser Val Gln Phe Lys Gly Val
    130                 135                 140

Ala Val Pro Gly Tyr Pro Gly Leu Ser Ala Thr Asp Asp Leu Ile Ala
145                 150                 155                 160

Val Trp Lys Thr Thr Asn Gly Gln Arg Phe Gln Asn Tyr Arg Ala Ile
                165                 170                 175

Phe Thr Ile Leu Asn Ile Pro Met Val Ser Arg Lys Trp Ile Asn Ser
            180                 185                 190

Leu Phe Asp Pro Phe Gly Gln Asp Asn Ser Leu Asn Pro Phe Tyr Gln
        195                 200                 205

Trp Lys Ile Ser Gly Lys Ala Asp Val Leu Ile Ala Pro Ser Thr Lys
    210                 215                 220

Thr Ile Arg Thr Gln Ile Glu Gln Met Pro Arg Thr Lys Leu Glu Arg
225                 230                 235                 240
```

-continued

```
Glu Ile Leu Gln Ala Val Phe Asp Tyr Phe Cys Glu Ala Pro Ile Lys
                245                 250                 255

Phe Glu Ala Cys Ala Ala Lys Ile Phe Gln Leu Tyr Asp Glu Asn Val
            260                 265                 270

Leu Ile Asp Glu Ile Thr Arg Ser Ala Val Asp Gly Lys Asp Ala
        275                 280                 285

Ile Gly Arg Tyr Val Leu Gly Ile Lys Glu Asp Pro Val Tyr Ala Glu
    290                 295                 300

Phe Phe Leu Glu Ala Lys Cys Tyr Gln Pro Gly Leu Asn Gly Gln Asn
305                 310                 315                 320

Ile Asn Ser Val Gly Val Lys Glu Val Ser Arg Leu Ile Ser Arg Ile
                325                 330                 335

Lys Asn Arg Gln Phe Gly Val Leu Val Thr Thr Ser Phe Ile Ala Lys
                340                 345                 350

Gln Ala Tyr Gly Glu Val Arg Glu Asp Gly His Pro Ile Val Phe Leu
            355                 360                 365

Ser Gly Gly Asp Ile Ser Arg Ile Leu Ile Lys Gly Ile Asn Ser
    370                 375                 380

Thr Asp Ala Val Leu Ala Trp Leu Asn Ser Glu Phe Ser Lys Ser
385                 390                 395

<210> SEQ ID NO 14
<211> LENGTH: 369
<212> TYPE: PRT
<213> ORGANISM: Ralstonia metallidurans

<400> SEQUENCE: 14

Met Gly Gly Phe Arg Val Thr Gly Arg Gly Glu Gln Lys Ser Trp Val
1               5                   10                  15

Val Leu Phe Thr Thr Gly Glu Asp Lys Asp Trp Pro Asp Thr Leu Asp
            20                  25                  30

Leu Ser Thr Gly Lys Phe Val Tyr Phe Gly Asp Asn Lys Thr Pro Gly
        35                  40                  45

His Glu Leu His Glu Thr Arg Gly Gly Asn Lys Val Leu Arg Tyr Ser
    50                  55                  60

Phe Glu Arg Leu His Ala Ala Val Asn Pro Arg Ala Asp Val Ala Pro
65                  70                  75                  80

Phe Leu Val Phe Lys Lys Tyr Pro Leu Ala His Gly Ala Arg Ser Val
                85                  90                  95

Gln Phe Lys Gly Leu Ala Val Pro Gly Phe Pro Ser Leu Ser Ser Thr
            100                 105                 110

Glu Asp Leu Val Ala Val Trp Lys Ser Ser Glu Gly Gln Arg Phe Gln
        115                 120                 125

Asn Tyr Arg Ala Val Phe Thr Ile Leu Asn Ala Pro Val Leu Ser Arg
130                 135                 140

Ala Trp Ile Asn Asp Leu Lys Ala Gly Asp Leu Asn Ser Ser Asn Ala
145                 150                 155                 160

Pro Arg Ala Trp Arg Gln Trp Arg Glu Ser Gly Lys Tyr Ser Pro Leu
                165                 170                 175

Ala Ala Ala Pro Thr Thr Asn Ile Arg Ser Ala Asn Ala Gln Ser Pro
            180                 185                 190

Asp Thr Ala Leu Lys Arg Glu Leu Leu Glu Cys Ile Trp Gln His Tyr
        195                 200                 205

Lys Gly Ala Pro Ile Ala Phe Glu Ala Phe Ala Ala Arg Val Phe Gln
    210                 215                 220
```

```
Met Thr Asp Glu Arg Val Val Ile Asp Glu Ile Thr Arg Gly Val Val
225                 230                 235                 240

Asp Gly Gly Arg Asp Ala Ile Gly Arg Tyr Arg Leu Gly Ser Met Ala
            245                 250                 255

Asp Pro Val Tyr Ala Glu Phe Ser Leu Glu Ala Lys Cys Tyr Arg Pro
        260                 265                 270

Pro Leu Asn Gly Asp Thr Pro Ile Thr Val Ser Val Ser Asp Val Ala
        275                 280                 285

Arg Leu Ile Ser Arg Ile Arg His Arg Gln Phe Gly Val Leu Val Thr
        290                 295                 300

Thr Ser Val Ile Ala Ser Gln Ala Tyr Lys Glu Val Arg Glu Asp Arg
305                 310                 315                 320

His Pro Ile Val Phe Ile Ser Gly Gly Asp Met Val Asn Ile Leu Ile
                325                 330                 335

Asp Lys Gly Tyr Asn Thr Arg Gly Arg Val Gln Glu Leu Leu Ser Ser
            340                 345                 350

Asp Phe Ala Leu Val Ala Ala Ser Ser Glu Pro Val Asp Lys Pro
        355                 360                 365

Arg

<210> SEQ ID NO 15
<211> LENGTH: 392
<212> TYPE: PRT
<213> ORGANISM: Ruminococcus lactaris

<400> SEQUENCE: 15

Met Gln Arg Ile Ala Phe Glu Lys Leu Lys Thr Ala Asp Leu Phe Val
1               5                   10                  15

Asp Ala Val Tyr Glu Ser Asn Gly Ala Thr Asn Leu Asn Gly Asp Val
            20                  25                  30

Leu Ser Lys Leu Met Ser Val Gly Thr Gln Gly Gly Phe Arg Pro Val
        35                  40                  45

Asn Ile Arg Asn Gln Lys Gly Lys Ala Ala Tyr Ile Val Leu Glu Ser
    50                  55                  60

Thr Asn Lys His Pro Asp Trp Leu Asp Asn Ile Asp Tyr Glu Ser Gly
65                  70                  75                  80

Ile Ile Gln Tyr Tyr Gly Asp Asn Arg Glu Pro Gly Arg Glu Leu His
                85                  90                  95

Asp Ser Lys Arg Gly Asn Lys Val Leu Arg Asp Val Phe Glu Met
            100                 105                 110

Leu Gln Asp Asn Arg Arg Gln Glu Ile Pro Pro Phe Phe Tyr Phe Glu
        115                 120                 125

Ser Glu Glu Gly Arg Asn Arg Arg Phe Leu Gly Leu Leu Val Pro Gly
    130                 135                 140

Ser Asp Lys Phe Lys Leu Glu Glu Leu Leu Val Ala Ile Trp Arg Met
145                 150                 155                 160

Lys Asn Gly Glu Arg Tyr Gln Asn Tyr Lys Ala Val Phe Thr Ile Leu
                165                 170                 175

Asp Val Ala Ser Val Ser Arg Gly Trp Leu Glu Asp Leu Leu Ser Gly
            180                 185                 190

Asn Gly Tyr Gln Ser Asp Phe Ala Pro Lys Glu Trp Lys Lys Trp Ile
        195                 200                 205

Asp Lys Gly Val Tyr Thr Pro Leu Tyr Ala Ser Asp Ser Val Leu Asn
    210                 215                 220
```

-continued

```
Tyr Arg Thr Gln Asp Gln Gln Met Pro Phe Lys Asp Asp Lys Gln
225                 230                 235                 240

Lys Leu Gln Ser Ile Tyr Asp Tyr Phe Asp Asn Pro Tyr Glu Phe Glu
            245                 250                 255

Lys Cys Ala Met Lys Ile Val Gln Leu Met Asp Ser Asn Ile His Ser
                260                 265                 270

Leu Lys His Thr Arg Phe Val Arg Asp Gly Gly Arg Asp Ala Ile Gly
            275                 280                 285

Leu Tyr Arg Ile Gly Arg Gln Cys Asp Gly Val Asp Val Glu Phe Ala
            290                 295                 300

Leu Glu Ala Lys Arg Tyr Ser Ser Asn Asp Gly Ile Gly Val Lys Glu
305                 310                 315                 320

Val Ser Arg Leu Ile Ser Arg Leu Arg His Arg Gln Phe Gly Ile Leu
                325                 330                 335

Val Thr Thr Ser Phe Val Ala Leu Gln Ala Tyr Gln Glu Ile Lys Glu
            340                 345                 350

Asp Gly His Pro Ile Val Ile Ser Gly Met Asp Ile Leu Arg Ile
            355                 360                 365

Leu Tyr Asp Ser Gly Ile Lys Thr Lys Asp Glu Ile Gln Glu Trp Leu
            370                 375                 380

Val Lys Thr Phe Pro Lys Asp Glu
385                 390

<210> SEQ ID NO 16
<211> LENGTH: 433
<212> TYPE: PRT
<213> ORGANISM: Lactobacillus helveticus

<400> SEQUENCE: 16

Met Val Leu His Ile Gly Val Ser Tyr Lys Thr Gly Pro Gln Ala Lys
1               5                   10                  15

Lys Glu Ala Gln Glu Ile Ser Asp Thr Tyr Tyr Ile Ser Glu Asp
            20                  25                  30

Asp Ser Ser Lys Asn Tyr Phe Ile Glu Thr His Leu Lys Asp Gly Lys
        35                  40                  45

Lys Asn Tyr Phe Asn Gln Ala Gly Ile Phe Lys Pro Ala Glu Asn Glu
    50                  55                  60

Cys Ile Ile Ile Ser Ser Asn Thr Lys Ser Arg Gly Ile Asn Tyr Asn
65                  70                  75                  80

Pro Trp Glu Asp Glu Phe Asn Glu Asp Val Gly Tyr Ile Asn Tyr Tyr
                85                  90                  95

Gly Asp Asn Lys Arg Pro Asp Thr Asp Pro Ala Thr Thr Arg Gly Asn
            100                 105                 110

Lys Tyr Leu Leu Asp Gln Phe Lys Ile Ser His Asp Pro Asn Pro Glu
        115                 120                 125

Val Arg Ala Thr Ala Val Pro Ile Ile Phe Phe Glu Thr Arg Lys Gln
    130                 135                 140

Gly Glu Arg Ile Phe His Gly Tyr Gly Val Ile Lys Asn Val Lys Leu
145                 150                 155                 160

Val Thr Gln Tyr Thr Gly Ser Gly Ala Asp Lys Ala Tyr Phe Ser Asn
                165                 170                 175

Tyr Leu Phe Thr Phe Cys Val Phe Ser Met Lys Lys Glu Gln Glu Gly
            180                 185                 190

Phe Asp Trp Ser Trp Ile Glu Ala Arg Lys Gln Ala Ala Lys Asp Lys
        195                 200                 205
```

```
Asn Phe Leu Ser Leu Ala Asn Ala Leu Ala Pro Lys Glu Trp Lys Phe
            210                 215                 220
Trp Ile Arg Thr Gly Asp Leu Glu Lys Val Arg Lys Val Tyr Gly
225                 230                 235                 240
Arg Ser Thr Ser Lys Lys Glu Glu Gln Leu Pro Thr Pro Gly Ser Ala
                245                 250                 255
Asp Asp Lys Ile Leu Asn Gln Ile Tyr Glu Tyr Tyr Arg Lys Lys Asp
                260                 265                 270
Asn Ser Lys Ala His Ser Gly Asp Phe Glu Phe Glu Gly Leu Ala Lys
            275                 280                 285
Glu Ile Thr Arg Leu Ile Ile Gly Asp Ala Cys His Asp Gly Trp Val
            290                 295                 300
Thr Lys Ser Ser Gly Asp Gly Gly Tyr Asp Phe Val Leu Arg Val Asp
305                 310                 315                 320
Ile Gly Thr Lys Gly Ile Ser Gln Val Arg Gln Val Val Leu Gly Gln
                325                 330                 335
Ala Lys Cys Tyr Arg Arg Asp Gln Arg Ile Thr Gly Glu Ala Val Asp
                340                 345                 350
Arg Val Val Ala Arg Leu Lys Arg Gly Trp Ile Ala Ala Phe Val Thr
            355                 360                 365
Thr Ser Phe Phe Ser Asp Pro Ala Gln Arg Glu Ile Leu Glu Asp Asp
            370                 375                 380
Tyr Pro Ile Met Leu Ile Ser Gly Lys Gln Val Ala Gln Thr Val Arg
385                 390                 395                 400
Lys Tyr Ile Tyr Glu Lys Asn Ile Thr Leu Arg Glu Tyr Leu Asp Ser
                405                 410                 415
Leu Ser Arg Asp Gln Ser Phe Lys Ser Pro Glu Asp Ile Leu Lys Glu
            420                 425                 430
Glu

<210> SEQ ID NO 17
<211> LENGTH: 383
<212> TYPE: PRT
<213> ORGANISM: Lactobacillus helveticus

<400> SEQUENCE: 17

Tyr Phe Asn Gln Ala Gly Ile Phe Lys Pro Ala Glu Asn Glu Cys Ile
1               5                   10                  15
Ile Ile Ser Ser Asn Thr Lys Ser Arg Gly Ile Asn Tyr Asn Pro Trp
                20                  25                  30
Glu Asp Glu Phe Asn Glu Asp Val Gly Tyr Ile Asn Tyr Tyr Gly Asp
            35                  40                  45
Asn Lys Arg Pro Asp Thr Asp Pro Ala Thr Thr Arg Gly Asn Lys Tyr
        50                  55                  60
Leu Leu Asp Gln Phe Lys Ile Ser His Asp Pro Asn Ser Glu Val Arg
65                  70                  75                  80
Ala Thr Ala Val Pro Ile Ile Phe Glu Thr Arg Lys Gln Gly Glu
                85                  90                  95
Arg Ile Phe His Gly Tyr Gly Val Ile Lys Asn Val Lys Leu Val Thr
            100                 105                 110
Gln Tyr Thr Gly Ser Gly Ala Asp Lys Ala Tyr Phe Ser Asn Tyr Leu
        115                 120                 125
Phe Thr Phe Cys Val Phe Ser Met Lys Lys Glu Gln Glu Gly Phe Asp
    130                 135                 140
Trp Ser Trp Ile Glu Ala Arg Lys Gln Ala Ala Lys Asp Lys Asn Phe
```

```
                145                 150                 155                 160
Leu Ser Leu Ala Asn Ala Leu Ala Pro Lys Glu Trp Lys Phe Trp Ile
            165                 170                 175

Arg Thr Gly Asp Leu Glu Lys Val Arg Arg Lys Val Tyr Gly Arg Ser
        180                 185                 190

Thr Ser Lys Lys Glu Glu Gln Leu Pro Thr Pro Gly Ser Ala Asp Asp
    195                 200                 205

Lys Ile Leu Asn Gln Ile Tyr Glu Tyr Arg Lys Lys Asp Asn Ser
    210                 215                 220

Lys Ala His Ser Gly Asp Phe Glu Phe Glu Gly Leu Ala Lys Glu Ile
225                 230                 235                 240

Thr Arg Leu Ile Ile Gly Asp Ala Cys His Asp Gly Trp Val Thr Lys
            245                 250                 255

Ser Ser Gly Asp Gly Gly Tyr Asp Phe Val Leu Arg Val Asp Ile Gly
        260                 265                 270

Thr Lys Gly Ile Ser Gln Val Arg Gln Val Val Leu Gly Gln Ala Lys
    275                 280                 285

Cys Tyr Arg Arg Asp Gln Arg Ile Thr Gly Glu Ala Val Asp Arg Val
    290                 295                 300

Val Ala Arg Leu Lys Arg Gly Trp Ile Ala Ala Phe Val Thr Thr Ser
305                 310                 315                 320

Phe Phe Ser Asp Pro Ala Gln Arg Glu Ile Leu Glu Asp Asp Tyr Pro
            325                 330                 335

Ile Met Leu Ile Ser Gly Lys Gln Val Ala Gln Thr Val Arg Lys Tyr
        340                 345                 350

Ile Tyr Glu Lys Asn Ile Thr Leu Arg Glu Tyr Leu Asp Ser Leu Ser
    355                 360                 365

Arg Asp Gln Ser Phe Lys Ser Pro Glu Asp Ile Leu Lys Glu Glu
    370                 375                 380

<210> SEQ ID NO 18
<211> LENGTH: 436
<212> TYPE: PRT
<213> ORGANISM: Shewanella pealeana

<400> SEQUENCE: 18

Met Ile Asn Ile Val Glu Ile Gln Ile Gly Val Val Leu Arg Tyr Lys
1               5                   10                  15

Lys Pro Ser Cys Ala Val Asn Met Tyr Glu Asp Gly His Leu Asn Phe
            20                  25                  30

His Phe Leu Thr Lys His Ser Glu Ala Asn Asn Leu Gln Leu Glu Lys
        35                  40                  45

Gly Ile Asn Pro Ser Ala Lys Ile Lys Thr Asn Ser Gly Glu Leu Val
    50                  55                  60

Arg Ser Ala Ile Leu Val Ser Ser Ser Pro Asn Lys Lys Gly Ser Ile
65                  70                  75                  80

Glu Thr Pro Trp Glu Asp Phe Tyr Asp Val Asp Asn Gly His Ile Arg
            85                  90                  95

Tyr Phe Gly Asp Asn Lys Glu Pro Gly Lys Asp Pro Ala Thr Ala Pro
        100                 105                 110

Gly Asn Lys Ala Leu Leu Glu Ala Phe Arg Leu Ala His Ser His Ser
    115                 120                 125

Ala Glu Glu Arg Ala Leu Thr Pro Pro Ile Leu Phe Phe Lys Arg Ala
    130                 135                 140

Val Ile Asn Gly Val Ala Lys Gly Tyr Pro Gln Phe Tyr Gly Leu Gly
```

```
                145                 150                 155                 160
Ile Ile Asn Ser Val Glu Leu Val Thr Gln Trp Asp Asn Lys Leu Ala
                    165                 170                 175

Arg Thr Phe Thr Asn Tyr Ala Phe Asp Phe Thr Val Leu Cys Ile Ala
            180                 185                 190

Ser Glu His Glu Glu Phe Glu Trp Asp Trp Ile Asn Ser Arg Arg Lys
        195                 200                 205

Lys Gly Phe Ser Leu Ser Ile Thr Asn Lys Ala Ser Pro Lys Ser Trp
    210                 215                 220

Arg Gln Trp Leu Ile Glu Gly Ser Asn Ser Leu Asn Lys Leu Arg Arg
225                 230                 235                 240

Arg Val Ser Lys Leu Ser Leu Glu Lys Thr Val Asn Gln Lys Pro Ile
                245                 250                 255

Pro Gly Ser Glu Ser Asp Arg Ile Leu Asn Glu Ile Tyr Ile Tyr Tyr
            260                 265                 270

Ala Asn Lys Lys His Arg Phe Glu Ala Leu Ala Glu Val Ile Ala Ala
        275                 280                 285

Arg Val Ile Asp Arg Glu Phe Gly Ile Tyr His Lys Gly Trp Val Thr
    290                 295                 300

Gln Gly Ser Ser Asp Gly Gly Ala Asp Phe Val Gly Lys Val Thr Leu
305                 310                 315                 320

Gly Ser Gly Phe Ser Lys Val Glu Leu Ile Val Leu Gly Gln Ala Lys
                325                 330                 335

Cys Glu Ala Leu Asn Ser Pro Thr Gly Gly Asn His Ile Ala Arg Thr
            340                 345                 350

Val Ala Arg Leu Lys Arg Gly Trp Leu Gly Val Tyr Val Thr Thr Ser
        355                 360                 365

Tyr Phe Ser Asp Ser Val Gln Arg Glu Val Ile Glu Asp Lys Tyr Pro
    370                 375                 380

Ile Ile Leu Ile His Gly Arg Arg Ile Ala Glu Glu Val Ala Lys Ile
385                 390                 395                 400

Val Tyr Glu Ser Glu Glu Phe Glu Ser Val Asn Ser Phe Leu Val Ala
                405                 410                 415

Met Asp Lys Asp Tyr Pro Thr Arg Leu Lys Gln Arg Gln Ala Glu Glu
            420                 425                 430

Val Leu Asn Ile
            435

<210> SEQ ID NO 19
<211> LENGTH: 432
<212> TYPE: PRT
<213> ORGANISM: Shewanella baltica

<400> SEQUENCE: 19

Met Glu Ile Gln Ile Gly Asp Val Leu Arg Tyr Lys Lys Pro Ala Cys
1               5                   10                  15

Gly Glu Asn Met Tyr Glu Asp Gly Tyr Leu Asn Phe His Phe Leu Thr
            20                  25                  30

Lys Ser Ile Asp Ala Asn Asn Leu Gln Leu Glu Lys Gly Ile Asn Pro
        35                  40                  45

Ser Ala Lys Ile Lys Thr Ser Leu Gly Gln Leu Val Arg Pro Ala Ile
    50                  55                  60

Leu Ile Ser Ser Pro Asn Lys Lys Gly Ser Ile Glu Thr Pro Trp
65                  70                  75                  80

Glu Asp Phe Tyr Asp Val Asp Asn Gly His Ile Arg Tyr Phe Gly Asp
```

```
            85                  90                  95
Asn Lys Glu Pro Gly Lys Asp Pro Ala Thr Ala Pro Gly Asn Lys Ala
            100                 105                 110

Leu Leu Glu Ala Phe Arg Leu Ala His Ser His Asn Val Asp Glu Arg
        115                 120                 125

Leu Leu Thr Pro Pro Ile Leu Phe Phe Lys Arg Ala Ile Val Asn Gly
    130                 135                 140

Val Ala Lys Gly Tyr Pro Gln Phe Tyr Gly Leu Gly Ile Ile Asn Ser
145                 150                 155                 160

Val Glu Leu Val Thr Gln Trp Asp Asn Lys Leu Ala Arg Thr Phe Thr
                165                 170                 175

Asn Tyr Ala Phe Asp Phe Thr Val Leu Cys Ile Ala Gly Glu His Glu
            180                 185                 190

Lys Phe Glu Trp Asp Trp Ile Asn Asn Arg Arg Lys Lys Ala Phe Ser
        195                 200                 205

Leu Ala Ile Thr Asn Gln Thr Ala Pro Lys Ser Trp Arg Gln Trp Leu
    210                 215                 220

Cys Glu Gly Ser Asn Ala Leu Asn Lys Leu Arg Arg Arg Val Ser Lys
225                 230                 235                 240

Leu Ser Leu Glu Lys Ala Val Asn Gln Lys Pro Ile Pro Gly Ser Glu
                245                 250                 255

Ser Asp Lys Ile Leu Asn Gln Ile Tyr Asp Tyr Tyr Ala Asn Lys Lys
            260                 265                 270

His Arg Phe Glu Ala Leu Ala Glu Val Ile Ala Glu Arg Val Ile Asp
        275                 280                 285

Arg Glu Leu Gly Ile Tyr Gln Lys Gly Trp Val Thr Gln Gly Ser Gly
    290                 295                 300

Asp Gly Gly Ala Asp Phe Ile Gly Lys Val Thr Leu Gly Ser Gly Phe
305                 310                 315                 320

Ser Lys Val Glu Leu Ile Val Leu Gly Gln Ala Lys Cys Glu Ser Leu
                325                 330                 335

Asn Thr Pro Thr Gly Gly Asn His Ile Ala Arg Thr Val Ala Arg Leu
            340                 345                 350

Lys Arg Gly Trp Leu Gly Val Tyr Val Thr Thr Ser Tyr Phe Ser Asp
        355                 360                 365

Ser Val Gln Arg Glu Val Ile Glu Asp Lys Tyr Pro Ile Val Leu Ile
    370                 375                 380

His Gly Arg Arg Leu Ala Glu Glu Val Ala Lys Ile Val Tyr Glu Ser
385                 390                 395                 400

Glu Ala Tyr Ser Asn Val Thr Glu Phe Leu Ile Ala Met Asp Ala Val
                405                 410                 415

Tyr Pro Ser Arg Leu Lys Gln Arg Gln Ala Glu Ile Leu Asn Asn
            420                 425                 430

<210> SEQ ID NO 20
<211> LENGTH: 432
<212> TYPE: PRT
<213> ORGANISM: Moritella sp.

<400> SEQUENCE: 20

Met Glu Ile Lys Ile Asn Asp Ile Leu Arg Tyr Lys Lys Pro Ala Cys
1               5                   10                  15

His Glu Asn Ala Tyr Glu Asp Gly His Leu Asn Phe His Phe Leu Thr
            20                  25                  30

Asn Val Pro Thr Ser Lys Lys Leu Gln Leu Glu Lys Gly Ile Asn Pro
```

```
                35                  40                  45
Ser Ala Ala Leu Lys Thr Ser Asp Lys Glu Leu Val Arg Pro Val Ile
 50                  55                  60

Leu Ile Ser Ser Pro Asn Lys Lys Gly Ser Ala Glu Thr Pro Trp
 65                  70                  75                  80

Gln Asp Phe Tyr Asp Thr Asp Asn Gly His Ile Arg Tyr Phe Gly Asp
                 85                  90                  95

Asn Lys Glu Pro Gly Lys Asp Pro Thr Gln Ala Pro Gly Asn Lys Ala
                100                 105                 110

Leu Leu Glu Ala Phe Arg Leu Ala His Ser His Asp Ile Lys Glu Arg
                115                 120                 125

Gln Lys Thr Pro Pro Ile Val Phe Phe Lys Arg Val Thr Val Asn Gly
                130                 135                 140

Val Pro Lys Gly Tyr Pro Met Phe Gln Gly Leu Gly Ile Ile Asn Ser
145                 150                 155                 160

Ile Glu Leu Val Thr Gln Trp Asp Asn Asn Lys Gln Gln Ser Phe Thr
                165                 170                 175

Asn Tyr Ala Phe Asp Phe Thr Val Leu Cys Met Ala Lys Glu His Asp
                180                 185                 190

Thr Phe Glu Trp Asp Trp Ile Asn Ser Arg Arg His Pro Asn Phe Ser
                195                 200                 205

Ile Gln Asp Thr Asn Lys Lys Ala Pro Ala Ser Trp Asn Gln Trp Phe
                210                 215                 220

Lys Ser Gly Ala Asn Glu Leu Asn Thr Val Arg Arg Val Ser Lys
225                 230                 235                 240

Leu Gln Ile Val Lys Ser Ala Asp Gln Lys Pro Thr Ile Gly Ser Glu
                245                 250                 255

Gln Asp Ala Ile Leu Asn Lys Ile Tyr Lys Phe Tyr Asp Gly Arg Lys
                260                 265                 270

His His Phe Glu Ala Leu Ala Glu Phe Ile Thr Glu Arg Val Ile Gly
                275                 280                 285

Lys Glu Leu Gly Ile Tyr His Lys Gly Trp Ile Thr Gln Gly Ser Ser
                290                 295                 300

Asp Gly Gly Ala Asp Phe Ile Gly Lys Val Val Leu Gly Ser Gly Phe
305                 310                 315                 320

Ser Lys Val Glu Leu Ile Val Leu Gly Gln Ala Lys Cys Glu Ser Leu
                325                 330                 335

Thr Thr Pro Thr Gly Gly Asn His Ile Ala Arg Thr Val Ala Arg Leu
                340                 345                 350

Lys Arg Gly Trp Leu Gly Ala Tyr Val Thr Thr Ser Tyr Phe Ser Asp
                355                 360                 365

Ser Val Gln Arg Glu Val Ile Glu Asp Lys Tyr Pro Ile Leu Leu Ile
                370                 375                 380

Asn Gly Lys Arg Ile Ala Glu Glu Val Ser Gln Leu Leu His Glu Ser
385                 390                 395                 400

Asp Thr Tyr Ser Asp Ile Asp Glu Phe Leu Ala Tyr Met Ala Glu Arg
                405                 410                 415

Tyr Pro Lys Arg Leu Lys Gln Arg Gln Pro Glu Glu Ile Leu His Val
                420                 425                 430

<210> SEQ ID NO 21
<211> LENGTH: 426
<212> TYPE: PRT
<213> ORGANISM: Xanthomonas campestris
```

-continued

<400> SEQUENCE: 21

Met Lys Arg Phe Arg Met Gly Glu Leu Tyr Arg Tyr Ala Arg Pro Ala
1               5                   10                  15

Leu Pro Glu Val Leu Glu Ile Asp Gly Ile Ser Asn Phe His Tyr Val
            20                  25                  30

Val Ala Ala Pro Gly Ser Pro Ser Leu Gln Leu Glu Arg Arg Ile Asn
        35                  40                  45

Ala Pro Ser Val Thr Arg Ala Ile Asp Gly Asp Arg Val Ala Val Val
    50                  55                  60

Leu Leu Ala Ser Asn Glu His Lys Arg Gly Ser Met Glu Asn Pro Trp
65                  70                  75                  80

His Asp Thr Leu Ala Pro Asp Glu Gly Phe Ala Arg Tyr Phe Gly Asp
                85                  90                  95

Asn Arg Thr Pro Asp Val Asp Pro Gly Thr Ala Ile Gly Asn Arg Thr
            100                 105                 110

Leu Leu Arg Gln Phe Glu Phe His Thr Ser Pro Asp Gln Gly Lys Arg
        115                 120                 125

Glu Arg Ala Ala Pro Val Leu Leu Phe Arg Ser Thr Lys Lys Gly Phe
    130                 135                 140

Lys Glu Phe Ser Gly Leu Ala Leu Ile Val Gly Ala Arg Arg Val Thr
145                 150                 155                 160

Gln Phe Ser Glu Lys Asn Gly Gly Phe Phe Thr Asn Tyr Leu Phe Asp
                165                 170                 175

Leu Ala Val Leu Ser Leu Thr Glu Glu Asp Glu Ser Leu Ala Met Leu
            180                 185                 190

Trp Ile His Asp Arg Arg Asp Pro Ser Arg Ala Cys Gly Val Ala Asn
        195                 200                 205

Ala Met Ala Pro Lys Ala Trp Gln Arg Trp Val Lys Phe Gly Ser Pro
    210                 215                 220

Glu Ile Glu Arg Ile Lys Arg Arg Val Ala Arg Tyr His Ile Leu Pro
225                 230                 235                 240

Lys Arg Asp Gln Val Ala Pro Val Ser Ser Glu Gly Gly Lys Thr Leu
                245                 250                 255

Glu Ala Ile Tyr Arg Phe Tyr Glu Pro Lys Arg His Arg Phe Glu Ala
            260                 265                 270

Leu Ala Ser Leu Ala Cys Glu Ser Met Val Arg Gly Thr Gly Ala Glu
        275                 280                 285

Tyr His Arg Gly Trp Leu Thr Arg Gly Thr Gly Asp Gly Gly Leu Asp
    290                 295                 300

Phe Val Gly Arg Ile Asp Ile Gly Glu Gly Leu Trp Gly Thr Lys Leu
305                 310                 315                 320

Val Val Leu Gly Gln Ala Lys Cys Glu Lys Ile Asp Ala Pro Thr Gly
                325                 330                 335

Gly Val His Ile Ala Arg Thr Val Ala Arg Leu Arg Arg Gly Trp Leu
            340                 345                 350

Gly Ala Tyr Val Thr Thr Ser Phe Phe Ser Glu Ala Val Gln Arg Glu
        355                 360                 365

Val His Asp Asp Gln Tyr Pro Val Leu Leu Asn Gly Ala Gly Leu
    370                 375                 380

Ala Ala Glu Val Thr Lys Leu Arg Leu Glu Gly Gly Phe Ala Ser Thr
385                 390                 395                 400

Glu Gln Phe Leu Glu His Ile Asp Ala Asp Tyr Glu Ala Gln Val Ser
                405                 410                 415

Ser Arg Arg Pro Glu Glu Val Leu Trp Glu
            420                 425

<210> SEQ ID NO 22
<211> LENGTH: 456
<212> TYPE: PRT
<213> ORGANISM: Mycobacterium sp.

<400> SEQUENCE: 22

Met Asn Gly Pro Lys Ala Asp Ile Ala Trp Ala Ser Ala Glu Val
1               5                   10                  15

Ala Asn Lys Pro Arg Leu Val Phe Val Gly Asp Glu Leu Arg Tyr Ala
            20                  25                  30

Gln Gly Ala Asn Gln Arg Asp Val Glu Leu Asp Gly Phe Val Asn Tyr
            35                  40                  45

His Trp Leu Thr Ser Pro Gly Gly Leu Gly Leu Pro Lys Val Met Leu
        50                  55                  60

Glu Ala Gly Ile Asn Ala Pro Ala Glu Val Val Gly Pro Asp Arg Ser
65              70                  75                  80

Arg Arg Ala Leu Ile Ala Ile Arg Ser Ser Pro Trp Lys Ala Gly His
                85                  90                  95

Glu Thr Asn Pro Trp His Asp Glu Phe Asp Leu Asp His Gly His Val
            100                 105                 110

Arg Tyr Phe Gly Asp His Lys Pro Ser Thr Val Gly Leu Pro Gly Glu
        115                 120                 125

Thr Lys Gly Asn Arg Leu Leu Leu Glu Ala Ala Arg Leu His Ala Gly
    130                 135                 140

Thr Thr Arg Glu Glu Arg Leu Leu Ala Pro Pro Leu Phe Leu Phe Arg
145                 150                 155                 160

Ala Val Thr Val His Arg Ala Gly Arg Ala Val Val Lys Gly His Val
                165                 170                 175

Glu Phe Cys Gly Ala Ala Ile Ile Glu Arg Leu Glu His Val Val Gln
            180                 185                 190

Arg Asp Pro Glu Thr Gly Arg Ser Phe Pro Asn Leu Ser Leu Asp Leu
        195                 200                 205

Ala Val Val Ser Gly Gly Glu Ile Asp Gly Val Asp Phe Arg Trp Ile
    210                 215                 220

Asp Asp Arg Arg Asn Ala Leu Ala Ala Gly Glu Thr Leu Arg His
225                 230                 235                 240

Ala Pro Glu Ser Trp Ile Arg Trp Val Arg Gln Gly Arg Leu Ala Ile
                245                 250                 255

Pro Gly Ile Arg Arg Arg Val Leu Ala Ser Ala Val Gln Ser Ser Lys
            260                 265                 270

Glu Gln Gln Pro Ala Ser Gly Ser Ala Glu Ala Ala Thr Leu Gln Thr
        275                 280                 285

Leu Tyr Lys Phe Tyr Asp Gly Arg Lys His Ala Phe Glu Leu Leu Ala
    290                 295                 300

Ser Arg Val Ala Ala Glu Val Phe Arg Glu Ser Gly Ala Arg Tyr Lys
305                 310                 315                 320

Glu Gly Trp Leu Ser Arg Ser Ser Gly Asp Gly Val Asp Phe Ile
                325                 330                 335

Gly Arg Ile Asp Met Gly Ser Leu Lys Ala Ser Thr Pro Val Val Val
            340                 345                 350

Leu Gly Gln Ala Lys Cys Ile Gln Pro Thr Ser Ser Val Ser Pro Glu
        355                 360                 365

Gln Val Ala Arg Val Val Ala Arg Leu Arg Arg Gly Trp Ile Gly Val
    370                 375                 380

Tyr Val Thr Thr Gly Ser Phe Ser Arg Gln Ala Gln Val Glu Ile Ile
385                 390                 395                 400

Asp Asp Gln Tyr Pro Val Val Leu Ile Ala Gly Gly Thr Leu Ala Ala
                405                 410                 415

Thr Val Arg Arg Met Val Gln Ala Asn Tyr Gly Gly Asp Leu Asp Ala
            420                 425                 430

Leu Leu Ala Ser Thr Val Asp Glu Tyr Gly Ala Ala Val Thr His Arg
        435                 440                 445

Arg Pro Glu Glu Val Ile Ser Leu
    450                 455

<210> SEQ ID NO 23
<211> LENGTH: 61
<212> TYPE: PRT
<213> ORGANISM: Veillonella parvula
<220> FEATURE:
<221> NAME/KEY: MISC_FEATURE
<222> LOCATION: (1)..(61)
<223> OTHER INFORMATION: conserved motif in the N-terminal domain of seq
      id no. 7

<400> SEQUENCE: 23

Glu Asp Ile Asp Trp Pro Asp Val Leu Glu Ala Glu Thr Gly Lys Phe
1               5                   10                  15

Lys Tyr Tyr Gly Asp Asn Lys Arg Pro Gly Asp Lys Val Asp Ser Lys
            20                  25                  30

Lys Gly Asn Leu Ile Leu Glu Thr Ile Phe Asn Glu Lys Asn Arg Asn
        35                  40                  45

Lys Ile Pro Pro Val Phe Ile Phe Met Lys Asn Pro Thr
    50                  55                  60

<210> SEQ ID NO 24
<211> LENGTH: 66
<212> TYPE: PRT
<213> ORGANISM: Catenibacterium mitsuokai
<220> FEATURE:
<221> NAME/KEY: MISC_FEATURE
<222> LOCATION: (1)..(66)
<223> OTHER INFORMATION: conserved motif in the N-terminal domain of seq
      id no 8

<400> SEQUENCE: 24

Glu Glu Leu Glu Trp Pro Asp Phe Leu Asp Glu Thr Gly Val Phe
1               5                   10                  15

Arg Tyr Tyr Gly Asp Asn Arg Lys Pro Gly Asn Asp Ile Arg Asn Thr
            20                  25                  30

Lys Lys Lys Gly Asn Leu Leu Leu Glu Glu Val Phe Glu Leu Leu Asn
        35                  40                  45

Ser Asn Asn Leu Glu Asp Met Pro Pro Phe Phe Val Phe Lys Lys Thr
    50                  55                  60

Gly Asn
65

<210> SEQ ID NO 25
<211> LENGTH: 68
<212> TYPE: PRT
<213> ORGANISM: Frankia sp.
<220> FEATURE:
<221> NAME/KEY: MISC_FEATURE
<222> LOCATION: (1)..(68)
<223> OTHER INFORMATION: conserved motif in the N-terminal domain of seq -continued id no. 9

<400> SEQUENCE: 25

Ala Val Ala Asp Trp Pro Asp Thr Leu Asp Pro Ser Thr Gly Val Phe
1               5                   10                  15

Thr Tyr Tyr Gly Asp Asn Arg Lys Pro Gly Arg Asp Leu His Asp Thr
            20                  25                  30

Gln Arg Ser Gly Asn Leu Leu Leu Arg Asp Val Phe Glu His Ala His
        35                  40                  45

Gly Ser Val Glu Glu Arg Arg Thr Val Pro Pro Phe Leu Leu Phe Glu
    50                  55                  60

Thr Ala Pro Pro
65

<210> SEQ ID NO 26
<211> LENGTH: 68
<212> TYPE: PRT
<213> ORGANISM: Streptomyces griseoflavus
<220> FEATURE:
<221> NAME/KEY: MISC_FEATURE
<222> LOCATION: (1)..(68)
<223> OTHER INFORMATION: conserved motif in the N-terminal domain of seq
      id no. 10

<400> SEQUENCE: 26

Gly Glu Val Asp Trp Pro Asp Tyr Leu Asp Val Glu Thr Gly Thr Phe
1               5                   10                  15

Thr Tyr Tyr Gly Asp Asn Arg Arg Pro Gly Gln Ser Leu His Glu Thr
            20                  25                  30

Pro Arg Ser Gly Asn Ile Leu Leu Arg Asp Ala Phe Ala Ala Ser His
        35                  40                  45

Gly Thr Pro Ala Asp Arg Ser Lys Val Pro Pro Phe Phe Leu Phe Glu
    50                  55                  60

Lys Ala Ala Ala
65

<210> SEQ ID NO 27
<211> LENGTH: 66
<212> TYPE: PRT
<213> ORGANISM: Azoarcus sp.
<220> FEATURE:
<221> NAME/KEY: MISC_FEATURE
<222> LOCATION: (1)..(66)
<223> OTHER INFORMATION: conserved motif in the N-terminal domain of seq
      id no.11

<400> SEQUENCE: 27

Ala Glu Pro Glu Trp Pro Asp Gln Leu Asp Glu Thr Thr Gly Thr Phe
1               5                   10                  15

Ile Tyr Tyr Gly Asp Asn Arg His Pro Gly Arg Leu Leu His Asp Thr
            20                  25                  30

Pro Arg Phe Gly Asn Gln Leu Leu Arg Gln Ile Phe Asp Trp Ala His
        35                  40                  45

Leu Gly Gln Arg His Leu Val Pro Pro Ile Leu Val Phe Thr Thr Glu
    50                  55                  60

Ala Thr
65

<210> SEQ ID NO 28
<211> LENGTH: 28
<212> TYPE: PRT
<213> ORGANISM: Burkholderia cenocepacia

```
<220> FEATURE:
<221> NAME/KEY: MISC_FEATURE
<222> LOCATION: (1)..(28)
<223> OTHER INFORMATION: conserved motif in the N-terminal domain of seq
      id no. 12

<400> SEQUENCE: 28

Met Leu Arg Asn Leu Phe Asp Glu Ala His Gln Phe Gln Gln Ser Ser
1               5                   10                  15

Ser Phe Pro Pro Ile Leu Leu Phe Gly Asn Ala Gly
            20                  25

<210> SEQ ID NO 29
<211> LENGTH: 68
<212> TYPE: PRT
<213> ORGANISM: Legionella pneumophila
<220> FEATURE:
<221> NAME/KEY: MISC_FEATURE
<222> LOCATION: (1)..(68)
<223> OTHER INFORMATION: conserved motif in the N-terminal domain of seq
      id no. 13

<400> SEQUENCE: 29

Glu Asp Gly Asp Trp Pro Asp Ser Ile Asp Thr Ser Lys Gly Gln Phe
1               5                   10                  15

Ile Tyr Tyr Gly Asp Asn Lys His Pro Gly His Asp Ile His Asp Thr
            20                  25                  30

Pro Arg Gln Gly Asn Ala Thr Leu Lys Met Leu Phe Asp Ser Thr His
        35                  40                  45

Asn Glu Lys Asp Ala Arg Arg Ile Val Pro Pro Ile Phe Ile Phe Val
    50                  55                  60

Lys Tyr Pro Thr
65

<210> SEQ ID NO 30
<211> LENGTH: 67
<212> TYPE: PRT
<213> ORGANISM: Ralstonia metallidurans
<220> FEATURE:
<221> NAME/KEY: MISC_FEATURE
<222> LOCATION: (1)..(67)
<223> OTHER INFORMATION: conserved motif in the N-terminal domain of seq
      id no. 14

<400> SEQUENCE: 30

Glu Asp Lys Asp Trp Pro Asp Thr Leu Asp Leu Ser Thr Gly Lys Phe
1               5                   10                  15

Val Tyr Phe Gly Asp Asn Lys Thr Pro Gly His Glu Leu His Glu Thr
            20                  25                  30

Arg Gly Gly Asn Lys Val Leu Arg Tyr Ser Phe Glu Arg Leu His Ala
        35                  40                  45

Ala Val Asn Pro Arg Ala Asp Val Ala Pro Phe Leu Val Phe Lys Lys
    50                  55                  60

Tyr Pro Leu
65

<210> SEQ ID NO 31
<211> LENGTH: 65
<212> TYPE: PRT
<213> ORGANISM: Ruminococcus lactaris
<220> FEATURE:
<221> NAME/KEY: MISC_FEATURE
<222> LOCATION: (1)..(65)
<223> OTHER INFORMATION: conserved motif in the N-terminal domain of seq
      id no. 15
```

```
<400> SEQUENCE: 31

Lys His Pro Asp Trp Leu Asp Asn Ile Asp Tyr Glu Ser Gly Ile Ile
1               5                   10                  15

Gln Tyr Tyr Gly Asp Asn Arg Glu Pro Gly Arg Glu Leu His Asp Ser
            20                  25                  30

Lys Arg Gly Gly Asn Lys Val Leu Arg Asp Val Phe Glu Met Leu Gln
        35                  40                  45

Asp Asn Arg Arg Gln Glu Ile Pro Pro Phe Phe Tyr Phe Glu Ser Glu
    50                  55                  60

Glu
65

<210> SEQ ID NO 32
<211> LENGTH: 68
<212> TYPE: PRT
<213> ORGANISM: Lactobacillus helveticus
<220> FEATURE:
<221> NAME/KEY: MISC_FEATURE
<222> LOCATION: (1)..(68)
<223> OTHER INFORMATION: conserved motif in the N-terminal domain of seq
      id no. 16

<400> SEQUENCE: 32

Ile Asn Tyr Asn Pro Trp Glu Asp Glu Phe Asn Glu Asp Val Gly Tyr
1               5                   10                  15

Ile Asn Tyr Tyr Gly Asp Asn Lys Arg Pro Asp Thr Asp Pro Ala Thr
            20                  25                  30

Thr Arg Gly Asn Lys Tyr Leu Leu Asp Gln Phe Lys Ile Ser His Asp
        35                  40                  45

Pro Asn Pro Glu Val Arg Ala Thr Ala Val Pro Ile Ile Phe Phe Glu
    50                  55                  60

Thr Arg Lys Gln
65

<210> SEQ ID NO 33
<211> LENGTH: 68
<212> TYPE: PRT
<213> ORGANISM: Lactobacillus helveticus
<220> FEATURE:
<221> NAME/KEY: MISC_FEATURE
<222> LOCATION: (1)..(68)
<223> OTHER INFORMATION: conserved motif in the N-terminal domain of seq
      id no. 17

<400> SEQUENCE: 33

Ile Asn Tyr Asn Pro Trp Glu Asp Glu Phe Asn Glu Asp Val Gly Tyr
1               5                   10                  15

Ile Asn Tyr Tyr Gly Asp Asn Lys Arg Pro Asp Thr Asp Pro Ala Thr
            20                  25                  30

Thr Arg Gly Asn Lys Tyr Leu Leu Asp Gln Phe Lys Ile Ser His Asp
        35                  40                  45

Pro Asn Ser Glu Val Arg Ala Thr Ala Val Pro Ile Ile Phe Phe Glu
    50                  55                  60

Thr Arg Lys Gln
65

<210> SEQ ID NO 34
<211> LENGTH: 68
```

```
<212> TYPE: PRT
<213> ORGANISM: Shewanella pealeana
<220> FEATURE:
<221> NAME/KEY: MISC_FEATURE
<222> LOCATION: (1)..(68)
<223> OTHER INFORMATION: conserved motif in the N-terminal domain of seq
      id no. 18

<400> SEQUENCE: 34

Ser Ile Glu Thr Pro Trp Glu Asp Phe Tyr Asp Val Asp Asn Gly His
1               5                   10                  15

Ile Arg Tyr Phe Gly Asp Asn Lys Glu Pro Gly Lys Asp Pro Ala Thr
            20                  25                  30

Ala Pro Gly Asn Lys Ala Leu Leu Glu Ala Phe Arg Leu Ala His Ser
        35                  40                  45

His Ser Ala Glu Glu Arg Ala Leu Thr Pro Pro Ile Leu Phe Phe Lys
    50                  55                  60

Arg Ala Val Ile
65

<210> SEQ ID NO 35
<211> LENGTH: 68
<212> TYPE: PRT
<213> ORGANISM: Shewanella baltica
<220> FEATURE:
<221> NAME/KEY: MISC_FEATURE
<222> LOCATION: (1)..(68)
<223> OTHER INFORMATION: conserved motif in the N-terminal domain of seq
      id no. 19

<400> SEQUENCE: 35

Ser Ile Glu Thr Pro Trp Glu Asp Phe Tyr Asp Val Asp Asn Gly His
1               5                   10                  15

Ile Arg Tyr Phe Gly Asp Asn Lys Glu Pro Gly Lys Asp Pro Ala Thr
            20                  25                  30

Ala Pro Gly Asn Lys Ala Leu Leu Glu Ala Phe Arg Leu Ala His Ser
        35                  40                  45

His Asn Val Asp Glu Arg Leu Leu Thr Pro Pro Ile Leu Phe Phe Lys
    50                  55                  60

Arg Ala Ile Val
65

<210> SEQ ID NO 36
<211> LENGTH: 68
<212> TYPE: PRT
<213> ORGANISM: Moritella sp.
<220> FEATURE:
<221> NAME/KEY: MISC_FEATURE
<222> LOCATION: (1)..(68)
<223> OTHER INFORMATION: conserved motif in the N-terminal domain of seq
      id no. 20

<400> SEQUENCE: 36

Ser Met Glu Asn Pro Trp His Asp Thr Leu Ala Pro Asp Glu Gly Phe
1               5                   10                  15

Ala Arg Tyr Phe Gly Asp Asn Arg Thr Pro Asp Val Ala Pro Gly Thr
            20                  25                  30

Ala Ile Gly Asn Arg Thr Leu Leu Arg Gln Phe Glu Phe His Thr Ser
        35                  40                  45

Pro Asp Gln Gly Lys Arg Glu Arg Ala Ala Pro Val Leu Leu Phe Arg
    50                  55                  60

Ser Thr Lys Lys
65
```

```
<210> SEQ ID NO 37
<211> LENGTH: 68
<212> TYPE: PRT
<213> ORGANISM: Xanthomonas campestris
<220> FEATURE:
<221> NAME/KEY: MISC_FEATURE
<222> LOCATION: (1)..(68)
<223> OTHER INFORMATION: conserved motif in the N-terminal domain of seq
      id no. 21

<400> SEQUENCE: 37

Ser Met Glu Asn Pro Trp His Asp Thr Leu Ala Pro Asp Gly Phe
1               5                   10                  15

Ala Arg Tyr Phe Gly Asp Asn Arg Thr Pro Asp Val Asp Pro Gly Thr
                20                  25                  30

Ala Ile Gly Asn Arg Thr Leu Leu Arg Gln Phe Glu Phe His Thr Ser
            35                  40                  45

Pro Asp Gln Gly Lys Arg Glu Arg Ala Ala Pro Val Leu Leu Phe Arg
        50                  55                  60

Ser Thr Lys Lys
65

<210> SEQ ID NO 38
<211> LENGTH: 69
<212> TYPE: PRT
<213> ORGANISM: Mycobacterium sp.
<220> FEATURE:
<221> NAME/KEY: MISC_FEATURE
<222> LOCATION: (1)..(69)
<223> OTHER INFORMATION: conserved motif in the N-terminal domain of seq
      id no. 22

<400> SEQUENCE: 38

His Glu Thr Asn Pro Trp His Asp Glu Phe Asp Leu Asp His Gly His
1               5                   10                  15

Val Arg Tyr Phe Gly Asp His Lys Pro Ser Thr Val Gly Leu Pro Gly
                20                  25                  30

Glu Thr Lys Gly Asn Arg Leu Leu Leu Glu Ala Ala Arg Leu His Ala
            35                  40                  45

Gly Thr Thr Arg Glu Glu Arg Leu Leu Ala Pro Pro Leu Phe Leu Phe
        50                  55                  60

Arg Ala Val Thr Val
65

<210> SEQ ID NO 39
<211> LENGTH: 63
<212> TYPE: PRT
<213> ORGANISM: Veillonella parvula
<220> FEATURE:
<221> NAME/KEY: MISC_FEATURE
<222> LOCATION: (1)..(63)
<223> OTHER INFORMATION: conserved motif in the C-terminal domain of seq
      id no. 7

<400> SEQUENCE: 39

Gln Tyr Tyr Lys Asp Glu Pro Tyr Lys Phe Glu Tyr Phe Ala Ala Lys
1               5                   10                  15

Leu Val Gly Leu Met Asp Asn Asn Phe Leu Asn Phe Asn Ile Thr Arg
                20                  25                  30

Thr Val Arg Asp Gly Gly Ile Asp Ala Ile Gly Glu Tyr Arg Leu Gly
            35                  40                  45
```

```
His Lys Asn Asn Ser Ile Lys Leu Arg Cys Ala Leu Glu Ala Lys
            50                  55                  60
```

<210> SEQ ID NO 40
<211> LENGTH: 66
<212> TYPE: PRT
<213> ORGANISM: Catenibacterium mitsuokai
<220> FEATURE:
<221> NAME/KEY: MISC_FEATURE
<222> LOCATION: (1)..(66)
<223> OTHER INFORMATION: conserved motif in the C-terminal domain of seq
      id no. 8

<400> SEQUENCE: 40

```
Glu His Tyr Lys Asp Asn Pro Tyr Gly Phe Glu Ser Cys Ala Met Asp
1               5                   10                  15

Leu Leu Met Lys Met Asp Asn His Phe Val Asp Phe Asn Leu Thr Arg
            20                  25                  30

Pro Trp Arg Asp Gly Gly Arg Asp Ser Ile Gly Tyr Tyr Ser Ile Asn
        35                  40                  45

Ser Gly Gly Lys Val Asn Ala Pro Leu Lys Ile Asp Cys Ala Leu Glu
    50                  55                  60

Ala Met
65
```

<210> SEQ ID NO 41
<211> LENGTH: 63
<212> TYPE: PRT
<213> ORGANISM: Frankia sp.
<220> FEATURE:
<221> NAME/KEY: MISC_FEATURE
<222> LOCATION: (1)..(63)
<223> OTHER INFORMATION: conserved motif in the C-terminal domain of seq
      id no. 9

<400> SEQUENCE: 41

```
Glu His Tyr Arg Gly His Glu His Asp Phe Glu Phe Cys Ala Val Glu
1               5                   10                  15

Leu Trp Arg Leu Ile Ala Pro Ala Thr Gly Arg Cys Asp Val Thr Pro
            20                  25                  30

Pro Ser Arg Asp Gly Gly Arg Asp Ala Ile Gly Asp Tyr Ile Leu Gly
        35                  40                  45

Pro Leu Ser Asp Pro Ile Ala Ile Asp Phe Ala Leu Glu Ala Lys
    50                  55                  60
```

<210> SEQ ID NO 42
<211> LENGTH: 63
<212> TYPE: PRT
<213> ORGANISM: Streptomyces griseoflavus
<220> FEATURE:
<221> NAME/KEY: MISC_FEATURE
<222> LOCATION: (1)..(63)
<223> OTHER INFORMATION: conserved motif int he C-terminal domain of seq
      id no. 10

<400> SEQUENCE: 42

```
Asp Tyr Phe Arg Gly Arg Glu His Asp Phe Glu Leu Cys Ala Val Ala
1               5                   10                  15

Ile Trp Arg Leu Met Ala Pro Ser Thr Gly Ala Val Asp Val Thr Arg
            20                  25                  30

Pro Ser Arg Asp Gly Gly Arg Asp Ala Val Gly Thr Tyr Leu Leu Gly
        35                  40                  45

Pro Ala Ala Asn Arg Ile Ala Val Asp Phe Ala Leu Glu Ala Lys
    50                  55                  60
```

```
<210> SEQ ID NO 43
<211> LENGTH: 63
<212> TYPE: PRT
<213> ORGANISM: Azoarcus sp.
<220> FEATURE:
<221> NAME/KEY: MISC_FEATURE
<222> LOCATION: (1)..(63)
<223> OTHER INFORMATION: conserved motif in the C-terminal domain of seq
      id no. 11

<400> SEQUENCE: 43

Gln Arg Tyr Lys Glu Asn Pro Phe Gly Phe Glu Ala Cys Ala Gly Ala
1               5                   10                  15

Leu Thr Arg Leu Leu Leu Pro Asp Val Ala Arg Leu Asp Leu Thr Arg
                20                  25                  30

Pro Trp Arg Asp Gly Gly Arg Asp Gly Ile Gly Arg Leu Arg Ile Gly
            35                  40                  45

Gln Ser Pro Ala Ala Ile Glu Val Asp Phe Ala Leu Glu Ala Lys
        50                  55                  60

<210> SEQ ID NO 44
<211> LENGTH: 63
<212> TYPE: PRT
<213> ORGANISM: Burkholderia cenocepacia
<220> FEATURE:
<221> NAME/KEY: MISC_FEATURE
<222> LOCATION: (1)..(63)
<223> OTHER INFORMATION: conserved motif in the C-terminal domain of seq
      id no. 12

<400> SEQUENCE: 44

Glu His Tyr Lys Glu Asp Pro Tyr Ala Phe Glu Arg Cys Ala Met Glu
1               5                   10                  15

Leu Ala Arg Leu Phe Met Pro Ala Ile Gln His Trp Glu Leu Thr Arg
                20                  25                  30

Pro Trp Arg Asp Gly Gly Arg Asp Ala Leu Gly Thr Tyr Arg Ile Gly
            35                  40                  45

His Gly Ala Gly Ala Ile Asp Val Glu Phe Ala Met Glu Ala Lys
        50                  55                  60

<210> SEQ ID NO 45
<211> LENGTH: 63
<212> TYPE: PRT
<213> ORGANISM: Legionella pneumophila
<220> FEATURE:
<221> NAME/KEY: MISC_FEATURE
<222> LOCATION: (1)..(63)
<223> OTHER INFORMATION: conserved motif in the C-terminal domain of seq
      id no. 13

<400> SEQUENCE: 45

Asp Tyr Phe Cys Glu Ala Pro Ile Lys Phe Glu Ala Cys Ala Ala Lys
1               5                   10                  15

Ile Phe Gln Leu Tyr Asp Glu Asn Val Leu Ile Asp Glu Ile Thr Arg
                20                  25                  30

Ser Ala Val Asp Gly Gly Lys Asp Ala Ile Gly Arg Tyr Val Leu Gly
            35                  40                  45

Ile Lys Glu Asp Pro Val Tyr Ala Glu Phe Phe Leu Glu Ala Lys
        50                  55                  60

<210> SEQ ID NO 46
<211> LENGTH: 63
<212> TYPE: PRT
```

```
<213> ORGANISM: Ralstonia metallidurans
<220> FEATURE:
<221> NAME/KEY: MISC_FEATURE
<222> LOCATION: (1)..(63)
<223> OTHER INFORMATION: conserved motif in the C-terminal domain of seq
      id no. 14

<400> SEQUENCE: 46

Gln His Tyr Lys Gly Ala Pro Ile Ala Phe Glu Ala Phe Ala Ala Arg
1               5                   10                  15

Val Phe Gln Met Thr Asp Glu Arg Val Val Ile Asp Glu Ile Thr Arg
                20                  25                  30

Gly Val Val Asp Gly Gly Arg Asp Ala Ile Gly Arg Tyr Arg Leu Gly
            35                  40                  45

Ser Met Ala Asp Pro Val Tyr Ala Glu Phe Ser Leu Glu Ala Lys
        50                  55                  60

<210> SEQ ID NO 47
<211> LENGTH: 62
<212> TYPE: PRT
<213> ORGANISM: Ruminococcus lactaris
<220> FEATURE:
<221> NAME/KEY: MISC_FEATURE
<222> LOCATION: (1)..(62)
<223> OTHER INFORMATION: conserved motif in the C-terminal domain of seq
      id no. 15

<400> SEQUENCE: 47

Asp Tyr Phe Asp Asn Pro Tyr Glu Phe Glu Lys Cys Ala Met Lys Ile
1               5                   10                  15

Val Gln Leu Met Asp Ser Asn Ile His Ser Leu Lys His Thr Arg Phe
                20                  25                  30

Val Arg Asp Gly Gly Arg Asp Ala Ile Gly Leu Tyr Arg Ile Gly Arg
            35                  40                  45

Gln Cys Asp Gly Val Asp Val Glu Phe Ala Leu Glu Ala Lys
        50                  55                  60

<210> SEQ ID NO 48
<211> LENGTH: 65
<212> TYPE: PRT
<213> ORGANISM: Lactobacillus helveticus
<220> FEATURE:
<221> NAME/KEY: MISC_FEATURE
<222> LOCATION: (1)..(65)
<223> OTHER INFORMATION: conserved motif in the C-terminal domain of seq
      id no. 16

<400> SEQUENCE: 48

Ser Lys Ala His Ser Gly Asp Phe Glu Phe Glu Gly Leu Ala Lys Glu
1               5                   10                  15

Ile Thr Arg Leu Ile Ile Gly Asp Ala Cys His Asp Gly Trp Val Thr
                20                  25                  30

Lys Ser Ser Gly Asp Gly Gly Tyr Asp Phe Val Leu Arg Val Asp Ile
            35                  40                  45

Gly Thr Lys Gly Ile Ser Gln Val Arg Gln Val Val Leu Gly Gln Ala
        50                  55                  60

Lys
65

<210> SEQ ID NO 49
<211> LENGTH: 65
<212> TYPE: PRT
<213> ORGANISM: Lactobacillus helveticus
<220> FEATURE:
```

```
<221> NAME/KEY: MISC_FEATURE
<222> LOCATION: (1)..(65)
<223> OTHER INFORMATION: conserved motif in the C-terminal domain of seq
      id no. 17

<400> SEQUENCE: 49
```

Ser Lys Ala His Ser Gly Asp Phe Glu Phe Glu Gly Leu Ala Lys Glu
1               5                   10                  15

Ile Thr Arg Leu Ile Ile Gly Asp Ala Cys His Asp Gly Trp Val Thr
            20                  25                  30

Lys Ser Ser Gly Asp Gly Gly Tyr Asp Phe Val Leu Arg Val Asp Ile
        35                  40                  45

Gly Thr Lys Gly Ile Ser Gln Val Arg Gln Val Val Leu Gly Gln Ala
    50                  55                  60

Lys
65

```
<210> SEQ ID NO 50
<211> LENGTH: 67
<212> TYPE: PRT
<213> ORGANISM: Shewanella pealeana
<220> FEATURE:
<221> NAME/KEY: MISC_FEATURE
<222> LOCATION: (1)..(67)
<223> OTHER INFORMATION: conserved motif in the C-terminal domain of seq
      id no. 18

<400> SEQUENCE: 50
```

Ile Tyr Tyr Ala Asn Lys Lys His Arg Phe Glu Ala Leu Ala Glu Val
1               5                   10                  15

Ile Ala Ala Arg Val Ile Asp Arg Glu Phe Gly Ile Tyr His Lys Gly
            20                  25                  30

Trp Val Thr Gln Gly Ser Ser Asp Gly Gly Ala Asp Phe Val Gly Lys
        35                  40                  45

Val Thr Leu Gly Ser Gly Phe Ser Lys Val Glu Leu Ile Val Leu Gly
    50                  55                  60

Gln Ala Lys
65

```
<210> SEQ ID NO 51
<211> LENGTH: 67
<212> TYPE: PRT
<213> ORGANISM: Shewanella baltica
<220> FEATURE:
<221> NAME/KEY: MISC_FEATURE
<222> LOCATION: (1)..(67)
<223> OTHER INFORMATION: conserved motif in the C-terminal domain of seq
      id no. 19

<400> SEQUENCE: 51
```

Asp Tyr Tyr Ala Asn Lys Lys His Arg Phe Glu Ala Leu Ala Glu Val
1               5                   10                  15

Ile Ala Glu Arg Val Ile Asp Arg Glu Leu Gly Ile Tyr Gln Lys Gly
            20                  25                  30

Trp Val Thr Gln Gly Ser Gly Asp Gly Gly Ala Asp Phe Ile Gly Lys
        35                  40                  45

Val Thr Leu Gly Ser Gly Phe Ser Lys Val Glu Leu Ile Val Leu Gly
    50                  55                  60

Gln Ala Lys
65

```
<210> SEQ ID NO 52
```

```
<211> LENGTH: 67
<212> TYPE: PRT
<213> ORGANISM: Moritella sp.
<220> FEATURE:
<221> NAME/KEY: MISC_FEATURE
<222> LOCATION: (1)..(67)
<223> OTHER INFORMATION: conserved motif in the C-terminal domain of seq
      id no. 20

<400> SEQUENCE: 52

Lys Phe Tyr Asp Gly Arg Lys His His Phe Glu Ala Leu Ala Glu Phe
1               5                   10                  15

Ile Thr Glu Arg Val Ile Gly Lys Glu Leu Gly Ile Tyr His Lys Gly
            20                  25                  30

Trp Ile Thr Gln Gly Ser Ser Asp Gly Gly Ala Asp Phe Ile Gly Lys
        35                  40                  45

Val Val Leu Gly Ser Gly Phe Ser Lys Val Glu Leu Ile Val Leu Gly
    50                  55                  60

Gln Ala Lys
65

<210> SEQ ID NO 53
<211> LENGTH: 67
<212> TYPE: PRT
<213> ORGANISM: Xanthomonas campestris
<220> FEATURE:
<221> NAME/KEY: MISC_FEATURE
<222> LOCATION: (1)..(67)
<223> OTHER INFORMATION: conserved motif in the C-terminal domain of seq
      id no. 21

<400> SEQUENCE: 53

Arg Phe Tyr Glu Pro Lys Arg His Arg Phe Glu Ala Leu Ala Ser Leu
1               5                   10                  15

Ala Cys Glu Ser Met Val Arg Gly Thr Gly Ala Glu Tyr His Arg Gly
            20                  25                  30

Trp Leu Thr Arg Gly Thr Gly Asp Gly Gly Leu Asp Phe Val Gly Arg
        35                  40                  45

Ile Asp Ile Gly Glu Gly Leu Trp Gly Thr Lys Leu Val Val Leu Gly
    50                  55                  60

Gln Ala Lys
65

<210> SEQ ID NO 54
<211> LENGTH: 67
<212> TYPE: PRT
<213> ORGANISM: Mycobacterium sp.
<220> FEATURE:
<221> NAME/KEY: MISC_FEATURE
<222> LOCATION: (1)..(67)
<223> OTHER INFORMATION: conserved motif in the C-terminal domain of seq
      id no. 22

<400> SEQUENCE: 54

Lys Phe Tyr Asp Gly Arg Lys His Ala Phe Glu Leu Leu Ala Ser Arg
1               5                   10                  15

Val Ala Ala Glu Val Phe Arg Glu Ser Gly Ala Arg Tyr Lys Glu Gly
            20                  25                  30

Trp Leu Ser Arg Ser Ser Gly Asp Gly Gly Val Asp Phe Ile Gly Arg
        35                  40                  45

Ile Asp Met Gly Ser Leu Lys Ala Ser Thr Pro Val Val Leu Gly
    50                  55                  60

Gln Ala Lys
```

<210> SEQ ID NO 55
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(17)
<223> OTHER INFORMATION: Xaa represents any naturally occurring amino acid

<400> SEQUENCE: 55

Trp Xaa Asp Xaa Xaa Xaa Xaa Xaa Xaa Xaa Xaa Xaa Xaa Xaa Tyr Xaa Gly
1               5                   10                  15

Asp

<210> SEQ ID NO 56
<211> LENGTH: 62
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(62)
<223> OTHER INFORMATION: Xaa represents any naturally occurring amino acid
<220> FEATURE:
<221> NAME/KEY: MISC_FEATURE
<222> LOCATION: (18)..(32)
<223> OTHER INFORMATION: There can be 10-15 amino acids at this location
<220> FEATURE:
<221> NAME/KEY: MISC_FEATURE
<222> LOCATION: (38)..(57)
<223> OTHER INFORMATION: There can be 10-20 amino acids at these locations.

<400> SEQUENCE: 56

Trp Xaa Asp Xaa Xaa Xaa Xaa Xaa Xaa Gly Xaa Xaa Xaa Tyr Xaa Gly
1               5                   10                  15

Asp Xaa Xaa Xaa Xaa Xaa Xaa Xaa Xaa Xaa Xaa Xaa Xaa Xaa
            20                  25                  30

Gly Asn Xaa Xaa Leu Xaa Xaa Xaa Xaa Xaa Xaa Xaa Xaa Xaa Xaa
        35                  40                  45

Xaa Xaa Xaa Xaa Xaa Xaa Xaa Xaa Xaa Pro Xaa Xaa Xaa Phe
    50                  55                  60

<210> SEQ ID NO 57
<211> LENGTH: 63
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(63)
<223> OTHER INFORMATION: Xaa represents any naturally occurring amino acid at all positions other than 61.
<220> FEATURE:
<221> NAME/KEY: MISC_FEATURE
<222> LOCATION: (3)..(32)
<223> OTHER INFORMATION: There can be 20-30 amino acids at these locations.
<220> FEATURE:
<221> NAME/KEY: MISC_FEATURE

```
<222> LOCATION: (34)..(37)
<223> OTHER INFORMATION: There an be 2-4 amino acids at these locations.
<220> FEATURE:
<221> NAME/KEY: MISC_FEATURE
<222> LOCATION: (39)..(60)
<223> OTHER INFORMATION: There can be 19-22 amino acids at these
      locations.
<220> FEATURE:
<221> NAME/KEY: MISC_FEATURE
<222> LOCATION: (61)..(61)
<223> OTHER INFORMATION: Xaa at position 61 represents either Glycine or
      Glutamine.

<400> SEQUENCE: 57

Phe Glu Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Asp Xaa Xaa Xaa Xaa Asp Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Lys
    50                  55                  60

<210> SEQ ID NO 58
<211> LENGTH: 59
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(59)
<223> OTHER INFORMATION: Xaa represents any naturally occurring amino
      acid at all positions other than 24, 36, or 57.
<220> FEATURE:
<221> NAME/KEY: MISC_FEATURE
<222> LOCATION: (6)..(23)
<223> OTHER INFORMATION: There can be 15-18 amino acids at these
      locations.
<220> FEATURE:
<221> NAME/KEY: MISC_FEATURE
<222> LOCATION: (24)..(24)
<223> OTHER INFORMATION: Xaa at position 24 represents either Threonine
      or Serine.
<220> FEATURE:
<221> NAME/KEY: MISC_FEATURE
<222> LOCATION: (36)..(36)
<223> OTHER INFORMATION: Xaa at position 36 represents either Glycine or
      Leucine.
<220> FEATURE:
<221> NAME/KEY: MISC_FEATURE
<222> LOCATION: (37)..(56)
<223> OTHER INFORMATION: There can be 15-20 amino acids at these
      locations.
<220> FEATURE:
<221> NAME/KEY: MISC_FEATURE
<222> LOCATION: (57)..(57)
<223> OTHER INFORMATION: Xaa at position 57 represents either Glutamic
      Acid or Glutamine.

<400> SEQUENCE: 58

Phe Glu Xaa Xaa Ala Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Asp Gly Gly Xaa
            20                  25                  30

Asp Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Ala Lys
    50                  55
```